US011311512B2

(12) United States Patent
Porter et al.

(10) Patent No.: US 11,311,512 B2
(45) Date of Patent: Apr. 26, 2022

(54) LYMPH DIRECTING PRODRUGS

(71) Applicant: Monash University, Clayton (AU)

(72) Inventors: Chris Porter, South Melbourne (AU); Jamie Simpson, Chestnut Hill, MA (US); Natalie Trevaskis, Newington (AU); Tim Quach, Southbank (AU); Sifei Han, Bundoora (AU); Luojuan Hu, Bundoora (AU)

(73) Assignee: Monash University, Clayton (AU)

( * ) Notice: Subject to any disclaimer, the term of this patent is extended or adjusted under 35 U.S.C. 154(b) by 634 days.

(21) Appl. No.: 15/502,757

(22) PCT Filed: Aug. 12, 2015

(86) PCT No.: PCT/AU2015/050460
§ 371 (c)(1),
(2) Date: Feb. 8, 2017

(87) PCT Pub. No.: WO2016/023082
PCT Pub. Date: Feb. 18, 2016

(65) Prior Publication Data
US 2017/0326103 A1    Nov. 16, 2017

(30) Foreign Application Priority Data

Aug. 12, 2014   (AU) ................................ 2014903148

(51) Int. Cl.
| *A61K 9/00* | (2006.01) |
| *A61K 31/365* | (2006.01) |
| *A61K 31/568* | (2006.01) |
| *C07J 1/00* | (2006.01) |
| *C07J 7/00* | (2006.01) |

(Continued)

(52) U.S. Cl.
CPC ............ *A61K 31/365* (2013.01); *A61K 31/40* (2013.01); *A61K 31/4025* (2013.01);
(Continued)

(58) Field of Classification Search
CPC ...................................................... A61K 31/365
See application file for complete search history.

(56) References Cited

U.S. PATENT DOCUMENTS

| 4,587,262 A | 5/1986 | Arnould et al. |
| 4,958,046 A | 9/1990 | Rosenberg et al. |

(Continued)

FOREIGN PATENT DOCUMENTS

| JP | 2003-12691 A | 1/2003 |
| JP | 2003012691 A | 1/2003 |

(Continued)

OTHER PUBLICATIONS

Nieschlag et al, Testosterone replacement therapy: current trends and future directions, Human Reproduction Update, European Society of Human Reproduction and Embryology, Jan. 11, 2004.*

(Continued)

*Primary Examiner* — Paul W Dickinson
(74) *Attorney, Agent, or Firm* — Womble Bond Dickinson (US) LLP; Danielle L. Herritt; Mark R. DeLuca

(57) ABSTRACT

The present invention relates to compounds and their uses, in particular, compounds in the form of prodrugs that promote transport of a pharmaceutical agent to the lymphatic system and subsequently enhance release of the parent drug.

50 Claims, 24 Drawing Sheets

(51) Int. Cl.

| | | |
|---|---|---|
| *C07J 31/00* | (2006.01) | |
| *A61K 45/06* | (2006.01) | |
| *A61K 31/40* | (2006.01) | |
| *A61K 31/4025* | (2006.01) | |
| *A61P 5/24* | (2006.01) | |
| *B01J 20/281* | (2006.01) | |
| *C07J 5/00* | (2006.01) | |
| *C07J 9/00* | (2006.01) | |
| *G01N 30/00* | (2006.01) | |
| *C09J 5/00* | (2006.01) | |

(52) U.S. Cl.
CPC ............ *A61K 31/568* (2013.01); *A61K 45/06* (2013.01); *A61P 5/24* (2018.01); *C07J 1/0025* (2013.01); *C07J 1/0029* (2013.01); *C07J 7/002* (2013.01); *C07J 31/006* (2013.01); *G01N 30/48* (2013.01); *C07J 5/00* (2013.01); *C07J 9/00* (2013.01); *C07J 31/00* (2013.01); *C09J 5/00* (2013.01); *G01N 2030/486* (2013.01)

(56) References Cited

U.S. PATENT DOCUMENTS

| | | | |
|---|---|---|---|
| 5,962,440 | A | 10/1999 | Sulsky |
| 6,013,665 | A | 1/2000 | DeMichele et al. |
| 6,054,591 | A | 4/2000 | Aono et al. |
| 6,417,191 | B1 | 7/2002 | Barry et al. |
| 6,552,065 | B2 | 4/2003 | Remiszewski et al. |
| 7,390,799 | B2 | 6/2008 | Bruncko et al. |
| 7,557,210 | B2 | 7/2009 | Singh et al. |
| 7,635,690 | B2 | 12/2009 | Schinazi et al. |
| 8,138,347 | B2 | 3/2012 | Adams et al. |
| 8,338,439 | B2 | 12/2012 | Singh et al. |
| 8,455,510 | B2 | 6/2013 | Nan et al. |
| 2004/0204472 | A1 | 10/2004 | Briggs et al. |
| 2007/0191415 | A1 | 8/2007 | Kumar et al. |
| 2009/0023805 | A1 | 1/2009 | Marrast et al. |
| 2009/0297533 | A1 | 12/2009 | Lighter et al. |
| 2010/0298560 | A1 | 11/2010 | Choi et al. |
| 2011/0213028 | A1 | 9/2011 | Milne et al. |
| 2011/0243884 | A1* | 10/2011 | O'Shea ................... C07C 69/40 424/78.36 |
| 2013/0030007 | A1 | 1/2013 | Penninger et al. |
| 2014/0081016 | A1 | 3/2014 | Felzmann et al. |
| 2014/0234418 | A1 | 8/2014 | Coulter et al. |
| 2014/0328793 | A1 | 11/2014 | Gavegnano et al. |
| 2017/0326103 | A1 | 11/2017 | Porter et al. |
| 2018/0243425 | A1 | 8/2018 | Forter et al. |
| 2018/0258094 | A1 | 9/2018 | Long et al. |
| 2018/0318318 | A1 | 11/2018 | Wang et al. |
| 2019/0105299 | A1 | 4/2019 | Porter et al. |

FOREIGN PATENT DOCUMENTS

| | | |
|---|---|---|
| WO | WO-1994009010 A1 | 4/1994 |
| WO | WO-2001042246 A2 | 6/2001 |
| WO | WO-2002088112 | 11/2002 |
| WO | WO-2003063794 A2 | 8/2003 |
| WO | WO-2004019973 | 3/2004 |
| WO | WO-2004089925 | 10/2004 |
| WO | WO-2004106328 | 12/2004 |
| WO | WO-2005007623 | 1/2005 |
| WO | 2005/112919 A2 | 12/2005 |
| WO | WO-2005113554 | 12/2005 |
| WO | WO-2006078846 | 7/2006 |
| WO | WO-2006122806 | 11/2006 |
| WO | WO-2007016176 | 2/2007 |
| WO | WO-2007044729 | 4/2007 |
| WO | WO-2007053452 | 5/2007 |
| WO | WO-2007070514 | 6/2007 |
| WO | WO-2007084786 | 7/2007 |
| WO | WO-2007129161 | 11/2007 |
| WO | WO-2008039218 | 4/2008 |
| WO | WO-2008048611 A1 | 4/2008 |
| WO | WO-2008109943 | 9/2008 |
| WO | WO-2008118802 | 10/2008 |
| WO | WO-2009114512 | 9/2009 |
| WO | WO-2009143295 | 11/2009 |
| WO | WO-2011051967 A2 | 5/2011 |
| WO | WO-2011090760 A1 | 7/2011 |
| WO | WO-2011120044 A1 | 9/2011 |
| WO | WO-2015116904 | 8/2015 |
| WO | WO-2016023082 A1 | 2/2016 |
| WO | WO-2017041139 | 3/2017 |
| WO | WO-2017049245 A2 | 3/2017 |
| WO | WO-2018237282 A1 | 12/2018 |
| WO | WO-2019046478 A1 | 3/2019 |
| WO | WO-2019046491 A1 | 3/2019 |

OTHER PUBLICATIONS

Kihei et al., "Synthesis and Evaluation of the Anti-inflammatory Effects of Niflumic Acid Lipophilic Prodrugs in Brain Edema," *Arzneim.-Forsch./Drug Res.* 46(11):1040-1044, 1996.

Lalanne et al., "Metabolism evaluation of biomimetic prodrugs by in vitro models and mass spectrometry," *International Journal of Pharmaceutics* 379(2):235-243, 2009.

Lalanne et al., "Synthesis and biological evaluation of two glycerolipidic prodrugs of didanosine for direct lymphatic delivery against HIV," *Bioorganic & Medicinal Chemistry Letters* 17(8):2237-2240, 2007.

Sobczak, "Synthesis and characterization of polyester conjugates of ciprofloxacin," *European Journal of Medicinal Chemistry* 45(9):3844-3849, 2010.

Tranoy-Opalinski et al., "Design of Self-Immolative Linkers for Tumour-Activated Prodrug Therapy," *Anti-Cancer Agents in Medicinal Chemistry* 8(6):618-637, 2008.

Alouane et al., "Self-Immolative Spacers: Kinetic Aspects, Structure-Property Relationships, and Applications," Angewandte Reviews, vol. 54, 2015 (pp. 7492-7509).

Alouane et al., "Self-Immolative Spacers: Kinetic Aspects, Structure-Property Relationships, and Applications," Supporting Information, Angewandte Reviews, 2015 (10 pages).

Amsberry et al., "Amine Prodrugs Which Utilize Hydroxy Amide Lactonization. II. A Potential Esterase-Sensitive Amide Prodrug," Pharmceutical Research, vol. 8, No. 4, 1991 (pp. 455-461).

Blencowe et al., "Self-immolative linkers in polymeric delivery systems," Polymer Chemistry, vol. 2, No. 4, 2011 (pp. 773-790).

Charette et al. "Practical and Highly Regio- and Stereoselective Synthesis of 2-Substituted Dihydropyridines and Piperidines: Application to the Synthesis of (−)-Coniine," Journal of the American Chemical Society, vol. 123, No. 47, 2001 (p. 11829-11830).

Chowdhury et al., "Highly Regio- and Enantioselective Organocatalytic Conjugate Addition of Alkyl Methyl Ketones to a β-Silylmethylene Malonate," Organic Letters, vol. 11, No. 15, 2009 (pp. 3270-3273).

Cyr, P. et al., "Recent progress on nuclear receptor RORγ modulators," Bioorganic & Medicinal Chemistry Letters, vol. 26, No. 18, 2016 (pp. 4387-4393).

Deverre et al., "In-vitro evaluation of filaricidal activity of GABA and 1,3-dipalmitoyl-2-(4-aminobutyryl)glycerol HCl: a diglyceride prodrug," Journal of Pharmacy and Pharmacology, vol. 41, No. 3, 1989 (pp. 191-193).

Dommerholt et al., "Readily Accessible Bicyclononynes for Bioorthogonal Labeling and Three-Dimensional Imaging of Living Cells," Angewandte Chemie International Edition, vol. 49, 2010 (pp. 9422-9425).

Edwards et al., "Animal models for the study of intestinal lymphatic drug transport," Advanced Drug Delivery Reviews, vol. 50, No. 1, 2001 (pp. 45-60).

Garzon-Aburbeh et al., "A lymphotropic prodrug of L-dopa: synthesis, pharmacological properties and pharmacokinetic behavior of 1,3-dihexadecanoyl-2-[(S)-2-amino-3-(3,4-dihydroxyphenyl)propanoyl]propane-1,2,3-triol," Journal of Medicinal Chemistry, vol. 29, No. 5, 1986 (pp. 687-669).

(56) References Cited

OTHER PUBLICATIONS

Garzon-Aburbeh el al., "1,3-Dipalmitoylglycerol ester of chlorambucil as a lymphotropic, orally administrable antineoplastic agent," Journal of Medicinal Chemistry, vol. 26, No. 8, 1983 (pp. 1200-1203).
Gossauer et al., "Synthesen von Gallenfarbstoffen, V. Stereospezifische Totalsynthesen diastereomerer Mesobilirhodine und Isomesobilirhodine," European Journal of Organic Chemistry, vol. 1977, No. 4, 1977 (pp. 664-686).
Han et al., "Targeted delivery of a model immunomodulator to the lymphatic system: comparison of alkyl ester versus triglyceride mimetic lipid prodrug strategies," Journal of Controlled Release, vol. 177, 2014 (pp. 1-10).
Han et al., "Lymphatic Transport and Lymphocyte Targeting of a Triglyceride Mimetic Prodrug is Enhanced in a Large Animal Model: Studies in Greyhound Dogs," Molecular Pharmaceutics, vol. 13, No. 10, 2016 (pp. 3351-3361).
Hu et al., "Glyceride-Mimetic Prodrugs Incorporating Self-Immolative Spacers Promote Lymphatic Transport, Avoid First-Pass Metabolism, and Enhance Oral Bioavailability," Angewandte Chemie International Edition, vol. 55, No. 44, 2016 (pp. 13700-13705); Supplementary Information (pp. 1-43).
Huvelle et al., "Syntheses and kinetic studies of cyclisation-based self-immolative spacers," Organic and Biomolecular Chemistry, vol. 15, 2017 (pp. 3435-3443).
International Search Report and Written Opinion issued by the Australian Patent Office as International Searching Authority for International Patent Application No. PCT/AU2015/050460, dated Oct. 15, 2015 (10 pages).
International Search Report and Written Opinion issued by the Australian Patent Office as International Searching Authority for International Patent Application No. PCT/AU2016/050845, dated Oct. 27, 2016 (12 pages).
International Search Report and Written Opinion issued by the United States Patent and Trademark Office as International Searching Authority for International Patent Application No. PCT/US2018/048642, dated Dec. 11, 2018 (10 pages).
Janossy et al., "Lymphocyte activation: I. Response of T and B lymphocytes to phytomitogens," Clinical & Experimental Immunology vol. 9, No. 4, 1971 (pp. 483-498).
Jew et al., "Asymmetric synthesis of (R)-(+)-etomoxir," Tetrahedron: Asymmetry, vol. 8, No. 8, 1997 (pp. 1187-1192).
Jewett et al., "Rapid Cu-Free Click Chemistry with Readily Synthesized Biarylazacyclooctynones," Journal of the American Chemical Society, vol. 132, No. 11, 2010 (pp. 3688-3690).
Kai et al., "Structure-activity relationship study of flowering-inducer FN against Lemna paucicostata," Tetrahedron, vol. 64, No. 28, 2008 (pp. 6760-6769).
Kim et al., "Convenient Synthesis of Electron Deficient Dienes via Pd(0) Catalyzed Coupling," Synlett, vol. 10, 1988 (pp. 1059-1060).
Kratz et al., "Prodrug strategies in anticancer chemotherapy," ChemMedChem, vol. 3, No. 1, 2008 (pp. 20-53).
Levine et al., "Trimethyl lock: a trigger for molecular release in chemistry, biology, and pharmacology," Chemical Science, No. 8, 2012 (pp. 2412-2420).
Lienard et al., "Structural basis for the broad-spectrum inhibition of metallo-beta-lactamases by thiols," Organic and Biomolecular Chemistry, vol. 6, No. 13, 2008 (pp. 2282-2294).
Louiseau et al. "Lymphotropic antifilarial agents derived from Closantel and Cholorambucil," International Journal for Parasitology, vol. 27, 1997 (pp. 443-447).
Mergen et al., "Antiepileptic activity of 1,3-dihexadecanoylamino-2-valproyl-propan-2-ol, a prodrug of valproic acid endowed with a tropism for the central nervous system," Journal of Pharmacy and Pharmacology, vol. 43, No. 11, 1991 (pp. 815-816).
Paris et al., "Glycerides as Prodrugs. 1. Synthesis and anti-inflammatory activity of 1,3-bis(alkanoyl)-2-(O-acetylsalicyloyl)glycerides (aspirin triglycerides)," Journal of Medicinal Chemistry, vol. 22, No. 6, 1979 (pp. 683-687).

Paris et al., "Glycerides as Prodrugs. 2. 1,3 Dialkanoyl1-2-(2-methyl-4-oxo-1,3-benzodioxan-2-yl) glycerides (Cyclic Aspirin Triglycerides) as Anti-inflammatory Agents," Journal of Medicinal Chemistry, 1980, vol. 23, No. 1, 1980 (pp. 79-82).
Paris et al., "Glycerides as Prodrugs. 3. Synthesis and Anti-inflammatory Activity of [10(p-Chlorobenzoyl)-5-methoxy-2-methylindole-3-acetyl]gycertides (Indomethacin Glycerides)," Journal of Medicinal Chemistry, vol. 23, No. 1, 1980 (pp. 9-13).
Pouton, C.W., "Formulation of poorly water-soluble drugs for oral administration: physicochemical and physiological issues and the lipid formulation classification system," European Journal of Pharmaceutical Sciences, vol. 29, Nos. 3-4, 2006 (pp. 278-287).
Pouton, C. W., "Lipid formulations for oral administration of drugs: non-emulsifying, self-emulsifying and 'self-microemulsifying' drug delivery systems," European Journal of Pharmaceutical Sciences, vol. 11, supp. 2, 2000 (pp. S93-S98).
Silverman, R. B., "Chapter 8—Prodrugs and Drug Delivery Systems" in The Organic Chemistry of Drug Design and Drug Action (Second Edition), 2004 (pp. 497-557, 520-525).
Silverman, R. B., "Chapter 9—Prodrugs and Drug Delivery Systems" in The Organic Chemistry of Drug Design and Drug Action (Third Edition), 2014 (pp. 423-468).
Subba Reddy el al., "A Concise and Convergent Total Synthesis of Two Novel Cytotoxic Hydroquinones, Lanneaquinol and (R)-2'-Hydroxylanneaquinol," Helvetica Chimica Acta, vol. 96, No. 10, 2013 (pp. 1983-1990).
Sugihara et al., "Studies on intestinal lymphatic absorption of drugs. I. Lymphatic absorption of alkyl ester derivatives and alpha-monoglyceride derivatives of drugs," Journal of Pharmacobio-Dynamics, vol. 11, No. 5, 1988 (pp. 369-376).
Sugihara et al., "Studies on intestinal lymphatic absorption of drugs. II. Glyceride prodrugs for improving lymphatic absorption of naproxen and nicotinic-acid," Journal of Pharmacobio-Dynamics, vol. 11, No. 8, 1988 (pp. 555-562).
Takagi et al., "The synthesis of enantiomerically pure novel liquid crystal compounds containing the bis(trifluoromethyl)alkanediol moiety," Tetrahedron: Asymmetry, vol. 15, No. 17, 2004 (pp. 2591-2594).
Trevaskis et al., "Bile increases intestinal lymphatic drug transport in the fasted rat," Pharmaceutical Research, vol. 22, No. 11, 2005 (pp. 1863-1870).
U.S. Appl. No. 16/209,600, filed Dec. 4, 2018 (143 pages).
Warren et al., "Evaluation of the Structural Determinants of Polymeric Precipitation Inhibitors Using Solvent Shift Methods and Principle Component Analysis," Molecular Pharmaceutics, vol. 10, No. 8, 2013 (pp. 2823-2848).
Wittman et al., "Synthesis and antitumor activity of novel paclitaxel-chlorambucil hybrids," Bioorganic and Medicinal Chemistry Letters, vol. 11, No. 6, 2001 (pp. 811-814).
Wolbers et al., "Viability study of HL60 cells in contact with commonly used microchip materials," Electrophoresis, vol. 27, No. 24, 2006 (pp. 5073-5080).
Young et al., "Total Synthesis of (+)-Nakadomarin A," Journal of the American Chemical Society, vol. 129, No. 5, 2007 (pp. 1465-1469).
Zgair et al., "Oral administration of cannabis with lipids leads to high levels of cannabinoids in the intestinal lymphatic system and prominent immunomodulation," Scientific Reports 7, Article No. 14542, 2017 (pp. 1-12).
Bourgeois et al., "Application of thermal analysis to the study of lipidic prodrug incorporation into nanocarriers,"*Journal of Thermal Analysis and Calorimetry*, 98: 65-71 (2009).
Scriba et al., "Bioavailability of Phenytoin Following Oral Administration of Phenytoin-lipid Conjugates to Rats," *J. Pharm. Pharmacol.*, 47: 945-948 (1995).
Scriba, "Synthesis and in Vitro Degradation of Testosterone-Lipid Conjugates," *Archiv der Pharmazie—Chemistry in Life Sciences*, 328: 271-276 (1995).
Skanji et al., "A new nanomedicine based on didanosine glycerolipidic prodrug enhances the long term accumulation of drug in a HIV sanctuary," *International Journal of Pharmaceutics*, 414: 285-297 (2011).

(56) References Cited

OTHER PUBLICATIONS

Takada et al., "Conversion of a Novel 5-fluorouracil (5-FU) Derivative to 5-FU in Rats," *Research Communications in Chemical Pathology and Pharmacology*, 40(1): 99-108 (Apr. 1983).
Pond, S. M. et al., "First-Pass Elimination, Basic Concepts and Clinical Consequences," (Pond and Tozer, Clinical Pharmacokinetics 9:1-25 (1984)).
D'yakova et al., "Lymphotropic prodrugs based on 2',3'-didehydro-3'-deoxythymidine. Synthesis and sensitivity to hydrolysis," Russian Journal of Bioorganic Chemistry. 2011;47(10):1588-1593.
Shastina et al., "Synthesis, properties, and Anti-HIV activity of new lipophilic 3'-azido-3'-deoxythymidine conjugates containing functional phosphoric linkages," Russian Journal of Bioorganic Chemistry. 2013;39:161-169.
Amory et al., "Oral testosterone-triglyceride conjugate in rabbits: single-dose pharmacokinetics and comparison with oral testosterone undecanoate," J. Androl. 2003;24(5):716-20.
Andréen et al., "Sex steroid induced negative mood may be explained by the paradoxical effect mediated by GABAA modulators," Psychoneuroendocrinology. 2009;34(8):1121-32.
Wirtz et al., "Chemically induced mouse models of acute and chronic intestinal inflammation," Nat. Protoc. 2017;12(7):1295-1309.
Bitran et al., "Anxiolytic effect of progesterone is mediated by the neurosteroid allopregnanolone at brain GABAA receptors," J. Neuroendocrinol. 1995;7(3):171-7.
Braile-Fabris et al., "Controlled clinical trial of IV cyclophosphamide versus IV methylprednisolone in severe neurological manifestations in systemic lupus erythematosus," Ann. Rheum. Dis. 2005;64(4):620-25.
Brand et al., "Collagen-induced arthritis," Nat. Protoc. 2007;2(5):1269-75.
Codelli et al., "Second-Generation Difluorinated Cyclooctynes for Copper-Free Click Chemistry," J. Am. Chem. Soc. 2008; 130(34):11486-11493.
Coutinho and Chapman, "The anti-inflamatory and immunosuppressive effects of glucocorticoids, recent developments and mechanistic insights," Mol. Cell. Endocrinol. 2011;335(1):2-13.
DeWolf and Sykes, "Alloimmune T cells in transplantation ," J. Clin. Invest. 2017;127(7):2473-2481.
Freitag et al., "Gliadin-primed CD4+CD45RBlowCD25-T cells drive gluten-dependent small intestinal damage after adoptive transfer into lymphopenic mice," Gut. 2009;58(12):1597-605.
Frye and Duncan, "Progesterone metabolites, effective at the GABAA receptor complex, attenuate pain sensitivity in rats," Brain Res. 1994:643(1-2):194-203.
Frye and Walf, "Changes in progesterone metabolites in the hippocampus can modulate open field and forced swim test behavior of proestrous rats," Horm. Behav. 2002;41(3):306-15.
Goodin, "Glucocorticoid treatment of multiple sclerosis," Handb. Clin. Neurol. 2014;122:455-64.
Grainge et al., "Case series reporting the effectiveness of mycophenolate mofetil in treatment-resistant asthma," Eur. Respir. J. 2013;42(4):1134-7.
Griffin et al., "Niemann-Pick type C disease involves disrupted neurosteroidogenesis and responds to allopregnanolone," Nat. Med. 2004;10(7):704-11.
Guo et al., "Rheumatoid arthritis: pathological mechanisms and modern pharmacologic therapies," Bone Res. 2018,6:15.
Gupta et al., "Dexamethasone cyclophosphamide pulse therapy in systemic lupus erythematosus: a case report," J. Dermatolg. Treat. 2009;20(1):55-8.
Irwin and Diaz Brinton, "Allopregnanolone as regenerative therapeutic for Alzheimer's disease: translational development and clinical promise," Prog. Neurobiol. 2014;113:40-55.
Irwin et al., "Frontiers in therapeutic development of allopregnanolone for Alzheimer's disease and other neurological disorders," Front. Cell. Neurosci. 2014;8:203.

Iwaszkiewicz-Grzes et al., "Synthesis and biological activity of mycophenolic acid-amino acid derivatives," Eur. J. Med. Chem. 2013;69:863-71.
Jeong et al., "Dose optimization of tacrolimus for improving survival time of PEGylated islets in a rat-to-mouse xenograft model," Macromolecular Research. 2016;24(12):1047-1054.
Kanes et al., "Brexanolone (SAGE-547 injection) in post-partum depression: a randomised controlled trial," Lancet. 2017;390(10093):480-489.
Kim et al., "The Anti-Inflammatory Effects of Oral-Formulated Tacrolimus in Mice with Experimental Autoimmune Encephalomyelitis," J. Korean Med. Sci. 2017;32(9):1502-1507.
Koboziev et al., "Gut-associated lymphoid tissue, T cell trafficking, and chronic intestinal inflammation," Ann. NY. Acad. Sci. 2010;1207(Suppl 1):E86-E93.
Li et al., "Mycophenolate mofetil or tacrolimus compared with intravenous cyclophosphamide in the induction treatment for active lupus nephritis," Nephrol. Dial. Transplant. 2012;27(4):1467-72.
Ling and Luster, "Allergen-Specific CD4+ T Cells in Human Asthma," Ann. Am. Thorac. Soc. 2016;13(Suppl 1):S25-S30.
Ling et al., C1q restrains autoimmunity and viral infection by regulating CD8+ T cell metabolism; Science. May 4, 2018;360(6388):558-563.
Lonshakov et al., "Synthesis and properties of 3?-azido-3?-deoxythymidine derivatives of glycerolipids," Pharm. Chem. J. 2011;44(10):557-563.
Lui et al., "Effect of mycophenolate mofetil on severity of nephritis and nitric oxide production in lupus-prone MRL/lpr mice," Lupus. 2002;11(7):411-8.
Lv et al., "Mycophenolate Mofetil Modulates Differentiation of Th1/Th2 and the Secretion of Cytokines in an Active Crohn's Disease Mouse Model," Int. J. Mol. Sci. 2015;16(11):26654-66.
Maria and Davidson, "Emerging areas for therapeutic discovery in SLE," Curr. Opin. Immunol. 2018;55:1-8.
Mattarei et al., "Novel lipid-mimetic prodrugs delivering active compounds to adipose tissue," Eur. J. Med. Chem. 2017;135:77-88.
Meliambro et al., "Therapy for Proliferative Lupus Nephritis," Rheum. Dis. Clin. North Am. 2018;44(4):545-560.
Michel et al., "Mycophenolate mofetil in multiple sclerosis: a multicentre retrospective study on 344 patients," J. Neurol. Neurosurg. Psychiatry. 2014;85(3):279-83.
Miller and Karpus, "Experimental autoimmune encephalomyelitis in the mouse," Curr. Protoc. Immunol. 2007;Chapter 15:Unit 15.1.
Minard-Colin et al., "Lymphoma depletion during CD20 immunotherapy in mice is mediated by macrophage Fc?RI, Fc?RIII, and Fc?RIV," Blood. 2008;112(4):1205-1213.
Miyamoto et al., "A novel prodrug strategy for extremely hydrophobic agents: conjugation to symmetrically branched glycerol trimer improves pharmacological and pharmacokinetic properties of fenofibrate," Mol. Pharm. 2013;10(7):2723-9.
Mok, "Mycophenolate mofetil for lupus nephritis: an update," Expert Rev. Clin. Immunol. 2015;11(12):1353-64.
Nakajima, et al., "Effectiveness of tacrolimus in comparison with methotrexate or biologies in propensity score-matched patients with rheumatoid arthritis," Mod. Rheumatol. 2016;26(6):836-843.
Nash et al., "Phase 3 study comparing methotrexate and tacrolimus with methotrexate and cyclosporine for prophylaxis of acute graft-versus-host disease after marrow transplantation from unrelated donors," Blood. 2000;96:2062-2068.
Negi and Das, "CNS: Not an immunoprivilaged site anymore but a virtual secondary lymphoid organ," Int. Rev.Immunol. 2018;37(1):57-68.
Ning et al., "Visualizing metabolically labeled glycoconjugates of living cells by copper-free and fast huisgen cycloadditions," Angew. Chem. Int. Ed. Engl. 2008; 47(12):2253-5.
Okayama et al., "Mast cells are involved in the pathogenesis of indomethacin-induced rat enteritis," J. Gastroenterol. 2009;44(Suppl 19):35-9.
Osborne et al., "Lower allopregnanolone during pregnancy predicts postpartum depression: An exploratory study," Psychoneuroendocrinology. 2017;79:116-121.
Pallet et al., "Impact of Immunosuppressive Drugs on the Metabolism of T Cells ," Int. Rev. Cell. Mol. Biol. 2018;341:169-200.

(56) References Cited

OTHER PUBLICATIONS

PCT International Search Report and Written Opinion from PCT/US2018/066580 dated Apr. 24, 2019.
PCT International Search Report and Written Opinion from PCT/US2018/066585 dated Apr. 30, 2019.
PCT International Search Report and Written Opinion from PCT/US2019/044877 dated Oct. 24, 2019.
PCT International Search Report and Written Opinion from PCT/US2020/020387 dated Jun. 24, 2020.
PCT International Search Report and Written Opinion from PCT/US2020/020398 dated Jul. 20, 2020.
PCT International Search Report and Written Opinion from PCT/US2020/020433 dated Jun. 26, 2020.
Perché et al., "Prenatal testosterone treatment potentiates the aggression? inhibiting effect of the neurosteroid dehydroepiandrosterone in female mice," Agress. Behav. 2001;27(2):130-8.
Pesu et al., "Jak3, severe combined immunodeficiency, and a new class of immunosuppressive drugs," Immunol. Rev. 2005;203:127-42.
Pie et al., "Natural killer cells accumulate in lung-draining lymph nodes and regulate airway eosinophilia in a murine model of asthma," Scand. J. Immunol. 2010;72(2):118-27.
Powell et al., "The immunomodulatory drugs cyclosporin A, mycophenolate mofetil, and sirolimus (rapamycin) inhibit allergen-induced proliferation and IL-5 production by PBMCs from atopic asthmatic patients," 2001;108(6):915-7.
Pubmed Compound Summary for CID 132121512, '1-O-[3R,5S,8S,9S,10S,13S,14S,17S)-17-Acetyl-10,13-dimethyl-11-oxo-1,2,3,4,5,6,7,8,9,12,14,15,16,17-tetradecahydrocyclopenta[a]phenanthren-3-yl] 3-O-[1,3-di(hexadecanoyloxy)propan-2-yl]propanedioate', U.S. National Library of Medicine, Jan. 29, 2018 (https://pubchem.ncbi.nlm.nih.gov/compound/132131512).
Renna et al., "Optimization of the treatment with immunosuppressants and biologies in inflammatory bowel disease," World J. Gastroenterol. 2014;20(29):9675-9690.
Rodriguez-Lago et al., "Previous exposure to biologies and C-reactive protein are associated with the response to tacrolimus in inflammatory bowel disease," Rev. Esp. Enferm. Dig. 2016;108(9):550-7.
Rogawski et al., "Neuroactive steroids for the treatment of status epilepticus," Epilepsia. 2013;54(Suppl 6):93-8.
Rupprecht, "Neuroactive steroids: mechanisms of action and neuropsychopharmacological properties," Psychoneuroendocrinology. 2003;20(2):139-68.
Sagiv-Barfi et al., "Ibrutinib enhances the antitumor immune response induced by intratumoral injection of a TLR9 ligand in mouse lymphoma," Blood. 2015;125(13):2079-86.
Schüle et al., "The role of allopregnanolone in depression and anxiety," Prog. Neurobiol. 2014;113:79-87.
Siebert et al., "New Analogues of Mycophenolic Acid," Mini Rev. Med. Chem. 2017;17(9):734-745.
Smith and Cooper, "Mycophenolate mofetil therapy in the management of inflammatory bowel disease—a retrospective case series and review," J. Crohns Colitis. 2014;8(8):890-7.
Smith et al., "Modular assembly of macrocyclic organo-peptide hybrids using synthetic and genetically encoded precursors," Angew. Chem. Int. Ed. Engl. 2011;50(22):5075-80.
Stadnyk et al., "Neutrophil migration into indomethacin induced rat small intestinal injury is CD11a/CD18 and CD11b/CD18 co-dependent," Gut. 2002;50(5):629-635.
Stump et al., "Lymphatic Changes in Respiratory Diseases: More than Just Remodeling of the Lung?" Am. J. Respir. Cell Mol. Biol. 2017;57(3):272-279.
Tan and Lawrence, "Use of mycophenolate mofetil in inflammatory bowel disease," World J. Gastroenterol. 2009;15(13):1594-1599.
Tanaka et al., "Structure of FK506, a novel immunosuppressant isolated from Streptomyces," J. Am. Chem. Soc. 1987;109(16):5031-5033.
Taniguchi et al., "A Case of Severe Bronchial Asthma Controlled with Tacrolimus," J. Allergy (Cairo). 2011;201:479129.
Taylor and Ryan, "Understanding mechanisms of hypertension in systemic lupus erythematosus," Ther. Adv. Cardiovasc. Dis. 2017;11(1):20-32.
Tohda et al., "Establishment of a novel B-cell lymphoma cell line with suppressed growth by gamma-secretase inhibitors," Leuk. Res. 2006;30(11):1385-90.
Trevaskis et al., "From sewer to saviour—targeting the lymphatic system to promote drug exposure and activity," Nature Review Drug Discovery. 2015;14:781-803.
Van Bruggen et al., "Attenuation of murine lupus nephritis by mycophenolate mofetil," J. Am. Soc. Nephrol. 1998;9(8):1407-15.
Van Dieren et al., "Local application of tacrolimus in distal colitis: feasible and safe," Inflamm. Bowel Dis. 2009;15(2):193-8.
Wagner et al., "Selective epimerization and skeletal resection in the ascomycin framework: A study of the biological consequences of lactam rotamer selection," Tetrahedron. 1996;52(29):9643-9654.
Weyand and Goronzy, "Immunometabolism in early and late stages of rheumatoid arthritis," Nat. Rev. Rheumatol. 2017;13(5):291-301.
Wiebe and Kavaliers, "Analgesic effects of the putative FSH-suppressing gonadal steroid, 3 alpha-hydroxy-4-pregnen-20-one: possible modes of action," Brain Res. 1988;461(1):150-7.
Cammack et al., "substituent." Oxford Dictionary Biochemistry and Molecular Biology Revised Edition (2000). Oxford University Press.
Daintith, "substituent." Oxford Dictionary of Chemistry 6th Edition (2008). Oxford University Press.
IUPAC, Commission on Nomenclature of Organic Chemistry. A Guide to IUPAC Nomenclature of Organic Compounds (Recommendations 1993), 1993, Blackwell Scientific publications, Copyright 1993 IUPAC; Downloaded May 6, 2020 from https://www.acdlabs.com/iupac/nomenclature/93/r93_125.htm.
IUPAC, Compendium of Chemical Terminology, 2nd ed. (the "Gold Book"). Compiled by A. D. McNaught and A. Wilkinson. Blackwell Scientific Publications, Oxford (1997). Online version (2019) created by S. J. Chalk. ISBN 0-9678550-9-8. https://doi.org/10.1351/goldbook; Downloaded May 5, 2020.
Wikipedia contributors. (Feb. 11, 2015). Substitution reaction. In Wikipedia, The Free Encyclopedia. Archived May 9, 2015, 8:42:39, at https://web.archive.org/web/20150509084239/https://en.wikipedia.org/wiki/Substitution_reaction.
Hsieh, P.-S. et al., "Selective COX2 inhibition improves whole body and muscular insulin resistance in fructose-fed rats", European Journal of Clinical Investigation, vol. 38(11):812-819 (2008).
Nieschlag, E. et al., "Testosterone replacement therapy: current trends and future directions", Human Reproduction Update, vol. 10(5):409-419 (2004).

\* cited by examiner

LYMPH DIRECTING PRODRUGS

FIELD OF THE INVENTION

The present invention relates to compounds in the form of prodrugs, in particular, compounds that promote transport of a pharmaceutical agent to the lymphatic system and subsequently enhance release of the parent drug.

BACKGROUND OF THE INVENTION

The lymphatic system consists of a specialised network of vessels, nodes and lymphoid tissues that are distributed throughout the body in close proximity to the vascular system. The lymphatic system plays a number of key roles in immune response, fluid balance, nutrient absorption, lipid homeostasis, and tumour metastasis. Due to the unique anatomical and physiological characteristics of the lymphatic system, targeted drug delivery to and through the lymphatic system has been suggested as a means to improve both pharmacokinetic and pharmacodynamic profiles. Lymphatic drug transport has the potential to enhance oral bioavailability through avoidance of first pass metabolism, to alter systemic drug disposition, and to enhance efficacy against lymph or lymphocyte mediated pathologies such as lymphoma, leukemia, lymphatic tumour metastasis, autoimmune disease, lymph resident infections and transplant rejection.

In order for drugs to access the intestinal lymph, they must first associate with intestinal lymph lipoproteins that are assembled in intestinal absorptive cells (enterocytes) in response to lipid absorption. Association with these lipoproteins subsequently promotes drug transport into the lymph since their size precludes ready diffusion across the vascular endothelium lining the blood capillaries that drain the small intestine. Instead, these large colloidal structures enter the lymphatic capillaries since the lymphatic endothelium is considerably more permeable than that of the vascular endothelium. Historically, drugs with high lymphatic transport have been highly lipophilic in order to promote physical association with lipoproteins (usually, but not exclusively, log D>5 and solubility in long chain triglyceride of >50 mg/g). Therefore, highly lipophilic analogues of drugs have been envisaged as one way to promote lymphatic drug transport. However, chemical modification of a parent drug can result in a reduction in potency and in many cases, significant increases in lipophilicity have been correlated with increases in toxicity.

Compounds in the form of lipophilic prodrugs provide a means to temporarily increase lipophilicity and lipoprotein affinity of a pharmaceutical compound, thereby increasing lymphatic targeting. Having been transported via the lymphatic system, the prodrug ultimately reverts to the parent drug in order to be active at its target site.

There have been several studies to explore the potential for simple aliphatic esters of drugs to be used as lymph directing prodrugs. Testosterone undecanoate provides one example of a marketed compound for which this approach has been taken. After oral administration, testosterone is almost entirely metabolised on its first pass through the liver, and consequently, it has minimal bioavailability. The undecanoate ester of testosterone redirects a small proportion of the absorbed dose into the lymphatic system, thereby avoiding hepatic first pass metabolism and increasing the oral bioavailability of testosterone. However, this process is still very inefficient, and the bioavailability of testosterone after oral administration of the undecanoate ester is thought to be <5%.

Another mechanism of promoting lymphatic drug transport is to employ prodrugs that incorporate into endogenous pathways associated with the absorption, transport and disposition of dietary lipids. One example of a dietary lipid utilised as a prodrug is triglyceride. Examples of drug-lipid conjugates have been documented in a number of previous publications where the parent drug contains an available carboxylic acid group and has been directly conjugated to a glyceride backbone (Paris, G. Y. et al., J. Med. Chem. 1979, 22, (6), 683-687; Garzon Aburbeh, A. et al., J. Med. Chem. 1983, 26, (8), 1200-1203; Deverre, J. R.; et al., J. Pharm. Pharmacol. 1989, 41, (3), 191-193; Mergen, F. et al., J. Pharm. Pharmacol. 1991, 43, (11), 815-816; Garzon Aburbeh, A. et al., J. Med. Chem. 1986, 29, (5), 687-69; and Han, S. et al. J Control. Release 2014, 177, 1-10).

In other examples, a short linker has been used to facilitate drug-triglyceride conjugation where the drug does not contain an available carboxylic acid (Scriba, G. K. E., Arch. Pharm. (Weinheim). 1995, 328, (3), 271-276; and Scriba, G. K. E. et al., J. Pharm. Pharmacol. 1995, 47, (11), 945-948). These drug-lipid conjugates employ succinic acid to facilitate conjugation to an available hydroxyl functionality. However, the literature teaches that this structure is not at all useful, for example, Scriba examined the in vitro hydrolysis of a testosterone-succinic acid-glyceride lipid conjugate and concluded that "testosterone is released only very slowly from the prodrugs by chemical, plasma esterase-catalysed and lipase-mediated hydrolysis in the present study . . . . Thus, testosterone conjugates appear to be poor prodrugs for the delivery of the steroid."

Others have employed an ether linkage to the glyceride, and an ester linkage to the drug (Sugihara, J. et al., J. Pharmacobiodyn. 1988, 11, (5), 369-376; and Sugihara, J. et al., J. Pharmacobiodyn. 1988, 11, (8), 555-562). The authors of these articles state explicitly that the ether bond between glycerol and an n-alkyl chain, and the ester bond between an n-alkyl chain and a drug seem to be necessary for chemical modification of drugs. However, the present inventors have found that an ether linkage is, in fact, counterproductive and does not allow significant lymphatic transport.

Accordingly, there exists a need to develop novel lipid-pharmaceutical agent conjugates that facilitate stable transport of the pharmaceutical agent to the intestinal lymph and that readily revert to the parent agent in order to be active.

SUMMARY OF THE INVENTION

It has now been found that the use of certain "linkers" to join the pharmaceutical agent to the triglyceride unit provide optimal pharmacokinetic profiles for the resultant lipid-pharmaceutical agent conjugate.

Accordingly, in one aspect the present invention provides a compound of the formula (I):

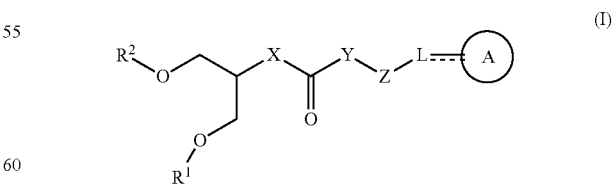

wherein
$R^1$ and $R^2$ independently represent H, or a residue of a $C_2$-$C_{28}$ fatty acid;
—X— is selected from —O—, —NH— and —S—;
—Y— represents an optionally substituted —$C_3$-$C_{20}$alkyl-, —$C_3$-$C_{20}$alkenyl- or —$C_3$-$C_{20}$alkynyl- group, wherein one or more of the carbon atoms in the alkyl, alkenyl or alkynyl group may be replaced with NH, S, O, a $C_5$-$C_8$ aromatic or aliphatic cyclic group or a $C_5$-$C_8$ aromatic or aliphatic heterocyclic group, provided that the alkyl, alkenyl or alkynyl group does not exceed a length equivalent to a linear $C_{20}$alkyl group;

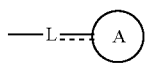

represents a residue of a pharmaceutical agent;
—L— is —X'— or —X'C(O)—;
X' is O, S, N, N($R^4$) or S(O)$_2$NH;
═══ represents a single bond when X' is O, S, N($R^4$) or S(O)$_2$NH; or
═══ represents two separate bonds when X' is N;
—Z— is —C(O)— or —C(O)$R^3$— when —L— is —X'—; or
—Z— is absent when —L— is —X'C(O)—;
$R^3$ is a self-immolative group; and
$R^4$ is H or $C_1$-$C_4$alkyl; or
pharmaceutically acceptable salts thereof.

In another aspect, the present invention provides a compound of the formula (I) represented by the formula (II):

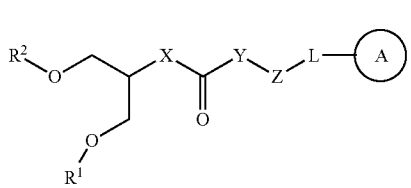

(II)

wherein
$R^1$ and $R^2$ independently represent H, or a residue of a $C_2$-$C_{28}$ fatty acid;
—X— is selected from —O—, —NH— and —S—;
—Y— represents an optionally substituted —$C_3$-$C_{20}$alkyl-, —$C_3$-$C_{20}$alkenyl- or —$C_3$-$C_{20}$alkynyl- group, wherein one or more of the carbon atoms in the alkyl, alkenyl or alkynyl group may be replaced with NH, S, O, a $C_5$-$C_8$ aromatic or aliphatic cyclic group or a $C_5$-$C_8$ aromatic or aliphatic heterocyclic group, provided that the alkyl, alkenyl or alkynyl group does not exceed a length equivalent to a linear $C_{20}$alkyl group;

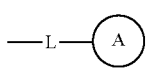

represents a residue of a pharmaceutical agent;
—L— is —X'— or —X'C(O)—;
X' is O, S or N($R^4$);
$R^4$ is H or $C_1$-$C_4$alkyl; and
—Z— is —C(O)— when —L— is —X'—; or
—Z— is absent when —L— is —X'C(O)—; or
pharmaceutically acceptable salts thereof.

In another aspect, the present invention provides a compound of formula (I) represented by the formula (III):

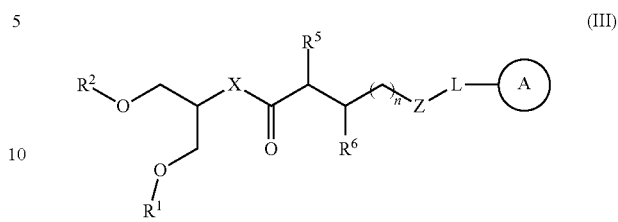

(III)

wherein
$R^1$, $R^2$, —X—,

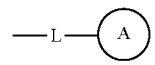

and —Z— are as defined for formula (I) or formula (II);
$R^5$ and $R^6$ are individually selected from hydrogen and $C_1$-$C_4$alkyl; and
n is from 1 to 18; or
pharmaceutically acceptable salts thereof.

In a further aspect the present invention provides a compound of formula (I) represented by the formula (IV):

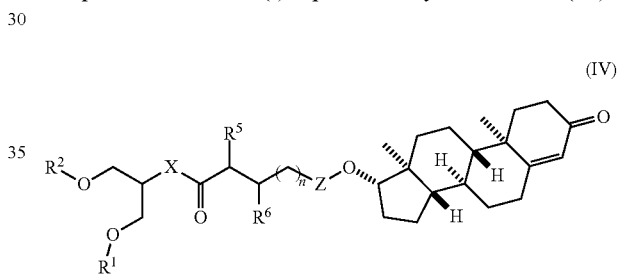

(IV)

wherein $R^1$, $R^2$ and X are as defined for formula (I);
$R^5$ and $R^6$ are individually selected from hydrogen and $C_1$-$C_4$alkyl;
—Z— is —C(O)— or —C(O)$R^3$—;
$R^3$ is a self-immolative group; and
n is from 1 to 18; or
pharmaceutically acceptable salts thereof.

In yet a further aspect the present invention provides a compound of formula (I) represented by the formula (V):

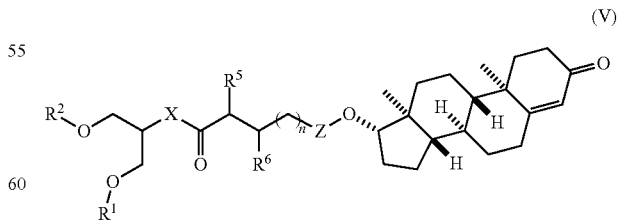

(V)

wherein $R^1$, $R^2$, X, $R^5$, $R^6$ and n are as defined for formula (IV); and
—Z— is —C(O)—; or
pharmaceutically acceptable salts thereof.

In another aspect, the present invention provides a method of treating or preventing a disease or disorder in which increased testosterone levels are beneficial, comprising administering to the subject in need thereof a therapeutically effective amount of a compound of the formula (IV).

In a further aspect, the present invention provides the use of a compound of the formula (IV) in the manufacture of a medicament for the treatment or prevention of a disease or disorder in which increased testosterone levels are beneficial.

In another aspect, the present invention provides a compound of the formula (IV) for use in the treatment or prevention of a disease or disorder in which increased testosterone levels are beneficial.

In another aspect, the present invention provides a method of promoting lymphatic transport and systemic release of a pharmaceutical agent comprising conjugating to the pharmaceutical agent a prodrug residue of the formula (VI):

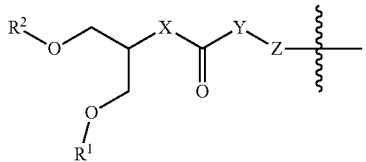

(VI)

wherein
$R^1$ and $R^2$ independently represent H or a residue of a $C_2$-$C_{28}$ fatty acid;
—X— is selected from —O—, —NH— and —S—;
—Y— represents an optionally substituted —$C_3$-$C_{20}$alkyl-, —$C_3$-$C_{20}$alkenyl- or —$C_3$-$C_{20}$alkynyl- group, wherein one or more of the carbon atoms in the alkyl, alkenyl or alkynyl group may be replaced with NH, S, O, a $C_5$-$C_8$ aromatic or aliphatic cyclic group, or a $C_5$-$C_8$ aromatic or aliphatic heterocyclic group, provided that the alkyl, alkenyl or alkynyl group does not exceed a length equivalent to a linear $C_{20}$alkyl group;
—Z— is —C(O)—, —C(O)$R^3$— or —$CH_2$—;
$R^3$ is a self-immolative group; and
~~~ denotes the point where the linker is conjugated to the pharmaceutically active agent; or
pharmaceutically acceptable salts thereof.

These and other aspects of the present invention will become more apparent to the skilled addressee upon reading the following detailed description in connection with the accompanying examples and claims.

DETAILED DESCRIPTION OF THE INVENTION

Figure 1:
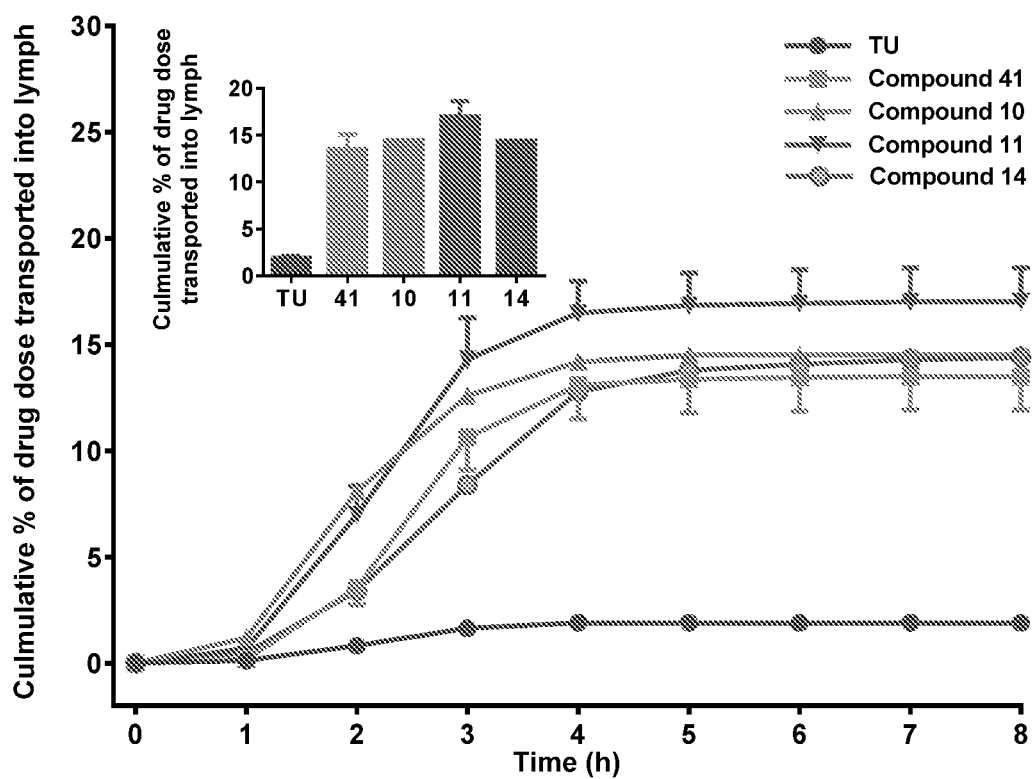
FIG. 1: Graphical representation of the cumulative lymphatic transport of total testosterone related derivatives (% of administered dose) versus time in anaesthetised, mesenteric lymph duct cannulated female SD rats following intraduodenal infusion of testosterone undecanoate (TU) and Compounds 10, 11, 14 and 41.

When prodrug strategies are employed in the field of drug development to improve pharmacokinetic properties, prodrugs are usually expected to revert to the parent compound via non-specific degradation or enzyme-mediated biotransformation, prior to exhibiting biological activity. The current invention discloses modified glyceride based compounds that are able to promote lymphatic transport of the pharmaceutical agent and improve reversion of the compound to the active pharmaceutical agent.

Dietary lipids, such as triglycerides use a unique metabolic pathway to gain access to the lymph (and ultimately the systemic circulation) that is entirely distinct from that of other nutrients such as proteins and carbohydrates. After ingestion, dietary triglycerides are hydrolysed by luminal lipases to release one monoglyceride and two fatty acids for each molecule of triglyceride. The monoglyceride and two fatty acids are subsequently absorbed into enterocytes, where they are re-esterified to triglycerides.

Resynthesised triglycerides are assembled into intestinal lipoproteins (primarily chylomicrons) and the chylomicrons so formed are exocytosed from enterocytes and subsequently gain preferential access to the intestinal lymphatics. Within the lymphatics, lipids in the form of chylomicrons, drain through a series of capillaries, nodes and ducts, finally emptying into the systemic circulation at the junction of the left subclavian vein and internal jugular vein. Following entry into blood circulation, triglycerides in chylomicrons are preferentially and efficiently taken up by tissues with high expression of lipoprotein lipases such as adipose tissue, the liver and potentially certain types of tumour tissues.

Lipid mimetic compounds are expected to behave similarly to natural triglycerides and to be transported to and through the lymphatic system before reaching the systemic circulation. In this way, the pharmacokinetic and pharmacodynamic profiles of the parent pharmaceutical agent may be manipulated to enhance access to the lymph and lymphoid tissues, thereby promoting oral bioavailability via avoidance of first pass metabolism (and potentially intestinal efflux). Lipid mimetic compounds may also promote drug-targeting to sites within the lymph, lymph nodes and lymphoid tissues, and to sites of high lipid utilization and lipoprotein lipase expression such as adipose tissue and some tumours.

Lipidated prodrugs that readily convert to parent drug after transport via the systemic circulation reduce free drug concentrations in the gastrointestinal (GI) tract, which may provide benefits in reducing gastrointestinal irritation, in taste masking, in promoting drug solubilisation in intestinal bile salt micelles (due to similarities to endogenous monoglycerides) and in enhancing passive membrane permeability (by increasing lipophilicity). Lipidated prodrugs also promote solubility in lipid vehicles comprising either lipids alone or mixtures of lipids with surfactants and/or cosolvents, and in doing so allow larger doses to be administered with the drug in solution than might be possible for parent drug.

The present inventors have surprisingly found that the portion of the drug-glyceride conjugate linking the pharmaceutical agent to the glyceride unit can be modified to improve stability of the drug-glyceride conjugate in the GI tract, promote transport to the intestinal lymph and ultimately, promote release of the pharmaceutical agent from the pharmaceutical agent-glyceride prodrug. Accordingly, by altering the "linker" joining the pharmaceutical agent to the glyceride unit, optimal pharmacokinetic profiles can be achieved for the resultant compound.

In this specification a number of terms are used which are well known to a skilled addressee. Nevertheless, for the purposes of clarity a number of terms will be defined.

In this specification, unless otherwise defined, the term "optionally substituted" is taken to mean that a group may or may not be further substituted with one or more groups selected from hydroxyl, alkyl, alkoxy, alkoxycarbonyl, alkenyl, alkenyloxy, alkynyl, alkynyloxy, amino, aminoacyl, thio, arylalkyl, arylalkoxy, aryl, aryloxy, acylamino, carboxy, cyano, halogen, nitro, sulfo, phosphono, phosphorylamino, phosphinyl, heteroaryl, heteroaryloxy, heterocyclyl, heterocycloxy, trihalomethyl, pentafluoroethyl, trifluoromethoxy, difluoromethoxy, trifluoromethanethio, trifluoroethenyl, mono- and di-alkylamino, mono- and di-(substituted alkyl)amino, mono- and di-arylamino, mono- and di-heteroarylamino, mono- and di-heterocyclyl, amino, and unsymmetric di-substituted amines having different substituents selected from alkyl, aryl, heteroaryl and heterocyclyl.

As used herein, the term "alkyl", used either alone or in compound words, denotes straight chain or branched alkyl. Prefixes such as "$C_2$-$C_{20}$" are used to denote the number of carbon atoms within the alkyl group (from 2 to 20 in this case). Examples of straight chain and branched alkyl include methyl, ethyl, n-propyl, isopropyl, n-butyl, sec-butyl, t-butyl, n-pentyl, hexyl, heptyl, 5-methylheptyl, 5-methylhexyl, octyl, nonyl, decyl, undecyl, dodecyl and docosyl ($C_{22}$).

As used herein, the term "alkenyl", used either alone or in compound words, denotes straight chain or branched hydrocarbon residues containing at least one carbon to carbon double bond including ethylenically mono-, di- or polyunsaturated alkyl groups as previously defined. Preferably the alkenyl group is a straight chain alkenyl group. Prefixes such as "$C_2$-$C_{20}$" are used to denote the number of carbon atoms within the alkenyl group (from 2 to 20 in this case). Examples of alkenyl include vinyl, allyl, 1-methylvinyl, butenyl, iso-butenyl, 3-methyl-2-butenyl, 1-pentenyl, 1-hexenyl, 3-hexenyl, 1-heptenyl, 3-heptenyl, 1-octenyl, 1-nonenyl, 2-nonenyl, 3-nonenyl, 1-decenyl, 3-decenyl, 1,3-butadienyl, 1,4-pentadienyl, 1,3-hexadienyl, 1,4-hexadienyl and 5-docosenyl ($C_{22}$).

As used herein, the term "alkynyl", used either alone or in compound words, denotes straight chain or branched hydrocarbon residues containing at least one carbon to carbon triple bond. Preferably the alkynyl group is a straight chain alkynyl group. Prefixes such as "$C_2$-$C_{20}$" are used to denote the number of carbon atoms within the alkenyl group (from 2 to 20 in this case).

As used herein, terms such as "heterocycle" or "heterocyclic group", used either alone or in compound words, denotes a saturated, partially unsaturated or fully unsaturated monocyclic, bicyclic or fused polycyclic ring systems containing at least one heteroatom selected from the group consisting of nitrogen, sulfur and oxygen. Prefixes such as "$C_5$-$C_8$" are used to denote the number of carbon atoms within the cyclic portion of the group (from 5 to 8 in this case). Examples of suitable heterocyclic substituents include, but are not limited to, pyrrole, furan, benzofuran, benzothiazole, imidazole, benzimidazole, imidazoline, pyrazole, pyrazoline, triazole, oxazole, oxazoline, isoxazole, isoxazoline, furazan, oxadiazole, piperidine, pyridine, pyrimidine, pyridazine and pyrazine, each of which may be further substituted with 1 to 3 substituents.

As used herein, terms such as "aryl" or "aromatic cyclic group" denotes any single- or polynuclear, conjugated or fused residues of aromatic hydrocarbon ring systems. Prefixes such as "$C_5$-$C_8$" are used to denote the number of carbon atoms within the cyclic portion of the aryl group (from 5 to 8 in this case). Examples of aryl include phenyl (single nuclear), naphthyl (fused polynuclear), biphenyl (conjugated polynuclear) and tetrahydronaphthyl (fused polynuclear).

As used here in, the term "linker" denotes the portion of the compound spanning from "X" to "L" for compounds of the formula (I) as described herein, joining the pharmaceutical agent to the glyceride unit.

As used herein, the term "self-immolative group" defines a chemical moiety that forms a scissile bond with the linker and a stable bond with the pharmaceutical agent, wherein the bond with the pharmaceutical agent becomes labile upon cleavage of the linker. Examples of self-immolative groups include, but are not limited to acetal self-immolative groups, para-hydroxybenzyl carbonyl self-immolative groups, flipped ester self-immolative groups and trimethyl lock self-immolative groups. A number of other suitable self-immolative groups are known in the art as described, for example, in Blencowe et al., Polym. Chem. 2011, 2, 773-790 and Kratz et al. Chem Med Chem. 2008, 3, 20-53. As used here in, the term "pharmaceutical agent" denotes any pharmaceutically active agent or imaging (contrasting) agent which would benefit from transport via the intestinal lymphatic system, for example, to avoid first pass metabolism or for targeted delivery within the lymphatic system.

Examples of suitable pharmaceutically active agents include, but are not limited to, testosterone, mycophenolic acid, oestrogens (estrogen), morphine, metoprolol, raloxifene, alphaxolone, statins such as atorvastatin, pentazocine, propranolol, L-DOPA, buprenorphine, midazolam, lidocaine, chlorpromazine, amitriptyline, nortriptyline, pentazocine, isosorbidedinitrate, glyceryl trinitrate, oxprenolol, labetalol, verapamil, salbutamol, epitiostanol, melphalan, lovastatin, non-steroidal anti-inflammatory medications (NSAIDS, such as aspirin, ibuprofen, naproxen), COX-2 inhibitors (such as celecoxib, rofecoxib), corticosteroid anti-inflammatory medications (such as prednisolone, prednisone, dexamethasone), anti-malarial medications (such as hydroxychloroquine), cyclophosphamide, nitrosoureas, platinum, methotrexate, azathioprine, mercaptopurine, fluorouracil, dactinomycin, anthracyclines (such as daunarubicin), mitomycin C, bleomycin, mithramycin, drugs acting on immunophilins (such as ciclosporin, tacrolimus, sirolimus), sulfasalazine, leflunomide, mycophenolate, opioids, fingolimod, myriocin, chlorambucil, doxorubicin, nelarabine, cortisone, dexamethasone, prednisone, pralatrexate, vinblastine, bortezomib, thiotepa, nelarabine, daunorubicin hydrochloride, clofarabine, cytarabine, dasatinib, imatinibmesylate, ponatinib hydrochloride, vincristine sulfate, bendamustine hydrochloride, fludarabine phosphate, bosutinib, nilotinib, omacetaxinemepesuccinate, anastrozole, capecitabine, letrozole, paclitaxel, gemcitabine, fulvestrant, tamoxifen, lapatinib, toremifene, ixabepilone, eribulin, albendazole, ivermectin, diethylcarbamazine, albendazole, doxycycline, closantel, maraviroc, enfuvirtide, deoxythymidine, zidovudine, stavudine, didanosine, zalcitabine, abacavir, lamivudine, emtricitabine, tenofovir, nevirapine, delavirdine, efavirenz, rilpivirine, raltegravir, elvitegravir, lopinavir, indinavir, nelfinavir, amprenavir, ritonavir, acyclovir and pharmaceutically active peptides.

Examples of suitable imaging agents include, but are not limited to, fluorophores such as the Alexa Fluor series of optical imaging probes for fluorescence microscopy or where the fluorophore has emission spectra in the infra-red range, for in vivo imaging; gamma emitters that can be used for positron emission tomography (PET), such as fluorodeoxyglucose, or chelating agents in order to chelate magnetic resonance imaging probes such as gadolinium or iron.

For compounds of formula (I) when X' is —O— or —S—, the group

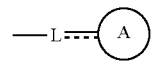

is

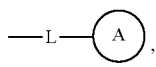, i.e., ==== represents a single bond. However, when X' is N, ==== represents two separate bonds, i.e., not a double bond, joining the nitrogen atom to two separate atoms forming part of the pharmaceutical agent. For exemplified compound compounds 1, 6 and 7, where the pharmaceutical agent is sertraline having the following chemical structure:

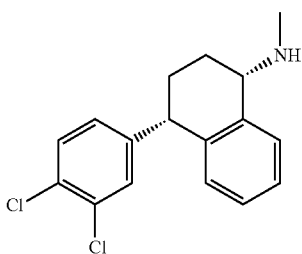 [SMILES: CN[C@H]1CC[C@@H](c2ccc(Cl)c(Cl)c2)c2ccccc21]

the two separate bonds are taken to be the bond from the nitrogen atom to the 1,2,3,4-tetrahydronaphthaline moiety and the bond from the nitrogen atom to the methyl group when the linker is bonded to the secondary nitrogen atom of sertraline. When the pharmaceutical agent is tenofovir, for example, having the structure:

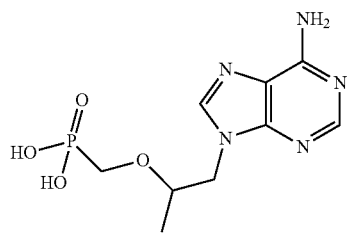 [SMILES: CC(Cn1cnc2c(N)ncnc21)OCP(=O)(O)O]

the two separate bonds are taken to be the bond from the nitrogen atom to the purine moiety and the bond from the nitrogen atom to the hydrogen atom when the linker is bonded to the available primary amine. Similarly, if the pharmaceutical agent is labetalol having the structure:

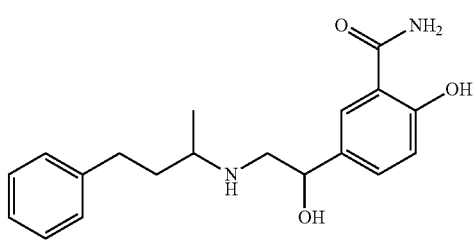 [SMILES: CC(CCc1ccccc1)NCC(O)c1ccc(O)c(C(N)=O)c1]

and the linker is bonded to the available amide group, the two separate bonds are taken to be the bond from the nitrogen atom to the carboxyl carbon atom and the bond from the nitrogen atom to the hydrogen atom. Reference to ==== for compounds of the formula (I) is not intended to imply that the nitrogen atom is bonded to the pharmaceutical agent via a double bond.

For the avoidance of any doubt, reference to "a length equivalent to a linear $C_{20}$alkyl group" refers to the length that 20 singularly bonded carbon atoms would theoretically span.

In some preferred embodiments of the invention, and with reference to the general formula (I), one or more of the following definitions apply:
a) $R^1$ and $R^2$ independently represent H, or a residue of a $C_2$-$C_{28}$ fatty acid.
b) $R^1$ represents H and $R^2$ represents a residue of a $C_2$-$C_{28}$ fatty acid.
c) $R^2$ represents H and $R^1$ represents a residue of a $C_2$-$C_{28}$ fatty acid.
d) $R^1$ and $R^2$ each represent palmitic acid.
e) —X— is —O—.
f) —X— is —NH—.
g) —X— is —S—.
h) —Y— represents an optionally substituted —$C_3$-$C_{20}$alkyl-, —$C_3$-$C_{20}$alkenyl- or —$C_3$-$C_{20}$alkynyl- group, wherein one or more of the carbon atoms in the alkyl, alkenyl or alkynyl group may be replaced with NH, S, O, a $C_5$-$C_8$ aromatic or aliphatic cyclic group or a $C_5$-$C_8$ aromatic or aliphatic heterocyclic group, provided that the alkyl, alkenyl or alkynyl group does not exceed a length equivalent to a linear $C_{20}$alkyl group.
i) —Y— represents a —$C_3$-$C_{20}$alkyl-, —$C_3$-$C_{20}$alkenyl- or —$C_3$-$C_{20}$alkynyl- group optionally substituted with alkyl.
j) —Y— represents a —$C_3$-$C_{20}$alkyl-, —$C_3$-$C_{20}$alkenyl- or —$C_3$-$C_{20}$alkynyl- group optionally substituted with methyl.
k) —Z— is $C(O)R^3$— when —L— is —X'— and $R^3$ is a self-immolative group.
l) $R^3$ is a self-immolative group selected from an acetal, trimethyl lock, p-hydroxybenzylcarbonyl or flipped-ester self-immolative group.
m) —Z— is —C(O)— when —L— is —X'—.
n) X' is O.
o) X' is S.
p) X' is N.
q) X' is $N(R^4)$.
r) $R^4$ is H.
s) $R^4$ is $C_1$-$C_4$alkyl.
t) $R^4$ is methyl.

In a preferred embodiment, —Z— is —C(O)— when —L— is —X'—.

Accordingly, in a further embodiment, the present invention provides compounds of the formula (I) represented by the formula (II):

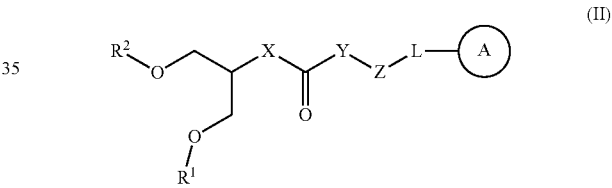

(II)

wherein
$R^1$ and $R^2$ independently represent H, or a residue of a $C_2$-$C_{28}$ fatty acid;
—X— is selected from —O—, —NH— and —S—;
—Y— represents an optionally substituted —$C_3$-$C_{20}$alkyl-, —$C_3$-$C_{20}$alkenyl- or —$C_3$-$C_{20}$alkynyl- group, wherein one or more of the carbon atoms in the alkyl, alkenyl or alkynyl group may be replaced with NH, S, O, a $C_5$-$C_8$ aromatic or aliphatic cyclic group or a $C_5$-$C_8$ aromatic or aliphatic heterocyclic group, provided that the alkyl, alkenyl or alkynyl group does not exceed a length equivalent to a linear $C_{20}$alkyl group;

represents a residue of a pharmaceutical agent;
—L— is —X'— or —X'C(O)—;
—Z— is —C(O)— when —L— is —X'—; or
—Z— is absent when —L— is —X'C(O)—; and
X' is selected from O, S and $NR^4$; and
$R^4$ is H or $C_1$-$C_4$alkyl; or
pharmaceutically acceptable salts thereof.

In a further embodiment the present invention provides compounds of the formula (I) represented by the formula (III):

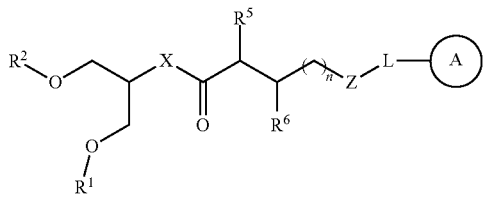

(III)

wherein
R¹, R², —X—,

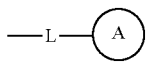

and —Z— are as defined for formula (I);
R⁵ and R⁶ are individually selected from hydrogen and C₁-C₄alkyl; and
n is from 1 to 18; or
pharmaceutically acceptable salts thereof.

In another embodiment compounds of the formula (III) are selected from those compounds listed in Table 1.

TABLE 1

Compounds of formula:

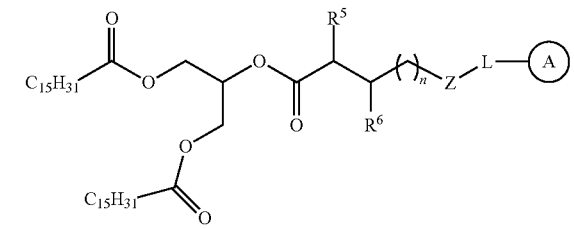

| Compound No. | R⁵ | R⁶ | n | Z | L | A |
|---|---|---|---|---|---|---|
| 1 | H | H | 2 | C(O)TML¹ | NMethyl | Sertraline |
| 2 | H | H | 6 | C(O) | O | Alphaxalone |
| 3 | H | H | 6 | C(O) | O | Metoprolol |
| 4 | H | H | 6 | C(O) | O | Raloxifene |
| 5 | H | H | 6 | C(O)TML | SO₂NH | Celecoxib |
| 6 | H | H | 6 | C(O)PHB² | NMethyl | Sertraline |
| 7 | H | methyl | 1 | C(O)ASI³ | NMethyl | Sertraline |

TABLE 1-continued

Compounds of formula:

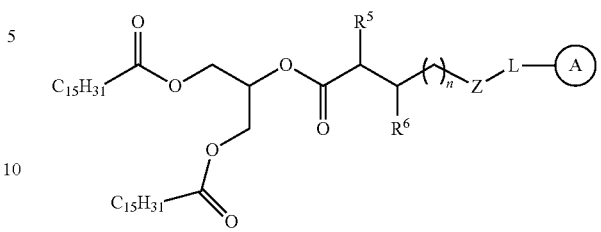

| Compound No. | R⁵ | R⁶ | n | Z | L | A |
|---|---|---|---|---|---|---|
| 8 | H | H | 2 | — | —OC(O)— | Aspirin |
| 9 | H | H | 3 | — | —OC(O)— | Atorvastatin |

¹TML = a trimethyl lock self-immolative group;
²PHB = a p-hydroxybenzylcarbonyl self-immolative group;
³ASI = an acetal self-immolative group.

In one embodiment, the pharmaceutical agent is testosterone or a derivative or analogue thereof. Testosterone replacement therapy (TRT) is commonly used for patients with hypogonadism (a disorder characterised by abnormally low serum testosterone levels) to restore their serum testosterone levels to the normal range and thus relieve many of the symptoms of hypogonadism such as mood disturbance, sexual dysfunction and so on.

Accordingly, in one embodiment, the present invention provides compounds of the formula (I) represented by the formula (IV):

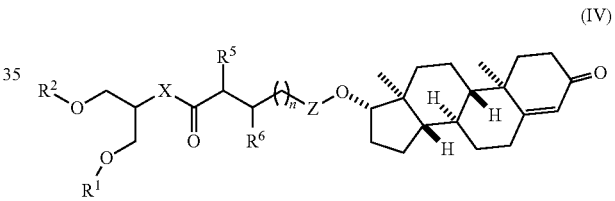

(IV)

wherein R¹, R², and X are as defined for formula (I);
R⁵ and R⁶ are individually selected from hydrogen and C₁-C₄alkyl;
—Z— is —C(O)— or —C(O)R³—;
R³ is a self-immolative group; and
n is from 1 to 18; or
pharmaceutically acceptable salts thereof.

In another embodiment compounds of the formula (IV) are selected from those compounds listed in Table 2.

TABLE 2

Compounds of formula (IV):

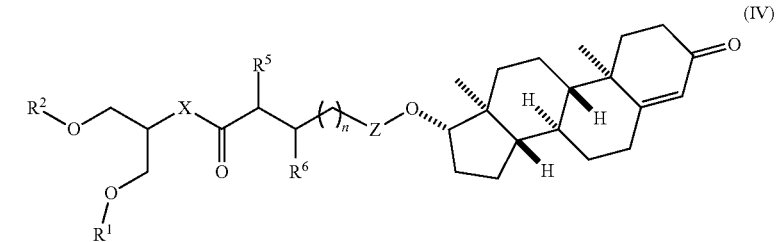

(IV)

| Compound No. | R¹ | R² | X | R⁵ | R⁶ | n | Z |
|---|---|---|---|---|---|---|---|
| 10 | C(O)C₁₅H₃₁ | C(O)C₁₅H₃₁ | O | H | H | 1 | C(O) |
| 11 | C(O)C₁₅H₃₁ | C(O)C₁₅H₃₁ | O | H | H | 2 | C(O) |

TABLE 2-continued

Compounds of formula (IV):

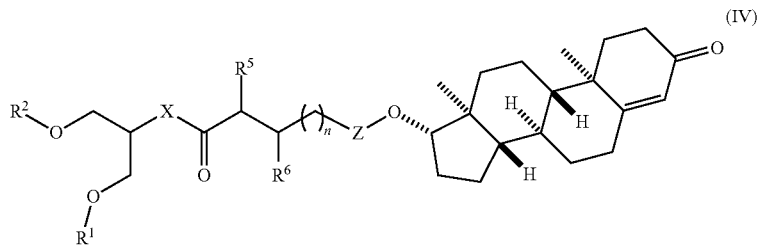

| Compound No. | R¹ | R² | X | R⁵ | R⁶ | n | Z |
|---|---|---|---|---|---|---|---|
| 12 | $C(O)C_{15}H_{31}$ | $C(O)C_{15}H_{31}$ | O | H | H | 4 | C(O) |
| 13 | $C(O)C_{15}H_{31}$ | $C(O)C_{15}H_{31}$ | O | H | H | 6 | C(O) |
| 14 | $C(O)C_{15}H_{31}$ | $C(O)C_{15}H_{31}$ | O | H | H | 8 | C(O) |
| 15 | $C(O)C_{15}H_{31}$ | $C(O)C_{15}H_{31}$ | O | H | H | 14 | C(O) |
| 16 | $C(O)C_{15}H_{31}$ | $C(O)C_{15}H_{31}$ | O | methyl | H | 6 | C(O) |
| 17 | $C(O)C_{15}H_{31}$ | $C(O)C_{15}H_{31}$ | O | methyl | H | 14 | C(O) |
| 18 | $C(O)C_{15}H_{31}$ | $C(O)C_{15}H_{31}$ | O | H | methyl | 1 | C(O) |
| 19 | $C(O)C_{15}H_{31}$ | $C(O)C_{15}H_{31}$ | O | H | methyl | 6 | C(O) |
| 20 | $C(O)C_{15}H_{31}$ | $C(O)C_{15}H_{31}$ | O | H | methyl | 11 | C(O) |
| 21 | $C(O)C_{15}H_{31}$ | $C(O)C_{15}H_{31}$ | O | H | H | 2 | C(O)ASI[1] |
| 22 | $C(O)C_{15}H_{31}$ | $C(O)C_{15}H_{31}$ | O | H | H | 2 | C(O)TML[2] |
| 23 | $C(O)C_{15}H_{31}$ | $C(O)C_{15}H_{31}$ | O | H | methyl | 1 | C(O)ASI |
| 24 | $C(O)C_{15}H_{31}$ | $C(O)C_{15}H_{31}$ | O | H | H | 6 | C(O)ASI |
| 25 | $C(O)C_{15}H_{31}$ | $C(O)C_{15}H_{31}$ | O | H | methyl | 1 | C(O)TML |
| 26 | $C(O)C_{15}H_{31}$ | $C(O)C_{15}H_{31}$ | O | H | H | 6 | C(O)TML |
| 27 | $C(O)C_{15}H_{31}$ | $C(O)C_{15}H_{31}$ | O | H | methyl | 6 | C(O)TML |
| 28 | $C(O)C_{15}H_{31}$ | $C(O)C_{15}H_{31}$ | O | H | H | 6 | C(O)PHB[3] |
| 29 | $C(O)C_{15}H_{31}$ | $C(O)C_{15}H_{31}$ | O | H | methyl | 1 | C(O)FSI[4] |

[1]ASI = an acetal self-immolative group;
[2]TML = a trimethyl lock self-immolative group;
[3]PHB = a p-hydroxybenzylcarbonyl self-immolative group;
[4]FSI = a flipped ester self-immolative group.

In another embodiment, the present invention provides a method of treating or preventing a disease or disorder in which increased testosterone levels are beneficial, comprising administering to the subject in need thereof a therapeutically effective amount of a compound according to formula (IV).

In a further embodiment, the present invention provides the use of a compound according to the formula (IV) in the manufacture of a medicament for treating or preventing a disease or disorder in which increased testosterone levels are beneficial.

In yet another embodiment, the present invention provides a compound of formula (IV) for use in the treatment or prevention of a disease or disorder in which increased testosterone levels are beneficial.

Diseases and disorders in which increased testosterone levels may be beneficial include, but are not limited to, hypogonadism, anaemia due to bone marrow failure, anaemia due to renal failure, chronic respiratory failure, chronic cardiac failure, steroid-dependent autoimmune disorders, AIDS wasting, hereditary angioedema or urticaria, terminal breast cancer or menopause.

In another embodiment, the pharmaceutical agent is mycophenolic acid (MPA). MPA acts on the purine synthesis pathway in lymphocytes and is a widely used immunosuppressant for the treatment of autoimmune disorders and organ transplant rejection.

Accordingly, in a further embodiment, the present invention provides compounds of the formula (I) represented by the formula (VII):

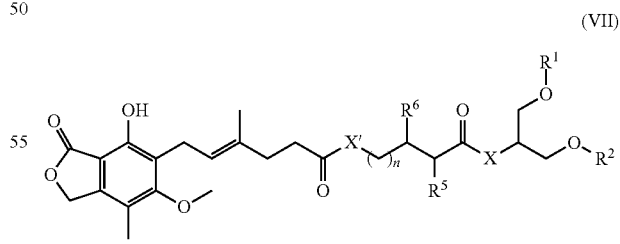

wherein $R^1$, $R^2$, X and X' are as defined for formula (I);

$R^5$ and $R^6$ are individually selected from hydrogen and $C_1$-$C_4$alkyl; and n is from 1 to 18; or pharmaceutically acceptable salts thereof.

In another embodiment compounds of the formula (VII) are selected from those compounds listed in Table 3.

TABLE 3

Compounds of formula (VII):

(VII)

| Compound No. | $R^1$ | $R^2$ | X | $R^5$ | $R^6$ | n | X' |
|---|---|---|---|---|---|---|---|
| 30 | $C(O)C_{15}H_{31}$ | $C(O)C_{15}H_{31}$ | O | H | H | 1 | O |
| 31 | $C(O)C_{15}H_{31}$ | $C(O)C_{15}H_{31}$ | O | H | H | 2 | O |
| 32 | $C(O)C_{15}H_{31}$ | $C(O)C_{15}H_{31}$ | O | H | H | 3 | O |
| 33 | $C(O)C_{15}H_{31}$ | $C(O)C_{15}H_{31}$ | O | H | H | 5 | O |
| 34 | $C(O)C_{15}H_{31}$ | $C(O)C_{15}H_{31}$ | O | H | H | 12 | O |
| 35 | $C(O)C_{15}H_{31}$ | $C(O)C_{15}H_{31}$ | O | H | H | 18 | O |
| 36 | $C(O)C_{15}H_{31}$ | $C(O)C_{15}H_{31}$ | O | methyl | H | 2 | O |
| 37 | $C(O)C_{15}H_{31}$ | $C(O)C_{15}H_{31}$ | O | methyl | H | 3 | O |
| 38 | $C(O)C_{15}H_{31}$ | $C(O)C_{15}H_{31}$ | O | H | methyl | 2 | O |
| 39 | $C(O)C_{15}H_{31}$ | $C(O)C_{15}H_{31}$ | O | H | methyl | 12 | O |
| 40 | $C(O)C_{15}H_{31}$ | $C(O)C_{15}H_{31}$ | O | H | H | 2 | S |

In another embodiment, the present invention provides a method of treating or preventing an autoimmune disorder and organ transplant rejection, comprising administering to the subject in need thereof a therapeutically effective amount of a compound according to formula (VII).

In a further embodiment, the present invention provides the use of a compound according to the formula (VII) in the manufacture of a medicament for treating or preventing an autoimmune disorder and organ transplant rejection.

In yet another embodiment, the present invention provides a compound of formula (VII) for use in the treatment or prevention of an autoimmune disorder and organ transplant rejection.

In another embodiment, the present invention provides a method of promoting lymphatic transport and systemic release of a pharmaceutical agent comprising conjugating to the pharmaceutical compound a prodrug residue of the formula (VI):

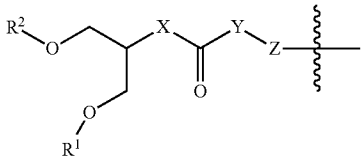

(VI)

wherein
$R^1$ and $R^2$ independently represent H or a residue of a $C_2$-$C_{28}$ fatty acid;
—X— is selected from —O—, —NH— and —S—;
—Y— represents an optionally substituted —$C_3$-$C_{20}$alkyl-, —$C_3$-$C_{20}$alkenyl- or —$C_3$-$C_{20}$alkynyl- group, wherein one or more of the carbon atoms in the alkyl, alkenyl or alkynyl group may be replaced with NH, S, O, a $C_5$-$C_8$ aromatic or aliphatic cyclic group, or a $C_5$-$C_8$ aromatic or aliphatic heterocyclic group, provided that the alkyl, alkenyl or alkynyl group does not exceed a length equivalent to a linear $C_{20}$alkyl group;
—Z— is —C(O)—, —C(O)$R^3$— or —$CH_2$—;
$R^3$ is a self-immolative group; and
∼∼∼ denotes the point where the linker is conjugated to the pharmaceutically active agent; or
pharmaceutically acceptable salts thereof.

In one embodiment Y and Z for the compounds as hereinbefore defined will be selected to facilitate stable transport of the pharmaceutical agent to the intestinal lymph. In another embodiment Y and Z will be selected to facilitate release of the pharmaceutical agent in the lymph, lymphocytes, lymphoid tissues, tissues with high lipase activity such as adipose tissue, certain cancers, the liver or in the systemic circulation. In yet another embodiment Y and Z are selected to both facilitate stable transport of the pharmaceutical agent to the intestinal lymph and to facilitate release of the pharmaceutical agent in the lymph, lymphocytes, lymphoid tissues, tissues with high lipase activity such as adipose tissue, certain cancers, the liver or in the systemic circulation.

Compounds of the present invention are useful for the stable transport of pharmaceutical agents to the intestinal lymph and release of the pharmaceutical agents in the lymph, lymphocytes, lymphoid tissues, tissues with high lipase activity such as adipose tissue, certain cancers, the liver or in the systemic circulation. Compounds of the present invention are particularity useful for the transport and release of pharmaceutical agents that benefit from avoidance of first pass metabolism, for example, compounds that exhibit greater than 50% first pass metabolism. In one embodiment, it is envisaged that the pharmaceutical agent will exhibit greater than 60% first pass metabolism. In another embodiment, the pharmaceutical agent will exhibit greater than 70% first pass metabolism. In a further embodiment, the pharmaceutical agent will exhibit greater than 80% first pass metabolism. In yet another embodiment, the pharmaceutical agent will exhibit greater than 90% first pass metabolism.

Pharmaceutical agents that may benefit from the stable transport to the intestinal lymph and release in the lymph, lymphocytes, lymphoid tissues, tissues with high lipase activity such as adipose tissue, certain cancers, the liver or in the systemic circulation include, but are not limited to, testosterone, mycophenolic acid, oestrogens (estrogen), morphine, metoprolol, raloxifene, alphaxolone, statins such as atorvastatin, pentazocine, propranolol, L-DOPA, buprenorphine, midazolam, lidocaine, chlorpromazine, amitriptyline, nortriptyline, pentazocine, isosorbidedinitrate, glyceryl trinitrate, oxprenolol, labetalol, verapamil, salbutamol, epitiostanol, melphalan, lovastatin and pharmaceutically active peptides.

Compounds of the present invention are also useful for the targeted release of the pharmaceutical agent within the lymphatic system, for example, in the lymph, lymphocytes and lymphoid tissues, as well as in tissues with high lipase activity such as adipose tissue, certain cancers, or the liver.

Pharmaceutical agents that may benefit from targeted release within the lymphatic system or in adipose tissue include, but are not limited to, non-steroidal anti-inflammatory medications (NSAIDS, such as aspirin, ibuprofen, naproxen), COX-2 inhibitors (such ascelecoxib), corticosteroid anti-inflammatory medications (such as prednisolone, dexamethasone), anti-malarial medications (such as hydroxychloroquine), cyclophosphamide, PPAR agonists (such as the fibrates), nitrosoureas, platinum, methotrexate, azathioprine, mercaptopurine, fluorouracil, dactinomycin, anthracyclines, mitomycin C, bleomycin, mithramycin, drugs acting on immunophilins (such as ciclosporin, tacrolimus, sirolimus), sulfasalazine, leflunomide, mycophenolate, opioids, fingolimod, myriocin, chlorambucil, doxorubicin, nelarabine, cortisone, dexamethasone, prednisone, pralatrexate, vinblastine, bortezomib, thiotepa, nelarabine, daunorubicin hydrochloride, clofarabine, cytarabine, dasatinib, imatinibmesylate, ponatinib hydrochloride, vincristine sulfate, bendamustine hydrochloride, fludarabine phosphate, bosutinib, nilotinib, omacetaxinemepesuccinate, anastrozole, capecitabine, letrozole, paclitaxel, gemcitabine, fulvestrant, tamoxifen, lapatinib, toremifene, ixabepilone, eribulin, albendazole, ivermectin, diethylcarbamazine, doxycycline, closantel, maraviroc, enfuvirtide, deoxythymidine, zidovudine, stavudine, didanosine, zalcitabine, abacavir, lamivudine, emtricitabine, tenofovir, nevirapine, delavirdine, efavirenz, rilpivirine, raltegravir, elvitegravir, lopinavir, indinavir, nelfinavir, amprenavir, ritonavir, acyclovir and immunosuppressants such as mycophenolic acid, cyclosporine, tacrolimus and sirolimus.

As a general strategy, compounds of the present invention may be synthesised via one of the following routes:

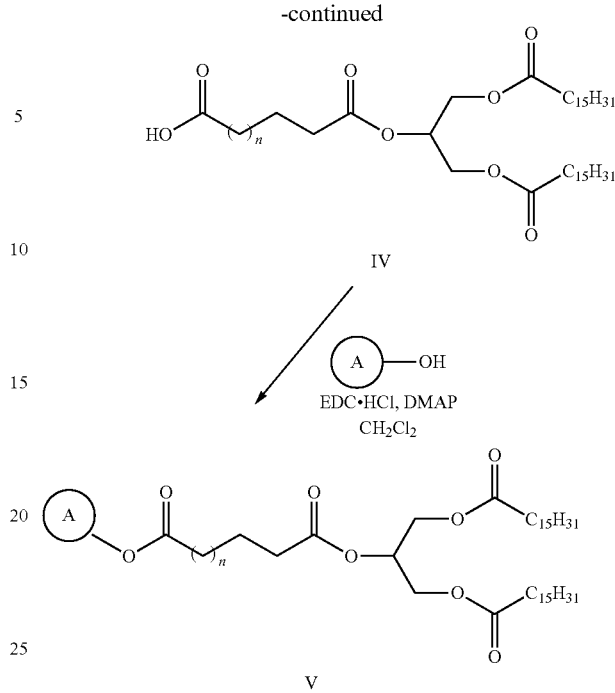

Compounds of the invention wherein —Y— is an unsubstituted alkyl group can be prepared by reaction of acid-triglycerides IV with an alcohol-containing pharmaceutical agent (A-OH) under standard ester-bond forming conditions as shown in Scheme 1. In most cases, the acid-triglycerides IV can be accessed from acid anhydrides I (for n=1) or diacid chlorides II (for n>1), obtained from the corresponding dicarboxylic acids, by treatment with 1,3-diacylglycerol III in the presence of pyridine.

For the synthesis of compounds wherein —Y— is an α- or β-substituted alkyl group, the conversion of anhydrides I or diacid chlorides II to acid-triglyceride IV via the pathway described in Scheme 1 is not typically feasible due to the starting material being asymmetrical. Accordingly, synthesis via Scheme 1 will lead to the formation of mixed acid-triglyceride products. In these cases, the linker unit can be constructed from simpler starting materials and then merged with diacylglycerol III at an appropriate point in the sequence to ultimately provide acid-triglycerides IV.

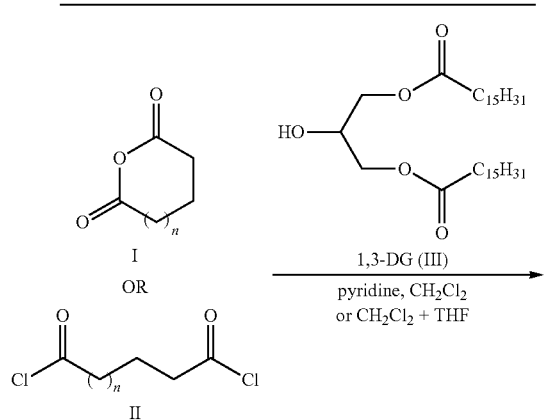

Scheme 1. Synthesis of unsubstituted alkyl-linked compounds of the invention wherein L is X′ and X′ is O

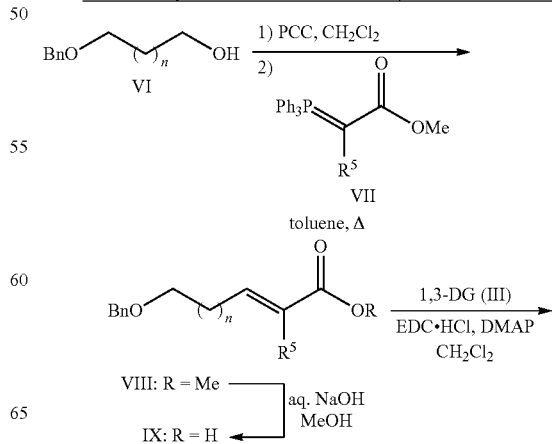

Scheme 2. Synthesis of α-substituted compounds of the invention

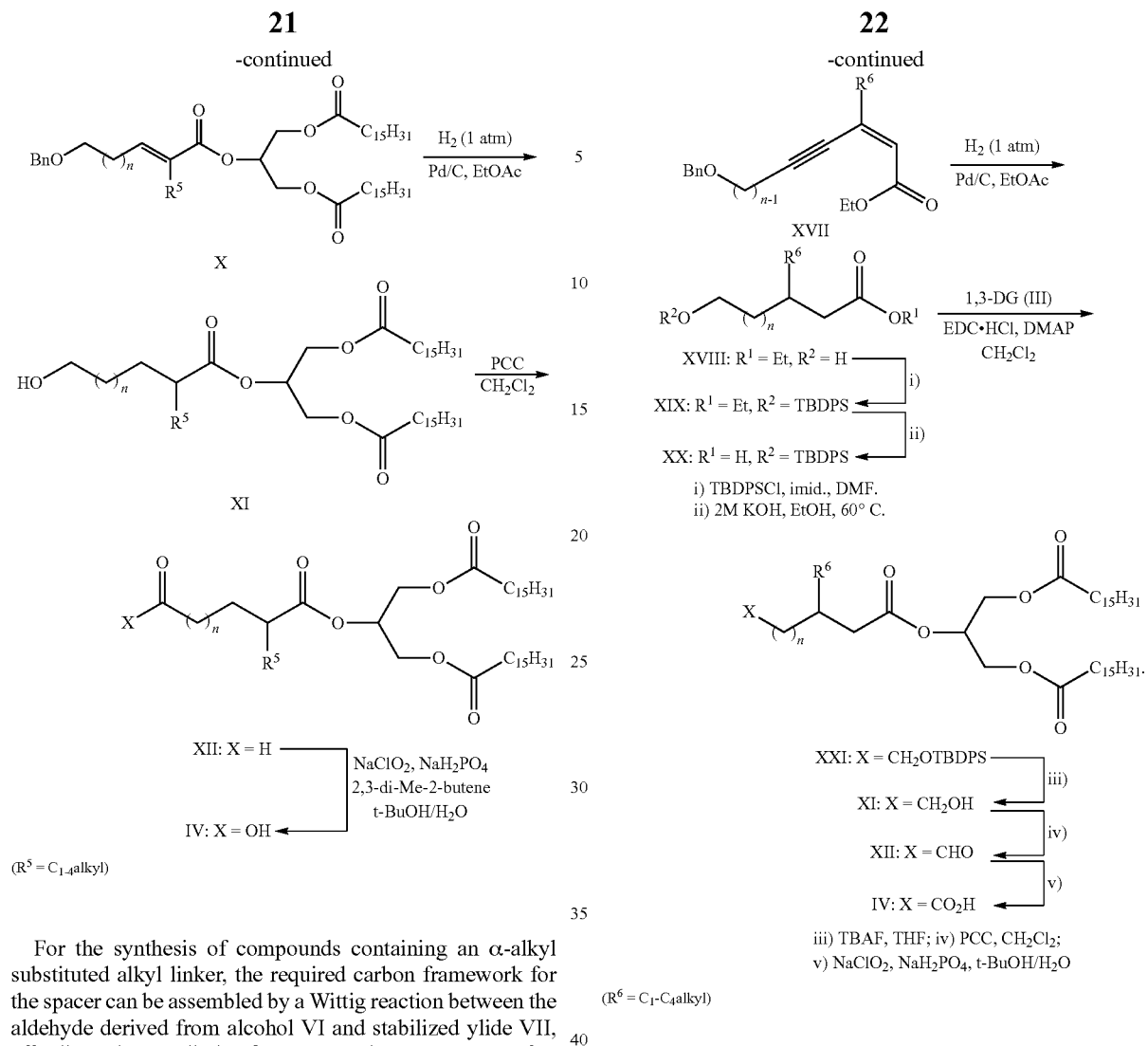

For the synthesis of compounds containing an α-alkyl substituted alkyl linker, the required carbon framework for the spacer can be assembled by a Wittig reaction between the aldehyde derived from alcohol VI and stabilized ylide VII, affording the α-alkyl-α,β-unsaturated ester VIII. After hydrolysis of the ester to liberate free acid IX, coupling with diacylglycerol III under standard conditions provides triglyceride X. One-step hydrogenation-hydrogenolysis furnishes saturated alcohol XI, which can first be oxidised to aldehyde XII using PCC and then further oxidised under Pinnick conditions to give desired α-substituted acid-triglyceride IV.

Scheme 3. Synthesis of β-substituted compounds of the invention.

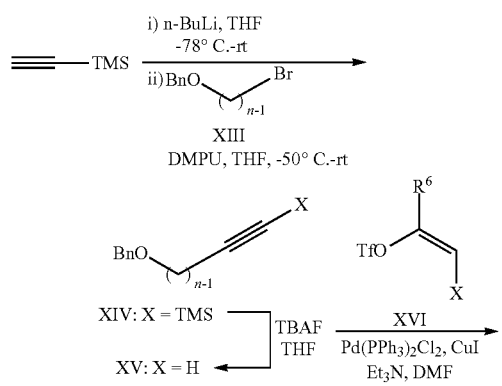

For the synthesis of compounds containing an β-alkyl substituted alkyl linker, the method outlined in Scheme 1 above can be used in the specific case where n=1, since a β-substituent maintains symmetry in diacid chloride II. Scheme 3 above provides a method for the synthesis of compounds containing a β-alkyl substituent in cases where n>1. Initially, deprotonation of TMS acetylene using a strong base such as n-BuLi, followed by addition of alkyl bromide XIII as an electrophile results in formation of silylalkyne XIV. Following desilylation, Sonogashira cross-coupling of alkyne XV with enol triflate XVI mediated by $Pd^{II}$ and $Cu^{I}$ affords enyne XVII containing the required β-alkyl substituent. Catalytic hydrogenation of enyne XVII then gives β-methyl-ω-hydroxyester XVIII, which can be converted to TBDPS ether XIX in preparation for introduction of the glyceride functionality. This is then accomplished by hydrolysis of ester XIX under forcing basic conditions (2 M KOH in EtOH at 60° C.), followed by standard coupling of the resulting acid XX with diacylglycerol III to give triglyceride XXI. Desilylation using TBAF then affords hydroxytriglyceride XI, which can be transformed to target acid-triglyceride IV in a similar way as outlined in Scheme 2.

Scheme 4. Synthesis of compounds wherein L is ——X'C(O)—— and X' is O or S

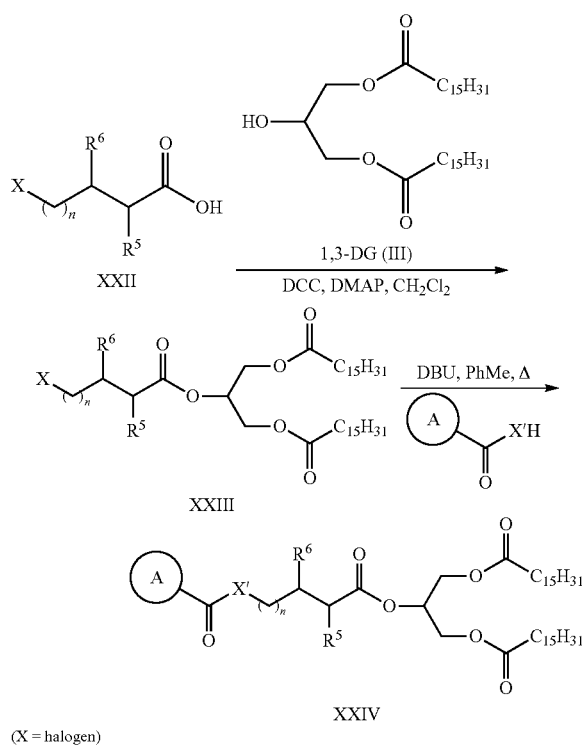

(X = halogen)

Where the pharmaceutically active agent has a carboxylic acid group that can be conjugated to form the compounds of the present invention, the compounds can generally be prepared according to Scheme 4. To generate the ester bond between the glyceride and the desired linker, ω-halocarboxylic acids XXII are coupled with 1,3-diacylglycerol III in the presence of standard coupling conditions to provide ω-halotriglycerides XXIII. Conjugation of carboxylic acid-containing pharmaceutical agents can then be achieved by displacing the halogen leaving group with the appropriate carboxylate nucleophile to provide the compounds of the invention XXIV. In cases where halocarboxylic acid XXII is not commercially available, synthesis from simpler precursors is required. For shorter-chain (n=2, 3) α- or β-alkyl substituted examples, or longer-chain (eg: n=12) unsubstituted examples, the necessary acids XXII can be accessed by ring-opening of the corresponding lactones (see example 6, compounds aj-am). For longer-chain α- or β-alkyl examples (n>3), the necessary halotriglycerides XXIII can be prepared from the hydroxytriglycerides XI described in Schemes 2 and 3 above.

Where the compounds of the present invention require purification, techniques such as recrystallisation and chromatographic techniques including high-performance liquid chromatography (HPLC) and normal phase or reversed-phase silica gel chromatography may be used. The compounds may be characterised by nuclear magnetic resonance (NMR) mass spectrometry and/or other appropriate methods.

It will be understood that the compounds of the present invention may exist in one or more stereoisomeric forms (e.g. diastereomers). The present invention includes within its scope all of these stereoisomeric forms either isolated (in, for example, enantiomeric isolation), or in combination (including racemic mixtures and diastereomic mixtures).

The invention thus also relates to compounds in substantially pure stereoisomeric form with respect to the asymmetric centres of the amino acid residues, e.g., greater than about 90% de, such as about 95% to 97% de, or greater than 99% de, as well as mixtures, including racemic mixtures, thereof. Such diastereomers may be prepared by asymmetric synthesis, for example, using chiral intermediates, or mixtures may be resolved by conventional methods, e.g., chromatography, or use of a resolving agent.

Where the compound comprises one or more functional groups that may be protonated or deprotonated (for example at physiological pH) the compound may be prepared and/or isolated as a pharmaceutically acceptable salt. It will be appreciated that the compound may be zwitterionic at a given pH. As used herein the expression "pharmaceutically acceptable salt" refers to the salt of a given compound, wherein the salt is suitable for administration as a pharmaceutical. Such salts may be formed by the reaction of an acid or a base with an amine or a carboxylic acid group respectively.

Pharmaceutically acceptable acid addition salts may be prepared from inorganic and organic acids. Examples of inorganic acids include hydrochloric acid, hydrobromic acid, sulfuric acid, nitric acid, phosphoric acid and the like. Examples of organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

Pharmaceutically acceptable base addition salts may be prepared from inorganic and organic bases. Corresponding counter ions derived from inorganic bases include the sodium, potassium, lithium, ammonium, calcium and magnesium salts. Organic bases include primary, secondary and tertiary amines, substituted amines including naturally-occurring substituted amines, and cyclic amines, including isopropylamine, trimethyl amine, diethylamine, triethylamine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, and N-ethylpiperidine.

Acid/base addition salts tend to be more soluble in aqueous solvents than the corresponding free acid/base forms.

The compounds of the invention may be in crystalline form or as solvates (e.g. hydrates) and it is intended that both forms are within the scope of the present invention. The term "solvate" is a complex of variable stoichiometry formed by a solute and a solvent. Such solvents should not interfere with the biological activity of the solute. Solvents may be, by way of example, water, ethanol or acetic acid. Methods of solvation are generally known within the art.

The route of administration for the compounds of the present invention is intended to include oral and enteral administration. Accordingly, the active compound may be formulated with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal or sublingual tablets, troches, capsules, elixirs, suspensions, syrups, wafers, and the like. The amount of active compound in such therapeutically useful compositions is such that a suitable dosage will be obtained.

The tablets, troches, pills, capsules and the like may also contain the components as listed hereafter: a binder such as gum, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the compounds of the invention may be incorporated into sustained-release preparations and formulations, including those that allow specific delivery of the active peptide to specific regions of the gut.

Liquid formulations may also be administered enterally via a stomach or oesophageal tube.

In one embodiment the compound(s) of the invention will be administered orally with food to promote transport to the intestinal lymph.

In another embodiment the compound(s) of the invention will be co-administered orally with a lipid based formulation to promote transport to the intestinal lymph with or without co-administration with food.

Lipid based formulations for oral delivery are known in the art and may include, for example, substantially non-aqueous vehicles which typically contain one or more lipid components. The lipid vehicles and resulting lipid formulations may be usefully classified as described below according to their shared common features according to the lipid formulation classification system (LFCS) (Pouton, C. W., *Eur. J. Pharm. Sci.* 11 (Supp 2), S93-S98, 2000; Pouton, C. W., *Eur. J. Pharm. Sci.* 29 278-287, 2006).

Thus lipid vehicles, and the resulting lipid formulations, may contain oil/lipids and/or surfactants, optionally with co-solvents. Type I formulations include oils or lipids which require digestion, such as mono, di and tri-glycerides and combinations thereof. Type II formulations are water-insoluble SEDDS which contain lipids and oils used in Type I formulations, with additional water insoluble surfactants. Type III formulations are SEDDS or self-microemulsifying drug delivery systems (SMEDDS) which contain lipids and oils used in Type I formulations, with additional water-soluble surfactants and/or co-solvents (Type IIIa) or a greater proportion of water-soluble components (Type IIIb). Type IV formulations contain predominantly hydrophilic surfactants and co-solvents (e.g. PEG, propylene glycol and diethylene glycol monoethyl ether) and are useful for drugs which are poorly water soluble but not lipophilic. Any such lipid formulation (Type I-IV) is contemplated herein.

In some embodiments, the lipid vehicle contains one or more oils or lipids, without additional surfactants, co-surfactants or co-emulsifiers, or co-solvents, that is to say consists essentially of one or more oils or lipids. In some further embodiments the lipid vehicle contains one or more oils or lipids together with one or more water-insoluble surfactants, optionally together with one or more co-solvents. In some further embodiments, the lipid vehicle contains one or more oils or lipids together with one or more water-soluble surfactants, optionally together with one or more co-solvents. In some embodiments, the lipid vehicle contains a mixture of oil/lipid, surfactant and co-solvent. In some embodiments, the lipid vehicle is consists essentially of one or more surfactants/co-surfactants/co-emulsifiers, and/or solvents/co-solvents.

Examples of oils or lipids which may be used in the present invention include almond oil, babassu oil, blackcurrant seed oil, borage oil, canola oil, castor oil, coconut oil, cod liver oil, corn oil, cottonseed oil, evening primrose oil, fish oil, grape seed oil, mustard seed oil, olive oil, palm kernel oil, palm oil, peanut oil, rapeseed oil, safflower oil, sesame oil, shark liver oil, soybean oil, sunflower oil, walnut oil, wheat germ oil, avocado oil, bran oil, hydrogenated castor oil, hydrogenated coconut oil, hydrogenated cottonseed oil, hydrogenated palm oil, hydrogenated soybean oil, partially hydrogenated soybean oil, hydrogenated vegetable oil, caprylic/capric glycerides, fractionated triglycerides, glyceryl tricaprate, glyceryl tricaproate, glyceryl tricaprylate, glyceryl tricaprylate/caprate, glyceryl tricaprylate/caprate, glyceryl tricaprylate/caprate/laurate, glyceryl tricaprylate/caprate/linoleate, glyceryl tricaprylate/caprate/stearate, glyceryl trilaurate, glyceryl monolaurate, glyceryl behenate, glyceryl monolinoleate, glyceryl trilinolenate, glyceryl trioleate, glyceryl triundecanoate, glyceryl tristearate linoleic glycerides, saturated polyglycolized glycerides, synthetic medium chain triglycerides containing primarily $C_8$-$C_{12}$ fatty acid chains, medium chain triglycerides containing primarily $C_8$-$C_{12}$ fatty acid chains, long chain triglycerides containing primarily >$C_{12}$ fatty acid chains, modified triglycerides, fractionated triglycerides, and mixtures thereof.

Examples of mono and diglycerides which may be used in the present invention include glycerol mono- and diesters having fatty acid chains from 8 to 40 carbon atoms, including hydrolysed coconut oils (e.g. Capmul® MCM), hydrolysed corn oil (e.g. Maisine™ 35-1). In some embodiments, the monoglycerides and diglycerides are mono- or di-saturated fatty acid esters of glycerol having fatty acid chains of 8 to 18 carbon chain length (e.g. glyceryl monostearate, glyceryl distearate, glyceryl monocaprylate, glyceryl dicaprylate, glyceryl monocaprate and glyceryl dicaprate).

Suitable surfactants for use in the lipid formulations include propylene glycol mono- and di-esters of $C_8$-$C_{22}$ fatty acids, such as, but not limited to, propylene glycol monocaprylate, propylene glycol dicaprylate, propylene glycol monolaurate, sold under trade names such as Capryol® 90, Labrafac® PG, Lauroglycol® FCC, sugar fatty acid esters, such as, but not limited to, sucrose palmitate, sucrose laurate, sucrose stearate; sorbitan fatty acid esters such as, but not limited to, sorbitan laurate, sorbitan palmitate, sorbitan oleate; polyoxyethylene sorbitan fatty acid esters such as, but not limited to, polysorbate 20, polysorbate 40, polysorbate 60, and polysorbate 80, polysorbate 85; polyoxyethylene mono- and di-fatty acid esters including, but not limited to polyoxyl 40 stearate and polyoxyl40 oleate; a mixture of polyoxyethylene mono- and di-esters of $C_8$-$C_{22}$ fatty acids and glyceryl mono-, di-, and tri-esters of $C_8$-$C_{22}$ fatty acids as sold under tradenames such as Labrasol®, Gelucire® 44/14, Gelucire® 50/13, Labrafil®; polyoxyethylene castor oils compound such as, but not limited to, polyoxyl 35 castor oil, polyoxyl 40 hydrogenated castor oil, and polyoxyl 60 hydrogenated castor oil, as are sold under tradenames such as Cremophor®/Kolliphor EL, Cremophor®/Kolliphor® RH40, Cremophor®/Kollipohor®

RH60; polyoxyethylene alkyl ether including but not limited to polyoxyl 20 cetostearyl ether, and polyoxyl 10 oleyl ether; DL-.alpha.-tocopheryl polyethylene glycol succinate as may be sold under the tradename; glyceryl mono-, di-, and tri-ester; a glyceryl mono-, di-, and tri-esters of $C_8$-$C_{22}$ fatty acid; a sucrose mono-, di-, and tri-ester; sodium dioctylsulfosuccinate; polyoxyethylene-polyoxypropylene copolymers such as, but not limited to poloxamer 124, poloxamer 188, poloxamer 407; polyoxyethyleneethers of $C_8$-$C_{22}$ fatty alcohols including, but not limited to polyoxyethylenelauryl alcohol, polyoxyethylenecetyl alcohol, polyoxyethylenestearyl alcohol, polyoxyethyleneoleyl alcoholas sold under tradenames such as Brij® 35, Brij® 58, Brij® 78Brij® 98, or a mixture of any two or more thereof.

A co-emulsifier, or co-surfactant, may be used in the formulation. A suitable co-emulsifier or co-surfactant may be a phosphoglyceride; a phospholipid, for example lecithin, or a free fatty acid that is liquid at room temperature, for example, iso-stearic acid, oleic acid, linoelic acid, linolenic acid, palmitic acid, stearic acid, lauric acid, capric acid, caprylic acid and caproic acid.

Suitable solvents/co-solvents include ethanol, propylene glycol, polyethylene glycol, diethylene glycol monoethyl ether and glycerol.

A polymer may also be used in the formulation to inhibit drug precipitation. A range of polymers have been shown to impart these properties and are well known to those skilled in the art. Suitable polymers include hydroxypropylmethylcellulose, hydroxypropylmethylcellulose acetyl succinate, other cellulose-derived polymers such as methylcellulose; poly(meth)acrylates, such as the Eudragit series of polymers, including Eudragit E100, polyvinylpyrrolidone or others as described in e.g. Warren et al. *Mol. Pharmaceutics* 2013, 10, 2823-2848.

Formulations may also contain materials commonly known to those skilled in the art to be included in lipid based formulations, including antioxidants, for example, butylated hydroxyanisole (BHA) or butylated hydroxytoluene (BHT) and solidifying agents such as microporous silica, for example magnesium alumino-metasilicate (Neusilin).

In another embodiment the compound(s) may be co-administered orally with an enzyme inhibitor to increase stability of the prodrug in the gastrointestinal tract or enterocyte. In certain embodiments it is envisaged that the enzyme inhibitor will inhibit pancreatic lipases, examples of which include, but are not limited to, Alli and Orlistat. In other embodiments it is envisaged that the enzyme inhibitor will inhibit cellular lipase enzymes such as monoacylglycerol lipase, an example of which includes, but is not limited to, JZL184 (4-nitrophenyl-4-[bis(1,3-benzodioxol-5-yl)(hydroxy)methyl]piperidine-1-carboxylate).

While the compounds as hereinbefore described, or pharmaceutically acceptable salts thereof, may be the sole active ingredient administered to the subject, the administration of other active ingredient(s) with the compound is within the scope of the invention. In one or more embodiments it is envisaged that a combination of two or more of the compounds of the invention will be administered to the subject.

The present invention also provides a pharmaceutical composition comprising a therapeutically effective amount of a compound as hereinbefore defined, or a pharmaceutically acceptable salt thereof, together with at least one pharmaceutically acceptable carrier or diluent.

The term "composition" is intended to include the formulation of an active ingredient with encapsulating material as carrier, to give a capsule in which the active ingredient (with or without other carrier) is surrounded by carriers.

As will be readily appreciated by those skilled in the art, the nature of the pharmaceutically acceptable carrier will depend on the nature of the condition and the mammal to be treated. It is believed that the choice of a particular carrier or delivery system could be readily determined by a person skilled in the art. In the preparation of any formulation containing the active compound care should be taken to ensure that the activity of the compound is not destroyed in the process and that the compound is able to reach its site of action without being destroyed. In some circumstances it may be necessary to protect the compound by means known in the art, such as, for example, micro encapsulation.

Those skilled in the art may readily determine appropriate formulations for the compounds of the present invention using conventional approaches. Identification of preferred pH ranges and suitable excipients, for example antioxidants, is routine in the art. Buffer systems are routinely used to provide pH values of a desired range and include carboxylic acid buffers for example acetate, citrate, lactate and succinate. A variety of antioxidants are available for such formulations including phenolic compounds such as BHT or vitamin E, reducing agents such as methionine or sulphite, and metal chelators such as EDTA.

Pharmaceutically acceptable vehicles and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

The compound(s) may also be administered with one or more additional therapeutic agents in combination. The combination may allow for separate, sequential or simultaneous administration of the compound(s) as hereinbefore described with the other active ingredient(s). The combination may be provided in the form of a pharmaceutical composition.

The term "combination", as used herein refers to a composition or kit of parts where the combination partners as defined above can be dosed dependently or independently or by use of different fixed combinations with distinguished amounts of the combination partners, i.e., simultaneously or at different time points. The combination partners can then, e.g., be administered simultaneously or chronologically staggered, that is at different time points and with equal or different time intervals for any part of the kit of parts. The ratio of the total amounts of the combination partners to be administered in the combination can be varied, e.g. in order to cope with the needs of a patient sub-population to be treated or the needs of the single patient which different needs can be due to age, sex, body weight, etc. of the patients.

It is especially advantageous to formulate the compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutically acceptable vehicle. The specification for the novel dosage unit forms of the invention are dictated by and directly dependent on (a) the unique characteristics of the active material and the particular therapeutic effect to be achieved, and (b) the limitations inherent in the art of compounding active materials for the treatment of disease in living subjects having a diseased condition in which bodily health is impaired as herein disclosed in detail.

As mentioned above the principal active ingredient may be compounded for convenient and effective administration in therapeutically effective amounts with a suitable pharmaceutically acceptable vehicle in dosage unit form. A unit dosage form can, for example, contain the principal active compound in amounts ranging from 0.25 µg to about 2000 mg. Expressed in proportions, the active compound may be present in from about 0.25 µg to about 2000 mg/mL of carrier. In the case of compositions containing supplementary active ingredients, the dosages are determined by reference to the usual dose and manner of administration of the said ingredients.

As used herein, the term "effective amount" refers to an amount of compound which, when administered according to a desired dosing regimen, provides the desired therapeutic activity. Dosing may occur once, or at intervals of minutes or hours, or continuously over any one of these periods. Suitable dosages may lie within the range of about 0.1 ng per kg of body weight to 1 g per kg of body weight per dosage. A typical dosage is in the range of 1 µg to 1 g per kg of body weight per dosage, such as is in the range of 1 mg to 1 g per kg of body weight per dosage. In one embodiment, the dosage may be in the range of 1 mg to 500 mg per kg of body weight per dosage. In another embodiment, the dosage may be in the range of 1 mg to 250 mg per kg of body weight per dosage. In yet another embodiment, the dosage may be in the range of 1 mg to 100 mg per kg of body weight per dosage, such as up to 50 mg per body weight per dosage.

The terms "treatment" and "treating" as used herein cover any treatment of a condition or disease in an animal, preferably a mammal, more preferably a human and includes the treatment of any disease or disorder in which increased testosterone levels are beneficial. The terms "prevention" and "preventing" as used herein cover the prevention or prophylaxis of a condition or disease in an animal, preferably a mammal, more preferably a human and includes preventing any disease or disorder in which increased testosterone levels are beneficial.

The invention will now be described with reference to the following non-limiting examples. The following examples are representative of the general formula (I) and provide detailed methods for preparing exemplary compounds of the present invention.

Example 1. Methods for Preparing Compounds of the Formula (I) Wherein Y Represents an Unsubstituted Alkyl Group and L Represents X' where X' is O a) 5-((1,3-Bis(palmitoyloxy)propan-2-yl)oxy)-5-oxopentanoic acid (IV)

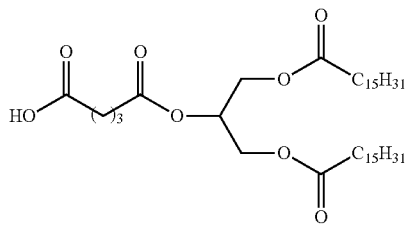

4-(Dimethylamino)pyridine (64.4 mg, 0.527 mmol) was added to a solution of diglyceride III (300 mg, 0.527 mmol) and glutaric anhydride I (120 mg, 1.05 mmol) in pyridine/THF/CH$_2$Cl$_2$ (1.5 mL each) and the mixture stirred at rt for two days. The reaction was diluted with ethyl acetate (20 mL), washed with 1 M HCl and brine (20 mL each), dried (MgSO$_4$) and concentrated under reduced pressure to give the crude product. Silica gel chromatography (10% to 15% ethyl acetate/hexanes) gave acid triglyceride IV (140 mg, 39%) as a colourless solid.

$^1$H NMR (400 MHz, CDCl$_3$) δ 5.26 (m, 1H), 4.31 (dd, J=11.9, 4.3 Hz, 2H), 4.14 (dd, J=11.9, 5.9 Hz, 2H), 2.44 (t, J=7.4 Hz, 2H), 2.42 (t, J=7.4 Hz, 2H), 2.31 (t, J=7.6 Hz, 4H), 1.96 (pent, J=7.3 Hz, 2H), 1.67-1.54 (m, 4H), 1.49-1.18 (m, 48H), 0.88 (t, J=6.8 Hz, 6H).

b) Octanedioyl Dichloride (II)

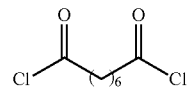

A mixture of suberic acid (84.2 mg, 0.483 mmol) and DMF (one drop) in thionyl chloride (351 µL, 4.83 mmol) was heated at reflux for 1.5 hours. The reaction was cooled to rt, diluted with toluene (5 mL) and concentrated under reduced pressure to give diacid chloride II (102 mg, quant.) as a yellow oil that was used without purification.

$^1$H NMR (400 MHz, CDCl$_3$) δ 2.90 (t, J=7.2 Hz, 4H), 1.78-1.68 (m, 4H), 1.42-1.35 (m, 4H).

c) 8-((1,3-Bis(palmitoyloxy)propan-2-yl)oxy)-8-oxooctanoic acid (IV)

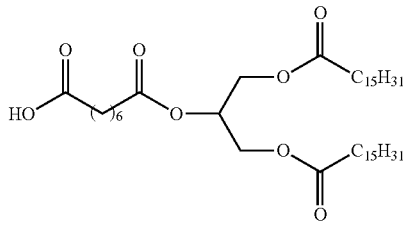

A solution of diglyceride III (50.0 mg, 0.0879 mmol) and pyridine (71.1 µL, 0.879 mmol) in CH$_2$Cl$_2$ (2 mL) was added to octanedioyl dichloride II (102 mg, 0.483 mmol) in CH$_2$Cl$_2$ (1.5 mL) and the mixture stirred at rt for 3.5 hours. The reaction was cooled to rt, diluted with water (10 mL) and 1 M HCl (3 mL) and the aqueous layer extracted with ethyl acetate (3×15 mL). The combined organic extracts were washed with 1 M HCl (30 mL) and brine (2×30 mL), dried (MgSO$_4$) and concentrated under reduced pressure to give the crude product. Purification by silica gel chromatography (20% to 50% ethyl acetate/hexanes) gave the acid triglyceride IV (29.5 mg, 46%) as a pale yellow solid.

$^1$H NMR (400 MHz, CDCl$_3$) δ 5.25 (m, 1H), 4.29 (dd, J=11.9, 4.3 Hz, 2H), 4.14 (dd, J=11.9, 5.9 Hz, 2H), 2.37-2.28 (m, 8H), 1.68-1.56 (m, 8H), 1.39-1.21 (m, 52H), 0.87 (t, J=6.8 Hz, 6H).

d) 1-((3R,5S,8S,9S,10S,13S,14S,17S)-17-Acetyl-10, 13-dimethyl-11-oxohexadecahydro-1H-cyclopenta[a]phenanthren-3-yl) 10-(1,3-bis(palmitoyloxy)propan-2-yl) decanedioate (2)

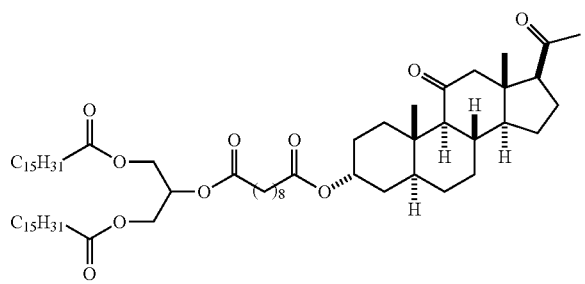

4-(Dimethylamino)pyridine (DMAP, 5.2 mg, 42.5 µmol), EDC.HCl (20.4 mg, 106 µmol) and alphaxolone (22.6 mg, 68.0 µmol) were added to a solution of acid-TG IV (32.0 mg, 42.5 µmol) in $CH_2Cl_2$ (1.5 mL) and the mixture stirred at rt for 22 hours. The reaction was diluted with $CH_2Cl_2$ (5 mL), silica gel was added and the mixture concentrated under reduced pressure. Purification by silica gel chromatography (15% to 20% ethyl acetate/hexanes) gave Compound 2 (20.5 mg, 45%) as a colourless solid.

$^1$H NMR (400 MHz, $CDCl_3$) δ 5.25 (m, 1H), 5.00 (m, 1H), 4.29 (dd, J=11.9, 4.4 Hz, 2H), 4.14 (dd, J=11.9, 5.9 Hz, 2H), 2.71 (t, J=9.0 Hz, 1H), 2.56 (d, J=11.9 Hz, 1H), 2.48 (d, J=12.0 Hz, 1H), 2.34-2.18 (m, 10H), 2.09 (s, 3H), 1.86-1.37 (m, 18H), 1.36-1.07 (m, 62H), 1.00 (s, 3H), 0.87 (t, J=6.8 Hz, 6H), 0.57 (s, 3H).

e) 1-(1,3-Bis(palmitoyloxy)propan-2-yl) 10-(1-((tert-butoxycarbonyl)(isopropyl)amino)-3-(4-(2-methoxyethyl)phenoxy)propan-2-yl) decanedioate (XXV)

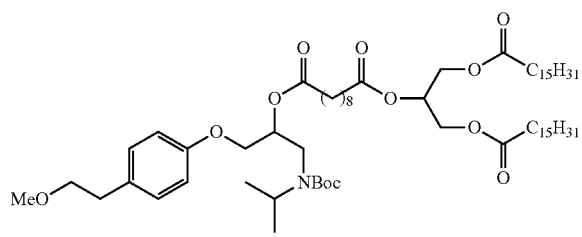

4-(Dimethylamino)pyridine (DMAP, 5.6 mg, 45.4 µmol) and EDC.HCl (17.4 mg, 90.0 µmol) were added to a solution of previously prepared N-Boc-metoprolol (16.7 mg, 45.4 µmol) and acid-TG IV (34.2 mg, 45.4 µmol) in $CH_2Cl_2$ (2 mL) and the mixture stirred at rt for 19 hours. The reaction was then concentrated under reduced pressure to give the crude product. Purification by silica gel chromatography (10% to 25% ethyl acetate/hexanes) gave protected prodrug XXV (23.3 mg, 47%) as a colourless solid.

$^1$H NMR (400 MHz, $CDCl_3$) δ 7.12 (d, J=8.5 Hz, 2H), 6.83-6.78 (m, 2H), 5.33 (m, 1H), 5.25 (m, 1H), 4.29 (dd, J=11.9, 4.4 Hz, 2H), 4.14 (dd, J=11.9, 5.9 Hz, 2H), 4.22-3.98 (m, 3H), 3.55 (t, J=7.1 Hz, 2H), 3.47 (m, 1H), 3.34 (s, 3H), 3.31 (m, 1H), 2.81 (t, J=7.1 Hz, 2H), 2.33-2.27 (m, 8H), 1.64-1.56 (m, 8H), 1.46 (s, 9H), 1.37-1.20 (m, 56H), 1.18 (d, J=6.8 Hz, 3H), 1.14 (d, J=6.7 Hz, 3H), 0.87 (t, J=6.9 Hz, 6H).

f) 1-(1,3-Bis(palmitoyloxy)propan-2-yl) 10-(1-(isopropylamino)-3-(4-(2-methoxyethyl)phen-oxy)propan-2-yl) decanedioate (3)

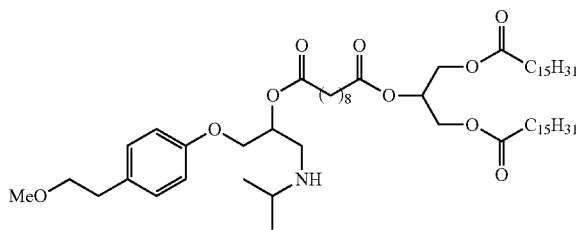

Trifluoroacetic acid (TFA) (7.7 µL, 0.104 mmol) was added to a solution of Boc carbamate XXV (23.0 mg, 0.0209 mmol) in $CH_2Cl_2$ (1 mL) and the reaction stirred at rt for six hours. TLC analysis at this time showed slow progression of the reaction so further TFA (15.4 µL, 0.208 mmoL) was added and the mixture stirred at rt for an additional 18 hours. Triethylamine ($Et_3N$, 50 µL) was added and the reaction concentrated under a stream of $N_2$ gas to give the crude product. Purification by silica gel chromatography (20% to 40% to 60% ethyl acetate/hexanes with 1% $Et_3N$) gave Compound 3 (19.0 mg, 91%) as a colourless oil.

$^1$H NMR (400 MHz, $CDCl_3$) δ 7.16-7.09 (m, 2H), 6.87-6.81 (m, 2H), 5.29-5.18 (m, 2H), 4.29 (dd, J=11.9, 4.4 Hz, 2H), 4.14 (dd, J=11.9, 5.9 Hz, 2H), 4.11-4.08 (m, 2H), 3.55 (t, J=7.1 Hz, 2H), 3.34 (s, 3H), 2.99-2.88 (m, 2H), 2.86-2.77 (m, 3H), 2.35-2.28 (m, 8H), 1.69-1.49 (m, 8H), 1.37-1.16 (m, 56H), 1.05 (d, J=6.2 Hz, 6H), 0.88 (t, J=6.8 Hz, 6H).

g) Synthesis of 1-(1,3-Bis(palmitoyloxy)propan-2-yl) 10-(4-(6-hydroxy-3-(4-(2-(piperidin-1-yl)ethoxy)benzoyl)benzo[b]thiophen-2-yl)phenyl) decanedioate (4)

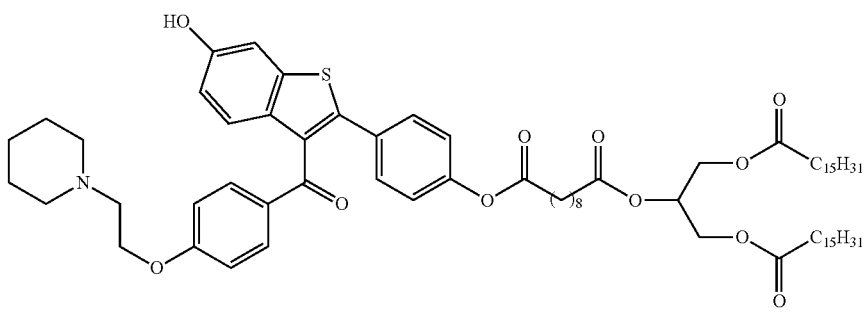

In the case of raloxifene (RAL), which contains two phenolic hydroxyl groups, mono-protection of the parent molecule is necessary to prevent the formation of mixed mono-acyl and bis-acyl products in the subsequent coupling step. Treatment of raloxifene with one equivalent of TBSCl in the presence of base affords a mixture of regioisomeric mono-silyl ethers that can be partially separated by chromatography. Coupling of the less-polar phenol isomer XXVI with acid-TG IV under standard conditions gives protected prodrug XXVII. Removal of the silyl protecting group using TBAF provided Compound 4. It should be noted that the regioisomer of phenol XXVI could also be converted to the corresponding isomeric prodrug using this procedure.

g)(i) (6-((tert-Butyldimethylsilyl)oxy)-2-(4-hydroxyphenyl)benzo[b]thiophen-3-yl)(4-(2-(piperidin-1-yl)ethoxy)phenyl)methanone (XXVI)

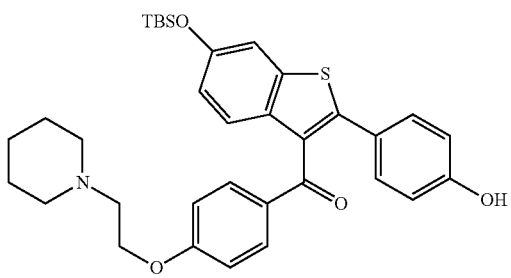 [SMILES: CC(C)(C)[Si](C)(C)Oc1ccc2c(C(=O)c3ccc(OCCN4CCCCC4)cc3)c(-c3ccc(O)cc3)sc2c1]

4-(Dimethylamino)pyridine (DMAP, 108 mg, 0.882 mmol) was added to raloxifene hydrochloride (180 mg, 0.353 mmol) in DMF (10 mL) and the mixture stirred at rt for one hour. The reaction was cooled to 0° C., tert-butyl (chloro)dimethylsilane (TBSCl, 53.2 mg, 0.353 mmol) was added and the resulting mixture stirred at rt for a further 2.5 hours. The reaction was diluted with ethyl acetate (60 mL) and the organic phase washed with water (2×50 mL), sat. aq. NaHCO$_3$ (50 mL) and brine (50 mL), dried (MgSO$_4$) and concentrated under reduced pressure to give the crude product. Purification by silica gel chromatography (0% to 12.5% MeOH/CH$_2$Cl$_2$ with 1% Et$_3$N) gave the protected mono-silyl ether XXVI (25.0 mg, 12%) as a yellow oil, along with numerous fractions of mixed regioisomeric mono-silyl ethers and unreacted raloxifene.

$^1$H NMR (400 MHz, CDCl$_3$) δ 7.68 (d, J=8.8 Hz, 2H), 7.47 (d, J=8.7 Hz, 1H), 7.30 (d, J=2.0 Hz, 1H), 7.22 (d, J=8.5 Hz, 2H), 6.87 (dd, J=8.7, 2.0 Hz, 1H), 6.65 (d, J=7.9 Hz, 4H), 4.06 (t, J=5.9 Hz, 2H), 2.75 (t, J=5.9 Hz, 2H), 2.55-2.47 (m, 4H), 1.65-1.58 (m, 4H), 1.48-1.41 (m, 2H), 0.92 (s, 9H), 0.11 (s, 6H).

g)(ii) 1-(1,3-Bis(palmitoyloxy)propan-2-yl) 10-(4-(6-((tert-butyldimethylsilyl)oxy)-3-(4-(2-(piperidin-1-yl)ethoxy)benzoyl)benzo[b]thiophen-2-yl)phenyl) decanedioate (XXVII)

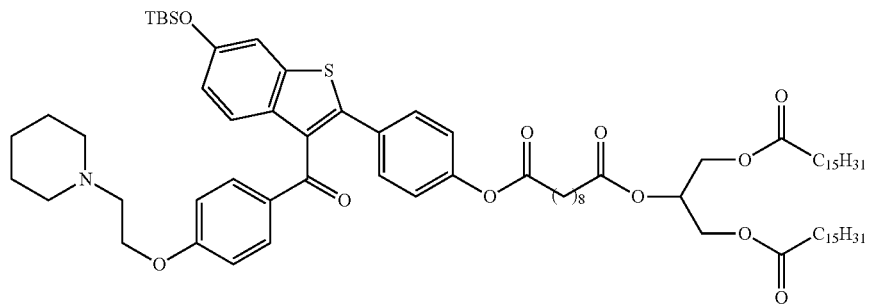

4-(Dimethylamino)pyridine (DMAP, 2.4 mg, 19.9 μmol) and EDC.HCl (9.5 mg, 49.8 mol) were added to a solution of acid-TG IV (15.0 mg, 19.9 μmol) and XXVI (11.7 mg, 19.9 μmol) in CH$_2$Cl$_2$ (0.6 mL) and the mixture stirred at rt for six hours. The reaction was diluted with CH$_2$Cl$_2$ (5 mL), silica gel was added and the mixture concentrated under reduced pressure. Purification by silica gel chromatography (0% to 1.5% MeOH/CH$_2$Cl$_2$ with 1% Et$_3$N) gave the protected prodrug XXVII (16.0 mg, 61%) as a colourless oil.

$^1$H NMR (400 MHz, CDCl$_3$) δ 7.74-7.67 (m, 3H), 7.59 (d, J=2.1 Hz, 1H), 7.30-7.23 (m, 2H), 7.06 (dd, J=8.8, 2.1 Hz, 1H), 6.73 (d, J=8.8 Hz, 2H), 6.67 (d, J=8.6 Hz, 2H), 5.26 (m, 1H), 4.29 (dd, J=11.9, 4.3 Hz, 2H), 4.14 (dd, J=11.9, 5.9 Hz, 2H), 4.07 (t, J=6.0 Hz, 2H), 2.74 (t, J=5.9 Hz, 2H), 2.58 (t, J=7.5 Hz, 2H), 2.53-2.44 (m, 4H), 2.35-2.27 (m, 6H), 1.82-1.73 (m, 2H), 1.68-1.53 (m, 10H), 1.49-1.39 (m, 4H), 1.38-1.19 (m, 54H), 0.93 (s, 9H), 0.87 (t, J=6.8 Hz, 6H), 0.12 (s, 6H).

g)(iii) 1-(1,3-Bis(palmitoyloxy)propan-2-yl) 10-(4-(6-hydroxy-3-(4-(2-(piperidin-1-yl)ethoxy)benzoyl)benzo[b]thiophen-2-yl)phenyl) decanedioate (4)

Tetra-n-butylammonium fluoride (TBAF, 0.1 M in THF, 70.0 μL, 7.0 μmol) and acetic acid (1.0 M in THF, 10.0 μL, 10.0 μmol) were added to a solution of TBS ether XXVII (7.1 mg, 5.4 μmol) in THF (0.4 mL) at 0° C. and the mixture was stirred at 0° C. for 50 minutes. The reaction was diluted with ethyl acetate (20 mL), washed with water and brine (15 mL), dried (MgSO$_4$) and concentrated under reduced pressure to give the crude product. Purification by silica gel chromatography (0% to 2% MeOH/CH$_2$Cl$_2$ with 1% Et$_3$N) gave Compound 4 (4.9 mg, 75%) as a pale yellow oil.

$^1$H NMR (400 MHz, CDCl$_3$) δ 7.77 (d, J=8.8 Hz, 1H), 7.66 (d, J=8.9 Hz, 2H), 7.59 (d, J=2.1 Hz, 1H), 7.19 (d, J=8.6 Hz, 2H), 7.08 (dd, J=8.8, 2.2 Hz, 1H), 6.67 (d, J=7.3 Hz, 2H), 6.61 (d, J=8.6 Hz, 2H), 5.26 (m, 1H), 4.30 (dd, J=11.9, 4.3 Hz, 2H), 4.15 (dd, J=11.9, 5.9 Hz, 2H), 4.09 (t, J=5.7 Hz, 2H), 2.77 (t, J=5.8 Hz, 2H), 2.62-2.50 (m, 6H), 2.37-2.27 (m, 6H), 1.82-1.73 (m, 2H), 1.69-1.55 (m, 10H), 1.50-1.19 (m, 58H), 0.87 (t, J=6.8 Hz, 6H).

Example 2. Methods for Preparing Compounds of the Formula (I) Wherein Y Represents an α-Methyl Substituted Alkyl Group and L Represents X' where X' is O h) (E)-Methyl 10-(benzyloxy)-2-methyldec-2-enoate (VIII)

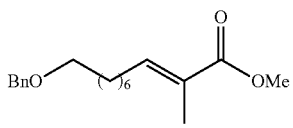

Pyridinium chlorochromate (PCC, 39.7 mg, 0.184 mmol) and Celite (30 mg) were added to a solution of alcohol VI (29.0 mg, 0.123 mmol) in CH$_2$Cl$_2$ (1.5 mL) and the reaction stirred at rt for 1.5 hours. The resulting dark suspension was filtered through a short pad of silica gel, eluting with 50% ethyl acetate/hexanes, and the eluent concentrated under reduced pressure to give the crude aldehyde, which was immediately re-dissolved in toluene (1.5 mL). Ylide VII (85.5 mg, 0.245 mmol) was added and the mixture heated at reflux for 20 hours. The reaction was cooled to rt and concentrated under reduced pressure to give the crude product. Purification by silica gel chromatography (5% to 8% ethyl acetate/hexanes) gave α,β-unsaturated methyl ester VIII (26.2 mg, 70%) as a yellow oil.

$^1$H NMR (400 MHz, CDCl$_3$) δ 7.38-7.26 (m, 5H), 6.76 (m, 1H), 4.50 (s, 2H), 3.73 (s, 3H), 3.46 (t, J=6.6 Hz, 2H), 2.10-2.02 (m, 2H), 1.83 (d, J=1.3 Hz, 3H), 1.65-1.58 (m, 2H), 1.47-1.28 (m, 8H).

i) (E)-10-(Benzyloxy)-2-methyldec-2-enoic acid (IX)

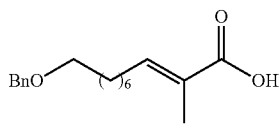

A solution of sodium hydroxide (2.0 M, 256 µL, 0.512 mmol) was added to ester VIII (26.0 mg. 0.0854 mmol) in methanol (0.9 mL) and water (0.65 mL) and the mixture stirred at rt for 30 minutes, then at 0° C. for 20 hours. The reaction was acidified to pH 1 by addition of 1 M HCl, diluted with water (5 mL) and the aqueous phase extracted with ethyl acetate (4×15 mL). The combined organic extracts were washed with brine (40 mL), dried (MgSO$_4$) and concentrated under reduced pressure to give the crude acid IX (24.8 mg, quant.) as a colourless oil that was used without purification.

$^1$H NMR (400 MHz, CDCl$_3$) δ 7.39-7.26 (m, 5H), 6.91 (td, J=7.5, 1.3 Hz, 1H), 4.51 (s, 2H), 3.47 (t, J=6.6 Hz, 2H), 2.23-2.15 (m, 2H), 1.83 (d, J=0.7 Hz, 3H), 1.67-1.56 (m, 2H), 1.49-1.25 (m, 8H).

j) (E)-2-((10-(Benzyloxy)-2-methyldec-2-enoyl)oxy)propane-1,3-diyl dipalmitate (X)

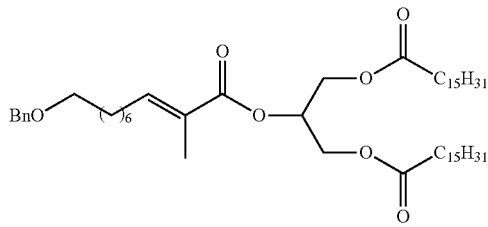

4-(Dimethylamino)pyridine (DMAP, 10.4 mg, 0.0854 mmol), EDC.HCl (40.9 mg, 0.214 mmol) and diglyceride III (77.7 mg, 0.137 mmol) were added to a solution of acid IX (24.8 mg, 0.0854 mmol) in CH$_2$Cl$_2$ (2 mL) and the mixture stirred at rt for 17 hours. The reaction was diluted with CH$_2$Cl$_2$ (5 mL), silica gel was added and the mixture concentrated under reduced pressure. Purification by silica gel chromatography (3% to 7.5% ethyl acetate/hexanes) gave triglyceride X (44.6 mg, 62% over two steps) as a colourless solid.

$^1$H NMR (400 MHz, CDCl$_3$) δ 7.37-7.24 (m, 5H), 6.76 (m, 1H), 5.30 (m, 1H), 4.50 (s, 2H), 4.31 (dd, J=11.8, 4.5 Hz, 2H), 4.22 (dd, J=11.8, 5.8 Hz, 2H), 3.46 (t, J=6.6 Hz, 2H), 2.31 (t, J=7.5 Hz, 4H), 2.16 (dt, J=7.4, 7.4 Hz, 2H), 1.81 (d, J=1.1 Hz, 3H), 1.66-1.55 (m, 6H), 1.47-1.19 (m, 56H), 0.88 (t, J=6.9 Hz, 6H).

k) 2-((10-Hydroxy-2-methyldecanoyl)oxy)propane-1,3-diyl dipalmitate (XI)

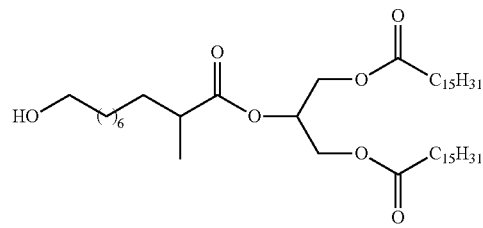

A solution of benzyl ether X (40.0 mg, 47.6 µmol) in ethyl acetate (5 mL) in a three-neck flask was twice evacuated and flushed with N$_2$ gas, then palladium on carbon (10% w/w, 12.7 mg, 11.9 µmol) was added and the resulting suspension re-evacuated and flushed with N$_2$ twice. The flask was fitted with a H$_2$ balloon, evacuated and flushed with H$_2$ three times and the reaction mixture stirred at rt under 1 atm of H$_2$ for three hours. The reaction was filtered through a pad of Celite, washing with ethyl acetate, and concentrated under reduced pressure to give saturated alcohol XI (32.1 mg) as a colourless oil that was used without purification.

$^1$H NMR (400 MHz, CDCl$_3$) δ 5.27 (m, 1H), 4.29 (dd, J=11.7, 3.9 Hz, 2H), 4.14 (dd, J=11.9, 6.1 Hz, 2H), 3.63 (t, J=6.6 Hz, 2H), 2.44 (m, 1H), 2.30 (t, J=7.6 Hz, 4H), 1.67-1.50 (m, 8H), 1.42-1.20 (m, 58H), 1.14 (d, J=7.0 Hz, 3H), 0.88 (t, J=6.9 Hz, 6H).

l) 2-((2-Methyl-10-oxodecanoyl)oxy)propane-1,3-diyl dipalmitate (XII)

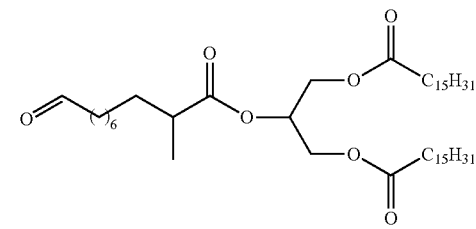

Pyridinium chlorochromate (PCC, 15.2 mg, 70.4 µmol) was added to a suspension of alcohol XI (26.5 mg, 35.2 µmol) and Celite (20 mg) in CH$_2$Cl$_2$ (1 mL) at 0° C. and the mixture stirred at rt for one hour. The reaction was filtered through a short pad of silica gel, eluting with 50% ethyl acetate/hexanes, and the filtrate concentrated under reduced pressure to give crude aldehyde XII (26.4 mg) as a yellow oil that was used without purification.

$^1$H NMR (400 MHz, CDCl$_3$) δ 9.76 (t, J=1.8 Hz, 1H), 5.27 (m, 1H), 4.29 (ddd, J=11.9, 4.3, 3.1 Hz, 2H), 4.14 (dd, J=11.9, 6.1 Hz, 2H), 2.42 (m, 1H), 2.41 (td, J=7.3, 1.8 Hz, 2H), 2.30 (t, J=7.5 Hz, 4H), 1.67-1.54 (m, 8H), 1.44-1.18 (m, 56H), 1.14 (d, J=7.0 Hz, 3H), 0.88 (t, J=6.9 Hz, 6H).

m) 10-((1,3-Bis(palmitoyloxy)propan-2-yl)oxy)-9-methyl-10-oxodecanoic acid (IV)

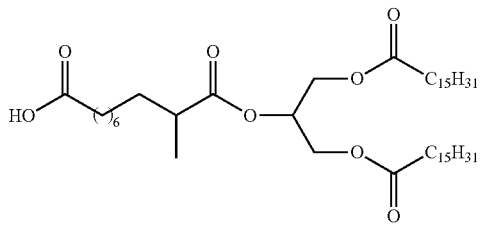

A solution of sodium chlorite (28.6 mg, 0.317 mmol) and sodium phosphate monobasic (NaH$_2$PO$_4$, 29.5 mg, 0.246 mmol) in water (0.5 mL) was added dropwise to aldehyde XII (26.4 mg, 0.0352 mmol) in t-BuOH (1 mL) and 2,3-dimethyl-2-butene (0.2 mL) and the reaction stirred at rt for 1.5 hours. The reaction was diluted with water (5 mL) and the aqueous layer extracted with hexanes (3×5 mL). The combined organic extracts were dried (MgSO$_4$) and concentrated under reduced pressure to give crude acid IV (27.0 mg) as a colourless oil that was used without purification.

$^1$H NMR (400 MHz, CDCl$_3$) δ 5.27 (m, 1H), 4.29 (ddd, J=11.8, 4.3, 3.2 Hz, 2H), 4.14 (dd, J=11.9, 6.1 Hz, 2H), 2.43 (m, 1H), 2.36-2.28 (m, 6H), 1.65-1.55 (m, 8H), 1.38-1.19 (m, 56H), 1.14 (d, J=7.0 Hz, 3H), 0.88 (t, J=7.0 Hz, 6H).

Example 3. Methods for Preparing Compounds of the Formula (I) Wherein Y Represents a β-Methyl Substituted Alkyl Group and L Represents X' where X' is O n) (7-(Benzyloxy)hept-1-yn-1-yl)trimethylsilane (XIV)

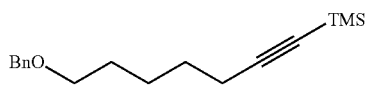 [SMILES: C[Si](C)(C)C#CCCCCCOCc1ccccc1]

n-Butyllithium (n-BuLi, 1.6 M in hexanes, 765 μL, 1.23 mmol) was added slowly to a solution of TMS-acetylene (198 μL, 1.40 mmol) in THF (1.5 mL) at −78° C. and the mixture stirred at −78° C. for five minutes then warmed to rt and stirred for a further 15 minutes. The reaction was re-cooled to −50° C., a solution of bromide XIII (90.0 mg, 0.350 mmol) in THF (1 mL) was added drop wise and the mixture stirred at −50° C. for 15 minutes and then at rt for 17 hours. The reaction was diluted with brine (15 mL) and the aqueous phase extracted with ethyl acetate (3×15 mL). The combined organic extracts were washed with brine (30 mL), dried (MgSO$_4$) and concentrated under reduced pressure to give the crude product. Purification by silica gel chromatography (4% to 5% ethyl acetate/hexanes) gave TMS alkyne XIV (45.9 mg, 48%) as a colourless oil also containing desilylated alkyne XV (9.7 mg, 14% by $^1$H NMR integration) and small amounts of PPh$_3$.

$^1$H NMR (400 MHz, CDCl$_3$) δ 7.37-7.26 (m, 5H), 4.50 (s, 2H), 3.48 (t, J=6.5 Hz, 2H), 2.23 (t, J=7.0 Hz, 2H), 1.68-1.60 (m, 2H), 1.58-1.42 (m, 4H), 0.14 (s, 7H).

o) ((Hept-6-yn-1-yloxy)methyl)benzene (XV)

Tetrabutylammonium fluoride (TBAF, 1.0 M in THF, 201 μL, 0.201 mmol) was added dropwise to a 7:2 mixture of silylalkyne XIV and alkyne XV (55.6 mg combined, 0.215 mmol) in THF (1 mL) at 0° C. and the mixture stirred at rt for one hour. The reaction was diluted with water (5 mL) and sat. aq. NH$_4$Cl (3 mL) and the aqueous phase extracted with ethyl acetate (3×10 mL). The combined organic extracts were washed with brine (20 mL), dried (MgSO$_4$) and concentrated under reduced pressure to give the crude product. Purification by silica gel chromatography (4% ethyl acetate/hexanes) gave alkyne XV (37.5 mg, 53% over two steps) as a colourless oil.

$^1$H NMR (400 MHz, CDCl$_3$) δ 7.39-7.27 (m, 5H), 4.51 (s, 2H), 3.49 (t, J=6.5 Hz, 2H), 2.21 (td, J=6.9, 2.6 Hz, 2H), 1.95 (t, J=2.7 Hz, 1H), 1.70-1.61 (m, 2H), 1.60-1.48 (m, 4H).

p) (Z)-Ethyl 10-(benzyloxy)-3-methyldec-2-en-4-ynoate (XVII)

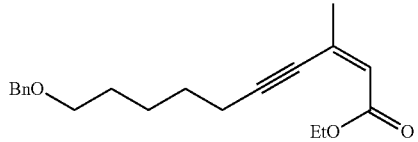 [SMILES: CCOC(=O)/C=C(/C)C#CCCCCCOCc1ccccc1]

A suspension of PdCl$_2$(PPh$_3$)$_2$ (16.8 mg, 0.0240 mmol) in DMF (1.5 mL) was degassed using N$_2$ gas for five minutes, and then CuI (9.1 mg, 0.0480 mmol), Et$_3$N (66.8 μL, 0.480 mmol) and a degassed solution of alkyne XV (48.5 mg, 0.240 mmol) and enol triflate XVI (94.3 mg, 0.360 mmol) in DMF (2 mL) were added. The mixture was degassed using a stream of N$_2$ for a further five minutes and then heated at 0° C. for one hour. The reaction was cooled to rt, diluted with ethyl acetate (30 mL), washed with 1 M HCl, sat. aq. NaHCO$_3$, water and brine (20 mL each), dried (MgSO$_4$) and concentrated under reduced pressure to give the crude product. Silica gel chromatography (4% to 5% ethyl acetate/hexanes) gave enyne XVII (46.6 mg, 62%) as a pale yellow oil.

$^1$H NMR (400 MHz, CDCl$_3$) δ 7.37-7.24 (m, 5H), 5.92 (m, 1H), 4.50 (s, 2H), 4.17 (q, J=7.1 Hz, 2H), 3.48 (t, J=6.5 Hz, 2H), 2.45 (t, J=7.0 Hz, 2H), 2.01 (d, J=1.4 Hz, 3H), 1.69-1.59 (m, 4H), 1.56-1.49 (m, 2H), 1.27 (t, J=7.1 Hz, 3H).

q) Ethyl 10-hydroxy-3-methyldecanoate (XVIII)

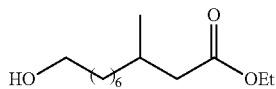

A solution of benzyl ether XVII (31.4 mg, 0.100 mmol) in ethyl acetate (8 mL) in a two-neck flask was twice evacuated and flushed with N₂ gas, then palladium on carbon (10% w/w, 26.6 mg, 0.0250 mmol) was added and the resulting suspension re-evacuated and flushed with N₂ three times. The flask was fitted with a H₂ balloon, evacuated and flushed with H₂ three times and the reaction mixture stirred at rt under 1 atm of H₂ for one hour. The reaction was filtered through a pad of Celite, washing with ethyl acetate, and concentrated under reduced pressure to give saturated alcohol XVIII (23.0 mg, quant.) as a colourless oil that was used without purification.

$^1$H NMR (400 MHz, CDCl₃) δ 4.12 (q, J=7.1 Hz, 2H), 3.63 (t, J=6.6 Hz, 2H), 2.28 (dd, J=14.6, 6.1 Hz, 1H), 2.09 (dd, J=14.6, 8.1 Hz, 1H), 1.94 (m, 1H), 1.60-1.50 (m, 2H), 1.25 (t, J=6.6 Hz, 3H), 1.40-1.13 (m, 10H), 0.92 (d, J=6.6 Hz, 3H).

r) Ethyl 10-((tert-butyldiphenylsilyl)oxy)-3-methyldecanoate (XIX)

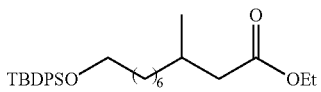

Imidazole (9.6 mg, 0.141 mmol) and tert-butyl(chloro)diphenylsilane (TBDPSCl, 50.8 μL, 0.195 mmol) were added to a solution of alcohol XVIII (18.0 mg, 0.0781 mmol) in DMF (3 mL) and the mixture stirred at rt for 16 hours. The reaction was diluted with ethyl acetate (20 mL), washed with brine (2×15 mL), dried (MgSO₄) and concentrated under reduced pressure to give the crude product. Purification by silica gel chromatography (4% ethyl acetate/hexanes with 0.5% Et₃N) gave TBDPS ether XIX (33.7 mg, 92%) as a colourless oil.

$^1$H NMR (400 MHz, CDCl₃) δ 7.70-7.64 (m, 4H), 7.45-7.33 (m, 6H), 4.13 (q, J=7.1 Hz, 2H), 3.65 (t, J=6.5 Hz, 2H), 2.28 (dd, J=14.6, 6.0 Hz, 1H), 2.09 (dd, J=14.6, 8.2 Hz, 1H), 1.94 (m, 1H), 1.60-1.50 (m, 2H), 1.38-1.21 (m, 3H), 1.05 (s, J=2.9 Hz, 2H), 1.05 (s, 9H), 0.93 (d, J=6.6 Hz, 3H).

s) 10-((tert-Butyldiphenylsilyl)oxy)-3-methyldecanoic acid (XX)

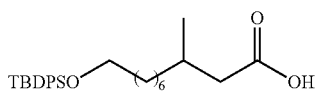

A solution of potassium hydroxide (2.0 M, 427 μL, 0.853 mmol) was added to ester XIX (40.0 mg. 0.0853 mmol) in ethanol (2 mL) and the mixture heated at 80° C. for two hours. The reaction was acidified to pH 1 by addition of 1 M HCl and the organic solvent removed under reduced pressure. The residue was diluted with water (5 mL), the aqueous phase extracted with ethyl acetate (3×15 mL) and the combined organic extracts washed with brine (30 mL), dried (MgSO₄) and concentrated under reduced pressure to give the crude acid XX (37.6 mg, quant.) as a colourless oil that was used without purification. When run at high concentration, a doubling of signals in both the $^1$H and 13C NMR spectra was observed (4:1 ratio), suggesting the possible presence of both the monomeric and dimeric species in solution.

$^1$H NMR (400 MHz, CDCl₃) δ 7.74-7.63 (m, 4H), 7.45-7.34 (m, 6H), 3.65 (t, J=6.5 Hz, 2H), 2.35 (dd, J=15.0, 5.9 Hz, 1H), 2.14 (dd, J=15.0, 8.2 Hz, 1H), 1.95 (m, 1H), 1.61-1.50 (m, 2H), 1.38-1.18 (m, 10H), 1.04 (s, 9H), 0.96 (d, J=6.6 Hz, 3H).

t) 2-((10-((tert-Butyldiphenylsilyl)oxy)-3-methyldecanoyl)oxy)propane-1,3-diyl dipalmitate (XXI)

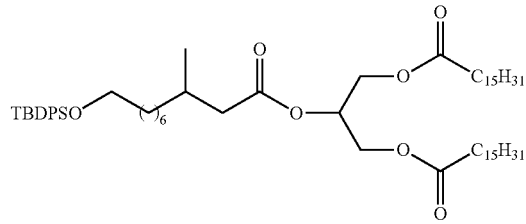

4-(Dimethylamino)pyridine (DMAP, 10.1 mg, 0.0831 mmol), EDC.HCl (39.8 mg, 0.208 mmol) and diglyceride III (70.9 mg, 0.125 mmol) were added to a solution of acid XX (36.6 mg, 0.0831 mmol) in CH₂Cl₂ (2.5 mL) and the mixture stirred at rt for 21 hours. The reaction was diluted with CH₂Cl₂ (5 mL), silica gel was added and the mixture concentrated under reduced pressure. Purification by silica gel chromatography (4% to 5% ethyl acetate/hexanes) gave triglyceride XXI (39.9 mg, 48% over two steps) as a colourless solid.

$^1$H NMR (400 MHz, CDCl₃) δ 7.69-7.64 (m, 4H), 7.44-7.34 (m, 6H), 5.28 (m, 1H), 4.29 (ddd, J=11.8, 4.2, 0.6 Hz, 2H), 4.14 (dd, J=12.0, 5.9 Hz, 2H), 3.65 (t, J=6.5 Hz, 2H), 2.37-2.27 (m, 5H), 2.11 (dd, J=14.7, 8.4 Hz, 1H), 1.92 (m, 1H), 1.67-1.50 (m, 8H), 1.39-1.14 (m, 56H), 1.04 (s, 9H), 0.93 (d, J=6.6 Hz, 3H), 0.88 (t, J=6.9 Hz, 6H).

u) 2-((10-Hydroxy-3-methyldecanoyl)oxy)propane-1,3-diyl dipalmitate (XI)

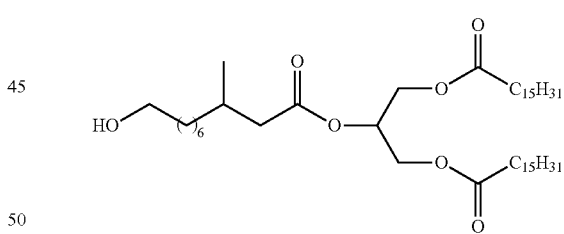

Tetrabutylammonium fluoride (TBAF, 1.0 M in THF, 98.3 μL, 98.3 μmol) was added to a solution of TBDPS ether XXI (39.0 mg, 39.3 μmol) in THF (2.5 mL) at 0° C. and the mixture stirred at rt for three hours. The reaction was diluted with water (10 mL), extracted with ethyl acetate (3×15 mL), and the organic extracts washed with brine (30 mL), dried (MgSO₄) and concentrated under reduced pressure to give the crude product. Purification by silica gel chromatography (10% to 20% ethyl acetate/hexanes) gave alcohol XI (21.8 mg, 74%) as a colourless solid.

$^1$H NMR (400 MHz, CDCl₃) δ 5.28 (m, 1H), 4.29 (dd, J=11.9, 4.3 Hz, 2H), 4.14 (dd, J=11.9, 5.9 Hz, 2H), 3.64 (t, J=6.6 Hz, 2H), 2.36-2.27 (m, 5H), 2.12 (dd, J=14.7, 8.2 Hz, 1H), 1.93 (m, 1H), 1.65-1.52 (m, 6H), 1.39-1.16 (m, 58H), 0.93 (d, J=6.6 Hz, 3H), 0.88 (t, J=6.9 Hz, 6H).

v) 2-((3-Methyl-10-oxodecanoyl)oxy)propane-1,3-diyl dipalmitate (XII)

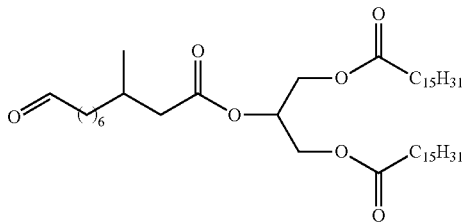

Pyridinium chlorochromate (PCC, 12.0 mg, 55.8 µmol) was added to a suspension of alcohol XI (21.0 mg, 27.9 µmol) and Celite (15 mg) in CH$_2$Cl$_2$ (1.5 mL) at 0° C. and the mixture stirred at rt for 1.75 hours. The reaction was filtered through a short pad of silica gel, eluting with ethyl acetate, and the filtrate concentrated under reduced pressure to give crude aldehyde XII (20.9 mg, quant.) as a yellow oil that was used without purification.

$^1$H NMR (400 MHz, CDCl$_3$) δ 9.76 (s, 1H), 5.28 (m, 1H), 4.29 (dd, J=11.6, 3.5 Hz, 2H), 4.14 (dd, J=11.6, 5.7 Hz, 2H), 2.42 (t, J=7.1 Hz, 2H), 2.36-2.25 (m, 5H), 2.12 (dd, J=14.5, 8.3 Hz, 1H), 1.93 (m, 1H), 1.72-1.53 (m, 6H), 1.42-1.05 (m, 56H), 0.93 (d, J=6.5 Hz, 3H), 0.88 (t, J=6.6 Hz, 6H).

w) 10-((1,3-Bis(palmitoyloxy)propan-2-yl)oxy)-8-methyl-10-oxodecanoic acid (IV)

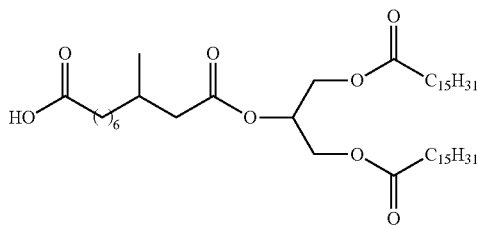

A solution of sodium chlorite (22.7 mg, 0.251 mmol) and sodium phosphate monobasic (NaH$_2$PO$_4$, 23.4 mg, 0.195 mmol) in water (1 mL) was added dropwise to aldehyde XII (20.9 mg, 0.0279 mmol) in t-BuOH (1.5 mL) and 2,3-dimethyl-2-butene (0.3 mL) and the reaction stirred at rt for 2.25 hours. The reaction was diluted with water (10 mL) and the aqueous layer extracted with ethyl acetate (3×15 mL). The combined organic extracts were washed with brine (30 mL), dried (MgSO$_4$) and concentrated under reduced pressure to give the crude product. Purification by silica gel chromatography (10% to 20% ethyl acetate/hexanes with 0.5% AcOH) gave acid IV (16.1 mg, 75%) as a colourless solid.

$^1$H NMR (400 MHz, CDCl$_3$) δ 5.27 (m, 1H), 4.29 (dd, J=11.9, 4.3 Hz, 2H), 4.14 (dd, J=12.0, 6.0 Hz, 2H), 2.37-2.27 (m, 7H), 2.12 (dd, J=14.7, 8.2 Hz, 1H), 1.93 (m, 1H), 1.67-1.55 (m, 6H), 1.40-1.14 (m, 56H), 0.93 (d, J=6.6 Hz, 3H), 0.88 (t, J=6.9 Hz, 6H).

x) 1-(1,3-Bis(palmitoyloxy)propan-2-yl) 10-((8R,9S,10R,13S,14S,17S)-10,13-dimethyl-3-oxo-2,3,6,7,8,9,10,11,12,13,14,15,16,17-tetradecahydro-1H-cyclopenta[a]phenanthren-17-yl) 3-methyldecanedioate (19)

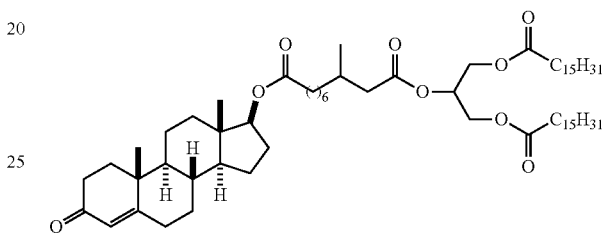

4-(Dimethylamino)pyridine (DMAP, 2.5 mg, 20.6 µmol), EDC.HCl (9.9 mg, 51.4 µmol) and testosterone (10.7 mg, 37.1 µmol) were added to a solution of acid-TG IV (13.6 mg, 17.7 µmol) in CH$_2$Cl$_2$ (1 mL) and the mixture stirred at rt for 17 hours. The reaction was diluted with CH$_2$Cl$_2$ (5 mL), silica gel was added and the mixture concentrated under reduced pressure. Purification by silica gel chromatography (15% ethyl acetate/hexanes) gave Compound 19 (10.1 mg, 55%) as a colourless solid.

$^1$H NMR (400 MHz, CDCl$_3$) δ 5.73 (s, 1H), 5.27 (m, 1H), 4.61 (dd, J=9.0, 7.9 Hz, 1H), 4.29 (dd, J=11.9, 3.8 Hz, 2H), 4.14 (dd, J=11.9, 6.0 Hz, 2H), 2.48-2.24 (m, 11H), 2.23-1.99 (m, 4H), 1.93 (m, 1H), 1.85 (m, 1H), 1.77 (m, 1H), 1.72-1.22 (m, 68H), 1.19 (s, 3H), 1.16-0.96 (m, 4H), 0.93 (d, J=6.6 Hz, 3H), 0.88 (t, J=6.9 Hz, 6H), 0.83 (s, 3H).

Further exemplary compounds of the formula (I) are provided below in Table 4.

TABLE 4

$^1$H NMR data for representative compounds of formula:

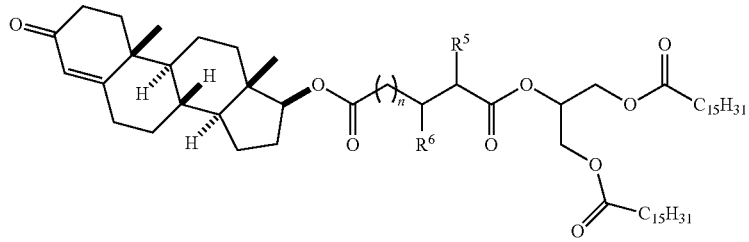

| Compound No. | R$^5$ | R$^6$ | n | $^1$H NMR (400 MHz, CDCl$_3$) |
|---|---|---|---|---|
| 10 | H | H | 1 | δ 5.73 (s, 1H), 5.26 (m, 1H), 4.61 (dd, J = 8.9, 8.0 Hz, 1H), 4.30 (dd, J = 11.9, 4.4 Hz, 2H), 4.14 (dd, J = 11.9, 5.9 Hz, 2H), 2.47-2.12 (m, 12H), 2.02 (m, 1H), 1.94 (t, J = 7.2 Hz, 2H), 1.89-1.34 (m, 15H), 1.34-1.20 (m, 48H), 1.19 (s, 3H), 1.11-0.91 (m, 3H), 0.88 (t, J = 6.8 Hz, 6H), 0.83 (s, 3H) |

TABLE 4-continued $^1$H NMR data for representative compounds of formula:

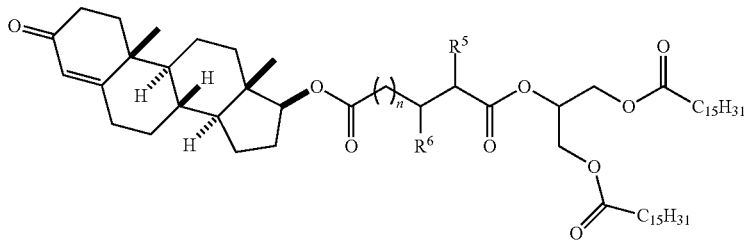

| Compound No. | $R^5$ | $R^6$ | n | $^1$H NMR (400 MHz, CDCl$_3$) |
|---|---|---|---|---|
| 11 | H | H | 2 | δ 5.72 (s, 1H), 5.25 (m, 1H), 4.60 (dd, J = 9.0, 7.9 Hz, 1H), 4.29 (dd, J = 11.9, 4.3 Hz, 2H), 4.13 (dd, J = 11.9, 5.9 Hz, 2H), 2.48-2.23 (m, 12H), 2.17 (m, 1H), 2.02 (ddd, J = 13.4, 4.8, 3.0 Hz, 1H), 1.85 (m, 1H), 1.76 (m, 1H), 1.73-1.34 (m, 15H), 1.32-1.21 (m, 48H), 1.18 (s, 3H), 1.12-0.90 (m, 4H), 0.87 (t, J = 6.8 Hz, 6H), 0.83 (s, 3H). |
| 12 | H | H | 4 | δ 5.73 (s, 1H), 5.25 (m, 1H), 4.60 (dd, J = 9.1, 7.9 Hz, 1H), 4.29 (dd, J = 11.9, 4.4 Hz, 2H), 4.14 (dd, J = 11.9, 5.9 Hz, 2H), 2.47-2.23 (m, 12H), 2.18 (dtd, J = 13.7, 9.4, 6.2 Hz, 1H), 2.02 (ddd, J = 8.1, 4.8, 2.8 Hz, 1H), 1.85 (m, 1H), 1.77 (m, 1H), 1.72-1.39 (m, 15H), 1.38-1.21 (m, 52H), 1.19 (s, 3H), 1.16-0.91 (m, 4H), 0.88 (t, J = 6.9 Hz, 6H), 0.83 (s, 3H). |
| 13 | H | H | 6 | δ 5.73 (s, 1H), 5.26 (m, 1H), 4.61 (dd, J = 9.0, 7.9 Hz, 1H), 4.29 (dd, J = 11.9, 4.4 Hz, 2H), 4.14 (dd, J = 11.9, 5.9 Hz, 2H), 2.47-2.25 (m, 12H), 2.17 (m, 1H), 2.02 (ddd, J = 13.4, 4.9, 3.3 Hz, 1H), 1.85 (m, 1H), 1.77 (m, 1H), 1.73-1.35 (m, 15H), 1.35-1.21 (m, 56H), 1.19 (s, 3H), 1.16-0.91 (m, 4H), 0.88 (t, J = 6.7 Hz, 6H), 0.83 (s, 3H). |
| 14 | H | H | 8 | δ 5.72 (s, 1H), 5.25 (dq, J = 5.9, 4.4 Hz, 1H), 4.60 (dd, J = 9.1, 7.9 Hz, 1H), 4.29 (dd, J = 11.9, 4.3 Hz, 2H), 4.14 (dd, J = 11.9, 5.9 Hz, 2H), 2.47-2.34 (m, 3H), 2.33-2.23 (m, 9H), 2.17 (dtd, J = 13.7, 9.4, 6.2 Hz, 1H), 2.02 (ddd, J = 13.4, 4.9, 3.2 Hz, 1H), 1.84 (m, 1H), 1.76 (m, 1H), 1.73-1.34 (m, 15H), 1.34-1.20 (m, 60H), 1.18 (s, 3H), 1.16-0.90 (m, 4H), 0.87 (t, J = 6.9 Hz, 6H), 0.83 (s, 3H). |
| 15 | H | H | 14 | δ 5.73 (s, 1H), 5.26 (m, 1H), 4.61 (dd, J = 9.0, 8.0 Hz, 1H), 4.29 (dd, J = 11.9, 4.3 Hz, 2H), 4.14 (dd, J = 11.9, 6.0 Hz, 2H), 2.48-2.24 (m, 12H), 2.17 (m, 1H), 2.02 (ddd, J = 13.3, 4.8, 3.3 Hz, 1H), 1.85 (ddd, J = 8.4, 5.1, 2.6 Hz, 1H), 1.77 (m, 1H), 1.73-1.36 (m, 15H), 1.35-1.21 (m, 72H), 1.19 (s, 3H), 1.16-0.91 (m, 4H), 0.87 (t, J = 6.8 Hz, 6H), 0.83 (s, 3H). |
| 16 | Methyl | H | 6 | δ 5.73 (s, 1H), 5.27 (m, 1H), 4.60 (dd, J = 9.0, 7.9 Hz, 1H), 4.29 (ddd, J = 11.8, 4.2, 3.4 Hz, 2H), 4.14 (dd, J = 11.9, 6.1 Hz, 2H), 2.48-2.34 (m, 4H), 2.33-2.24 (m, 7H), 2.17 (dtd, J = 13.7, 9.4, 6.2 Hz, 1H), 2.02 (ddd, J = 8.1, 4.8, 2.8 Hz, 1H), 1.85 (m, 1H), 1.77 (m, 1H), 1.73-1.36 (m, 15H), 1.35-1.21 (m, 56H), 1.19 (s, 3H), 1.13 (d, J = 7.0 Hz, 3H), 1.10-0.90 (m, 4H), 0.87 (t, J = 6.9 Hz, 6H), 0.83 (s, 3H). |
| 17 | methyl | H | 14 | δ 5.72 (s, 1H), 5.26 (m, 1H), 4.60 (dd, J = 8.9, 8.1 Hz, 1H), 4.28 (dd, J = 11.9, 4.0 Hz, 2H), 4.14 (dd, J = 11.9, 6.1 Hz, 2H), 2.48-2.34 (m, 4H), 2.33-2.24 (m, 7H), 2.17 (m, 1H), 2.02 (ddd, J = 13.3, 4.7, 3.3 Hz, 1H), 1.88-1.74 (m, 3H), 1.74-1.21 (m, 86H), 1.18 (s, 3H), 1.13 (d, J = 7.0 Hz, 3H), 1.10-0.91 (m, 4H), 0.87 (t, J = 6.8 Hz, 6H), 0.83 (s, 3H). |
| 18 | H | methyl | 1 | δ 5.72 (s, 1H), 5.27 (m, 1H), 4.61 (dd, J = 8.5, 8.5 Hz, 1H), 4.29 (dd, J = 11.9, 4.2 Hz, 2H), 4.13 (dd, J = 11.9, 6.0 Hz, 2H), 2.51-2.34 (m, 6H), 2.30 (t, J = 7.3 Hz, 4H), 2.27-2.12 (m, 6H), 2.02 (ddd, J = 13.3, 4.8, 3.3 Hz, 1H), 1.91-1.36 (m, 15H), 1.35-1.20 (m, 48H), 1.18 (s, 3H), 1.02 (d, J = 6.4 Hz, 3H), 1.11-0.90 (m, 3H), 0.87 (t, J = 6.8 Hz, 6H), 0.83 (s, 3H). |

TABLE 4-continued $^{1}$H NMR data for representative compounds of formula:

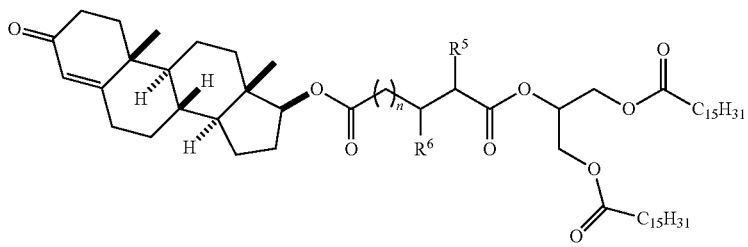

| Compound No. | $R^5$ | $R^6$ | n | $^{1}$H NMR (400 MHz, CDCl$_3$) |
|---|---|---|---|---|
| 20 | H | methyl | 11 | δ 5.73 (s, 1H), 5.27 (m, 1H), 4.61 (dd, J = 9.1, 7.9 Hz, 1H), 4.28 (dd, J = 11.9, 4.3 Hz, 2H), 4.14 (dd, J = 12.0, 5.8 Hz, 2H), 2.47-2.24 (m, 11H), 2.23-2.08 (m, 2H), 2.02 (ddd, J = 13.4, 4.9, 3.3 Hz, 1H), 1.93 (m, 1H), 1.84 (m, 1H), 1.77 (dt, J = 11.9, 3.0 Hz, 1H), 1.74-1.20 (m, 79H), 1.19 (s, 3H), 1.17-0.96 (m, 4H), 0.92 (d, J = 6.6 Hz, 3H), 0.87 (t, J = 6.9 Hz, 6H), 0.83 (s, 3H). |

Example 4. Methods for Preparing Compounds of the Formula (I) Wherein Z Represents C(O)R$^3$ and R$^3$ Represents an Acetal Self-Immolative Group and L Represents X' where X' is O or N(R$^4$)

Scheme 5: Synthesis of a compounds with an acetal self-immolative linker

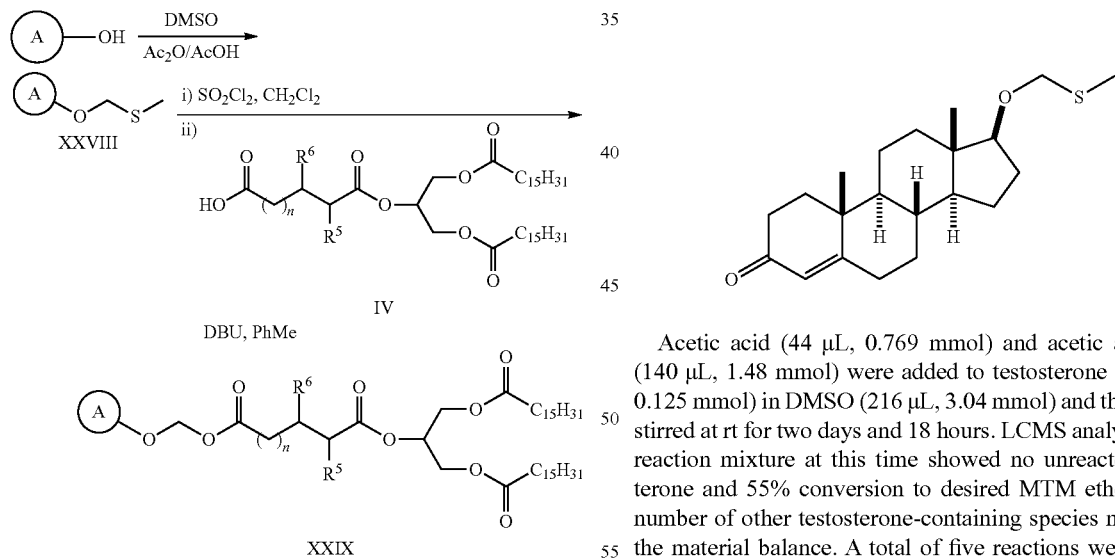

For the synthesis of compounds containing an acetal self-immolative linker placed between the pharmaceutical agent and the alkyl spacer to facilitate systemic release of the parent molecule (Wittman, M. D.; et al, *Bioorg. Med. Chem. Lett.* 2001, 11, 811-814), an alcohol-bearing pharmaceutical agent must be functionalised and activated prior to conjugation with acid-triglyceride IV as outlined in Scheme 5. Treatment of an alcohol with DMSO in a mixture of acetic anhydride and acetic acid results in the formation of (methylthio)methyl (MTM) ether XXVIII. Activation of MTM ether using sulfuryl chloride forms a presumed sulfoxide species that can react with the carboxylate of acid-triglyceride IV to give the acetal-bearing compound XXIX.

y) (8R,9S,10R,13S,14S,17S)-10,13-Dimethyl-17-((methylthio)methoxy)-1,2,6,7,8,9,10,11-12,13,14,15,16,17-tetradecahydro-3H-cyclopenta[a]phenanthren-3-one (XXVIII)

Acetic acid (44 µL, 0.769 mmol) and acetic anhydride (140 µL, 1.48 mmol) were added to testosterone (36.1 mg, 0.125 mmol) in DMSO (216 µL, 3.04 mmol) and the mixture stirred at rt for two days and 18 hours. LCMS analysis of the reaction mixture at this time showed no unreacted testosterone and 55% conversion to desired MTM ether, with a number of other testosterone-containing species making up the material balance. A total of five reactions were carried out on the same scale under slightly different conditions (see Table below), and then combined for isolation of the desired product. The combined reaction mixtures were diluted with water (15 mL) and neutralised using 10% K$_2$CO$_3$ solution. The aqueous phase was extracted with ethyl acetate (3×20 mL) and the combined organic extracts washed with sat. aq. NaHCO$_3$ (40 mL) and brine (40 mL), dried (MgSO$_4$) and concentrated under reduced pressure to give the crude product. Purification by silica gel chromatography (10% to 15% ethyl acetate/hexanes with 1% Et$_3$N) gave testosterone MTM ether XXVIII (113 mg, 52%) as a pale yellow solid.

| Run | Solvent mixture (see below) | Time/temp | Ratio of XXVIII:other products |
|---|---|---|---|
| 1 | A | 16 h @ 40° C. | 46:54 |
| 2 | A | 6 h @ 40° C., then 64 h @ rt | 47:53 |
| 3 | A | 66 h @ rt | 55:45 |
| 4 | B | 6 h @ 40° C., then 64 hr@ rt | 55:45 |
| 5 | B | 66 h @ rt | 47:53 |

Solvent mixtures: A = 54:35:11 v/v DMSO:Ac₂O:AcOH (400 μL total)
B = 1.2:1:0.8 v/v DMSO:Ac₂O:AcOH (375 μL total)

¹H NMR (400 MHz, CDCl₃) δ 5.73 (s, 1H), 4.67 (d, J=11.2 Hz, 1H), 4.58 (d, J=11.2 Hz, 1H), 3.68 (t, J=8.4 Hz, 1H), 2.48-2.24 (m, 4H), 2.13 (s, 3H), 2.08-1.97 (m, 2H), 1.93-1.80 (m, 2H), 1.75-1.22 (m, 8H), 1.19 (s, 3H), 1.07-0.90 (m, 3H), 0.82 (s, 3H).

z) 1,3-Bis(palmitoyloxy)propan-2-yl (((8R,9S,10R,13S,14S,17S)-10,13-dimethyl-3-oxo-2,3,6,7-8,9,10,11,12,13,14-15,16,17-tetradecahydro-1H-cyclopenta[a]phenanthren-17-yl)oxy)methyl adipate (21)

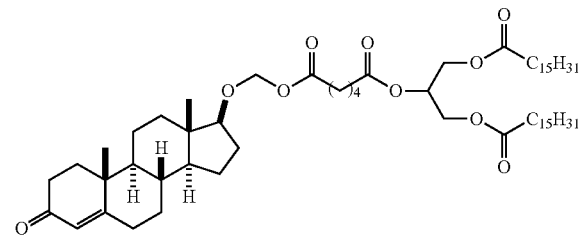

Sulfuryl chloride (0.81 M in CH₂Cl₂, 100 μL, 80.9 μmol) was added to a solution of MTM ether XXVIII (22.3 mg, 63.9 μmol) in CH₂Cl₂ (0.8 mL) at 0° C. and the reaction stirred at 0° C. for 30 minutes and then at rt for a further hour. The reaction was concentrated under a stream of N₂ and dried under reduced pressure. This crude residue was then re-dissolved in CH₂Cl₂ (0.8 mL) and added to a solution of acid-TG IV (29.7 mg, 42.6 μmol) and DBU (7.6 μL, 51.1 μmol) in toluene (0.8 mL) that had been pre-stirred for 20 minutes, and the mixture stirred at rt for 1.5 hours. The reaction was diluted with CH₂Cl₂ (20 mL) and the organic phase washed with sat. aq. NaHCO₃ (15 mL) and brine (15 mL), dried (MgSO₄) and concentrated under reduced pressure to give the crude product. Purification by silica gel chromatography (10% to 12.5% ethyl acetate/hexanes) gave Compound 21 (18.8 mg, 44%) as a pale yellow solid.

¹H NMR (400 MHz, CDCl₃) δ 5.72 (s, 1H), 5.30-5.21 (m, 3H), 4.29 (dd, J=11.9, 4.4 Hz, 2H), 4.13 (dd, J=11.6, 5.5 Hz, 2H), 3.53 (dd, J=8.3, 8.3 Hz, 1H), 2.48-2.22 (m, 12H), 2.08-1.98 (m, 2H), 1.92-1.80 (m, 2H), 1.75-1.50 (m, 13H), 1.49-1.20 (m, 49H), 1.18 (s, 3H), 1.17-0.83 (m, 5H), 0.87 (t, J=6.9 Hz, 6H), 0.79 (s, 3H).

Scheme 6. Synthesis of amine prodrugs with a modified acetal self-immolative linker.

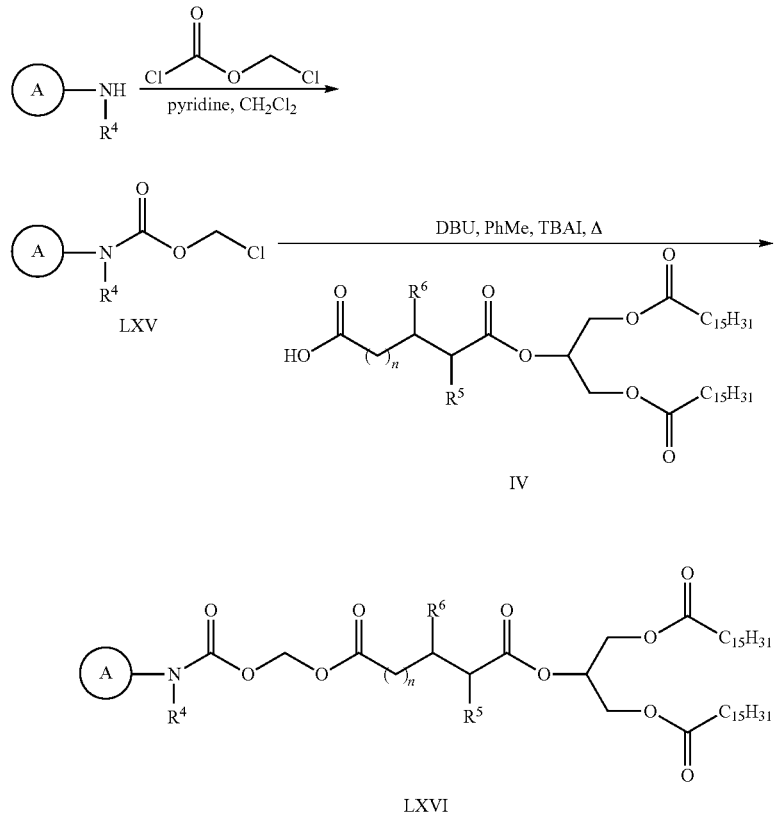

In cases where the pharmaceutical agent contains a primary or secondary amine, a modified version of the acetal self-immolative group can be used where an additional carbamate linkage is included (see Scheme 6). Reaction of the amine with chloromethyl chloroformate gives chloromethyl carbamate XXX. Displacement of the halide leaving group is then accomplished by treatment with the carboxylate derived from acid-TG IV in refluxing toluene to afford the modified ASI prodrug XXXI.

aa) Chloromethyl ((1S,4S)-4-(3,4-dichlorophenyl)-1,2,3,4-tetrahydronaphthalen-1-yl)(methyl)carbamate (XXX)

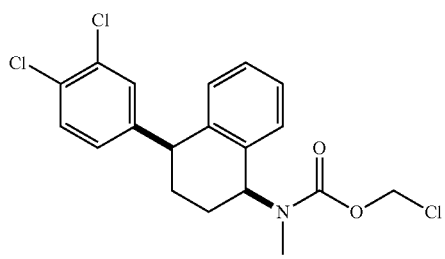

Chloromethyl chloroformate (8.3 µL, 93.3 µmol) and pyridine (14.1 µL, 175 µmol) were added to sertraline hydrochloride (20.0 mg, 58.3 µmol) in $CH_2Cl_2$ (4.5 mL) at 0° C. and the mixture stirred at 0° C. for 30 minutes and then at rt for four hours. The reaction was diluted with $CH_2Cl_2$ (20 mL) and the organic phase washed with sat. aq. $NaHCO_3$ (2×20 mL) and brine (20 mL each), dried ($MgSO_4$) and concentrated under reduced pressure to give the crude product. Purification by silica gel chromatography (10% to 15% ethyl acetate/hexanes) gave chloromethyl carbamate XXX (20.5 mg, 88%) as a colourless solid.

$^1$H NMR (400 MHz, $CDCl_3$) δ 7.34 (d, J=8.3 Hz, 1H), 7.29 (m, 1H), 7.23-7.19 (m, 2H), 7.08 (s, br, 1H), 6.97 (m, 1H), 6.81 (m, 1H), 5.93-5.83 (m, 2H), 5.51 (dd, J=10.5, 6.4 Hz, 0.6H), 5.33 (m, 0.4H), 4.20 (m, 1H), 2.77 (s, 1.2H), 2.72 (s, 1.8H), 2.29 (m, 1H), 2.02 (m, 1H), 1.79 (m, 2H). Note: Fractional integrations reflect the presence of a ~3:2 mixture of rotational isomers due to restricted rotation around the N-methylcarbamate functionality.

ab) 1-(1,3-Bis(palmitoyloxy)propan-2-yl) 5-(((((1S,4S)-4-(3,4-dichlorophenyl)-1,2,3,4-tetrahydronaphthalen-1-yl)(methyl)carbamoyl)oxy)methyl) 3-methylpentanedioate (7)

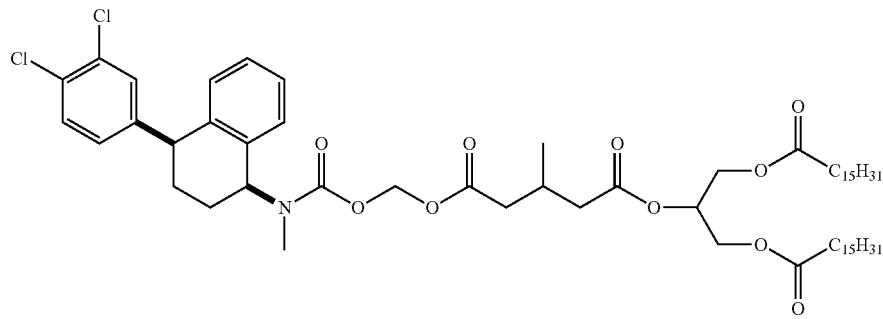

1,8-Diazabicyclo[5.4.0]undec-7-ene (DBU) (8.6 µL, 57.2 µmol) and tetra-n-butylammonium iodide (TBAI, 5.8 mg, 14.3 µmol) were added to a solution of acid-TG IV (20.5 mg, 29.4 µmol) and chloromethyl ether XXX (11.8 mg, 29.6 µmol) in toluene (1.5 mL) and the mixture heated at reflux for three hours. The reaction was cooled to rt, diluted with ethyl acetate (15 mL) and the organic phase washed with water (3×15 mL) and brine (2×15 mL), dried ($MgSO_4$) and concentrated under reduced pressure to give the crude product. Silica gel chromatography (10% to 20% ethyl acetate/hexanes) gave Compound 7 (21.1 mg, 68%) as a colourless oil.

$^1$H NMR (400 MHz, $CDCl_3$) δ 7.33 (d, J=8.3 Hz, 1H), 7.31-7.27 (m, 1H), 7.21-7.16 (m, 2H), 7.09 (d, J=2.0 Hz, 1H), 6.96 (d, J=7.2 Hz, 1H), 6.80 (td, J=8.0, 2.0 Hz, 1H), 5.89-5.82 (m, 2H), 5.49 (dd, J=10.3, 6.5 Hz, 0.6H), 5.37-5.30 (m, 0.4H), 5.27 (m, 1H), 4.33-4.25 (m, 2H), 4.19 (m, 1H), 4.15-4.10 (m, 2H), 2.74 (s, 1.2H), 2.69 (s, 1.8H), 2.54-2.39 (m, 3H), 2.36-2.23 (m, 3H), 2.30 (t, J=7.5 Hz, 4H), 2.01 (m, 1H), 1.84-1.70 (m, 2H), 1.66-1.57 (m, 4H), 1.33-1.20 (m, 48H), 1.05 (d, J=6.2 Hz, 2H), 1.02 (d, J=6.0 Hz, 1H), 0.88 (t, J=6.9 Hz, 6H). Note: Fractional integrations reflect the presence of a ~3:2 mixture of rotational isomers due to restricted rotation around the N-methylcarbamate functionality.

Example 5. Methods for Preparing Compounds of the Formula (I) Wherein Z Represents C(O)R³ and R³ Represents a Trimethyl Lock Self-Immolative Group and L Represents X' where X' is O, NR⁴ or S(O)₂NH

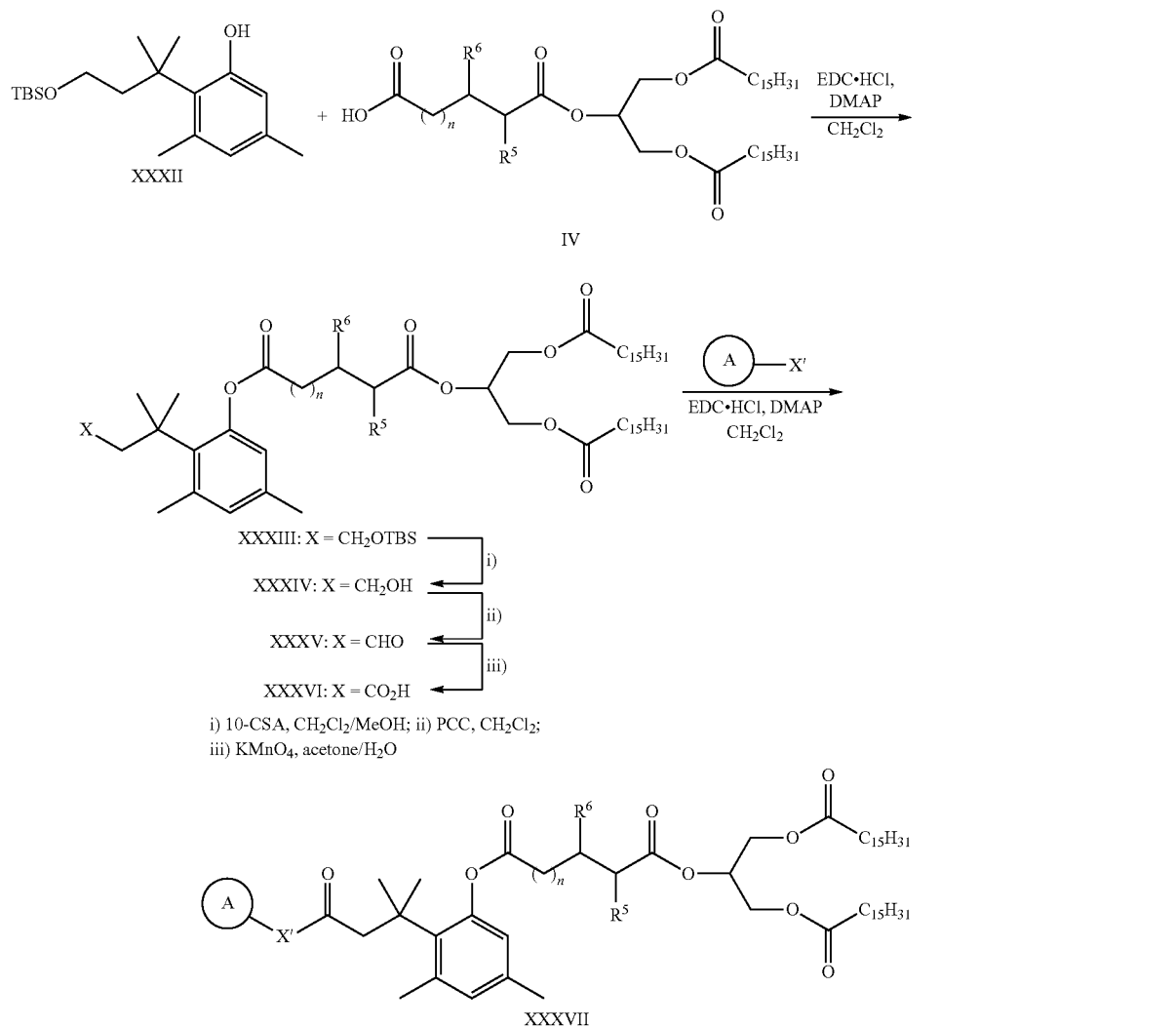

i) 10-CSA, CH₂Cl₂/MeOH; ii) PCC, CH₂Cl₂;
iii) KMnO₄, acetone/H₂O

For the synthesis of prodrugs containing a 'trimethyl lock' (TML) self-immolative linker (Levine, M. N.; Raines, R. T. *Chem. Sci.* 2012, 3, 2412-2420), again placed between the pharmaceutical agent and the alkyl spacer to facilitate systemic release of the parent molecule, the acid-triglyceride IV must be functionalised with the TML moiety prior to conjugation with a pharmaceutical agent as outlined in Scheme 7. Coupling of acid-TG IV with TML phenol XXXII under standard conditions gives triglyceride XXXIII, which can be transformed into the desired acid XXXVI in a similar way to that described in Scheme 4. Deprotection of TBS ether XXXIII can be achieved under acidic conditions (10-camphorsulfonic acid) and the resulting alcohol XXXIV oxidised in a two-step process to provide acid XXXVI. Coupling to either an alcohol, amine or sulfonamide-containing pharmaceutical agent can then be carried out under standard conditions to give the target compound XXXVII.

ac) 1,3-Bis(palmitoyloxy)propan-2-yl (2-(4-((tert-butyldimethylsilyl)oxy)-2-methylbutan-2-yl)-3,5-dimethylphenyl) adipate (XXXIII)

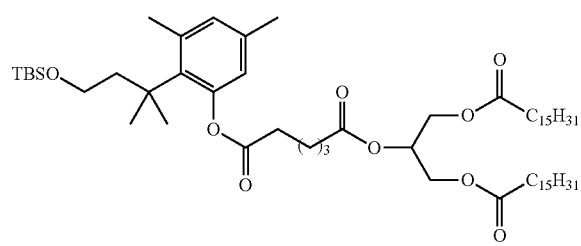

4-(Dimethylamino)pyridine (DMAP, 4.0 mg, 33.1 µmol) and EDC.HCl (12.6 mg, 66.2 mol) were added to a solution of acid-TG IV (30.0 mg, 43.0 µmol) and phenol XXXII (10.7 mg, 33.1 µmol) in CH₂Cl₂ (1 mL) and the mixture stirred at rt for 16 hours. The reaction was diluted with CH₂Cl₂ (5 mL), silica gel was added and the mixture concentrated under reduced pressure. Purification by silica gel chromatography (4% to 6% ethyl acetate/hexanes) gave TML triglyceride XXXIII (19.8 mg, 59%) as a colourless oil.

$^1$H NMR (400 MHz, CDCl₃) δ 6.80 (d, J=2.0 Hz, 1H), 6.52 (d, J=1.9 Hz, 1H), 5.27 (m, 1H), 4.31 (dd, J=11.9, 4.3 Hz, 2H), 4.15 (dd, J=11.9, 5.9 Hz, 2H), 3.47 (t, J=7.5 Hz, 1H), 2.55 (t, J=7.1 Hz, 2H), 2.51 (s, 3H), 2.39 (t, J=7.0 Hz, 2H), 2.31 (t, J=7.6 Hz, 4H), 2.22 (s, 3H), 2.02 (t, J=7.5 Hz, 1H), 1.82-1.72 (m, 4H), 1.65-1.56 (m, 4H), 1.45 (s, 6H), 1.36-1.20 (m, 48H), 0.88 (t, J=6.9 Hz, 6H), 0.84 (s, 9H), −0.03 (s, 6H).

ad) 1,3-Bis(palmitoyloxy)propan-2-yl (2-(4-hydroxy-2-methylbutan-2-yl)-3,5-dimethylphenyl) adipate (XXXIV)

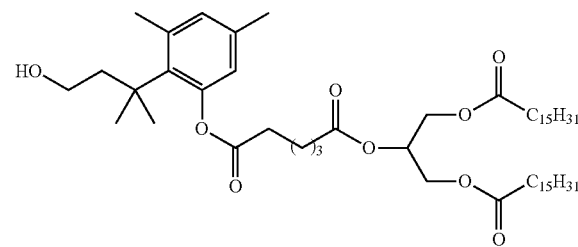

A solution of 10-camphorsulfonic acid (0.122 M in MeOH, 10 µL, 1.2 µmol) was added to TBS ether XXXIII (6.1 mg, 6.1 µmol) in CH₂Cl₂ (0.4 mL) and MeOH (0.4 mL) and the mixture stirred at rt for one hour. The reaction was diluted with water (5 mL) and the aqueous layer extracted with ethyl acetate (3×10 mL). The combined organic extracts were washed with sat. aq. NaHCO₃ and brine (20 mL each), dried (MgSO₄) and concentrated under reduced pressure to give crude alcohol XXXIV (6.1 mg, quant.) as a colourless oil that was used without purification.

$^1$H NMR (400 MHz, CDCl₃) δ 6.82 (d, J=1.4 Hz, 1H), 6.53 (d, J=1.2 Hz, 1H), 5.27 (m, 2H), 4.31 (dd, J=11.9, 4.3 Hz, 2H), 4.15 (dd, J=11.9, 5.8 Hz, 2H), 3.53 (t, J=7.2 Hz, 2H), 2.58 (t, J=7.0 Hz, 2H), 2.52 (s, 3H), 2.40 (t, J=6.9 Hz, 2H), 2.31 (t, J=7.6 Hz, 4H), 2.23 (s, 3H), 2.04 (t, J=7.2 Hz, 2H), 1.82-1.72 (m, 4H), 1.65-1.53 (m, 4H), 1.48 (s, 6H), 1.36-1.13 (m, 48H), 0.88 (t, J=6.7 Hz, 6H).

ae) 1,3-Bis(palmitoyloxy)propan-2-yl (3,5-dimethyl-2-(2-methyl-4-oxobutan-2-yl)phenyl) adipate (XXXV)

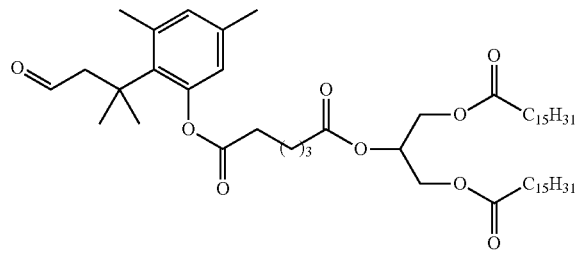

Pyridinium chlorochromate (PCC, 2.6 mg, 12.2 µmol) was added to a suspension of alcohol XXXIV (5.4 mg, 6.1 µmol) and Celite (5 mg) in CH₂Cl₂ (0.5 mL) at 0° C. and the mixture stirred at rt for one hour. The reaction was filtered through a short pad of silica gel, eluting with 50% ethyl acetate/hexanes, and the filtrate concentrated under reduced pressure to give crude aldehyde XXXV (5.4 mg, quant.) as a yellow oil that was used without purification.

$^1$H NMR (400 MHz, CDCl₃) δ 9.53 (t, J=2.6 Hz, 1H), 6.84 (d, J=1.4 Hz, 1H), 6.57 (d, J=1.8 Hz, 1H), 5.27 (m, 1H), 4.31 (dd, J=11.9, 4.3 Hz, 2H), 4.15 (dd, J=11.9, 5.9 Hz, 2H), 2.80 (d, J=2.6 Hz, 2H), 2.57 (t, J=7.1 Hz, 2H), 2.53 (s, 3H), 2.40 (t, J=7.0 Hz, 2H), 2.31 (t, J=7.6 Hz, 5H), 2.24 (s, 3H), 1.83-1.72 (m, 4H), 1.65-1.56 (m, 4H), 1.55 (s, 6H), 1.35-1.16 (m, 48H), 0.88 (t, J=6.7 Hz, 6H).

af) 3-(2-((6-((1,3-Bis(palmitoyloxy)propan-2-yl)oxy)-6-oxohexanoyl)oxy)-4,6-dimethylphenyl)-3-methylbutanoic acid (XXXVI)

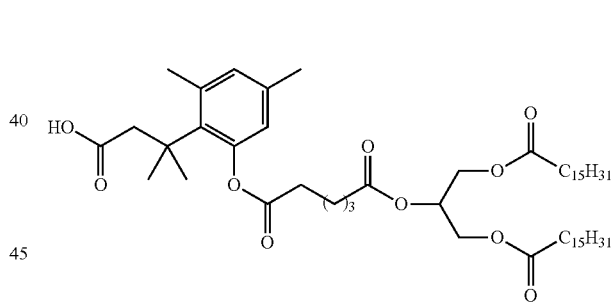

A solution of potassium permanganate (0.0775 M in 1:1 acetone/water, 200 µL, 15.5 µmol) was added to aldehyde XXXV (12.5 mg, 0.0340 µmol) in acetone (0.5 mL) and water (0.1 mL) and the mixture stirred at rt for 18 hours. The reaction was diluted with water (10 mL), acidified to pH 2 using 1 M HCl, and the aqueous layer extracted with ethyl acetate (3×15 mL). The combined organic extracts were washed with brine (30 mL), dried (MgSO₄) and concentrated under reduced pressure to give the crude product. Purification by silica gel chromatography (10% to 20% ethyl acetate/hexanes) gave acid XXXVI (9.5 mg, 75%) as a colourless solid.

$^1$H NMR (400 MHz, CDCl₃) δ 6.82 (d, J=1.3 Hz, 1H), 6.56 (d, J=1.7 Hz, 1H), 5.26 (m, 1H), 4.32 (dd, J=11.9, 4.4 Hz, 2H), 4.15 (dd, J=11.9, 5.8 Hz, 2H), 2.82 (s, 2H), 2.60 (t, J=7.0 Hz, 2H), 2.55 (s, 3H), 2.40 (t, J=6.9 Hz, 2H), 2.31 (t, J=7.6 Hz, 4H), 2.22 (s, 3H), 1.84-1.72 (m, 4H), 1.66-1.49 (m, 4H), 1.58 (s, 6H), 1.36-1.19 (m, 48H), 0.88 (t, J=6.8 Hz, 6H).

ag) 1,3-Bis(palmitoyloxy)propan-2-yl (2-(4-(((8R,9S,10R,13S,14S,17S)-10,13-dimethyl-3-oxo-2,3,6,7,8,9,10,11,12,13-14,15,16,17-tetradecahydro-1H-cyclopenta[a]phenanthren-17-yl)oxy)-2-methyl-4-oxobutan-2-yl)-3,5-dimethylphenyl) adipate (22)

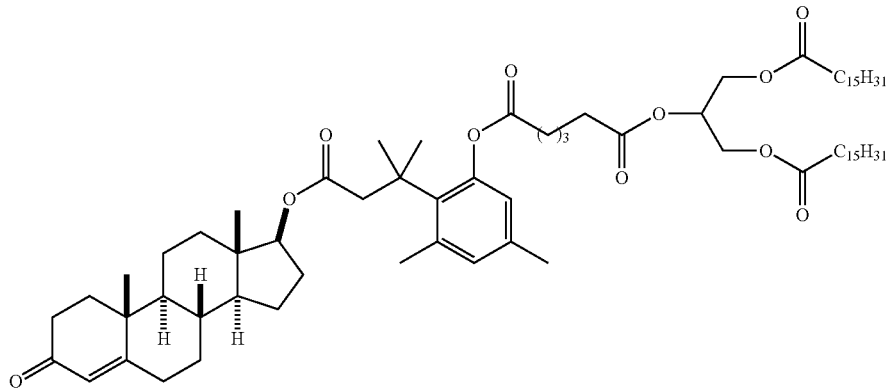

4-(Dimethylamino)pyridine (DMAP, 1.8 mg, 14.4 µmol), EDC.HCl (6.9 mg, 36.1 µmol) and testosterone (7.5 mg, 26.0 µmol) were added to a solution of acid XXXVI (13.0 mg, 14.4 µmol) in $CH_2Cl_2$ (1 mL) and the mixture stirred at rt for 26 hours. The reaction was diluted with $CH_2Cl_2$ (5 mL), silica gel was added and the mixture concentrated under reduced pressure. Purification by silica gel chromatography (15% to 20% ethyl acetate/hexanes) gave Compound 22 (8.6 mg, 51%) as a colourless solid.

$^1$H NMR (400 MHz, $CDCl_3$) δ 6.80 (d, J=1.8 Hz, 1H), 6.55 (d, J=1.7 Hz, 1H), 5.72 (s, 1H), 5.27 (m, 1H), 4.45 (dd, J=9.1, 7.3 Hz, 1H), 4.31 (dd, J=11.9, 4.4 Hz, 2H), 4.15 (dd, J=11.9, 5.8 Hz, 2H), 2.80 (ABq, 2H), 2.58 (t, J=7.0 Hz, 2H), 2.54 (s, 3H), 2.48-2.23 (m, 10H), 2.21 (s, 3H), 2.11-1.97 (m, 2H), 1.86-1.47 (m, 16H), 1.55 (s, 6H), 1.43-1.19 (m, 49H), 1.17 (s, 3H), 1.12-0.82 (m, 4H), 0.88 (t, J=6.9 Hz, 6H), 0.65 (s, 3H).

ah) 1,3-Bis(palmitoyloxy)propan-2-yl (2-(4-(((1S,4S)-4-(3,4-dichlorophenyl)-1,2,3,4-tetrahydro-naphthalen-1-yl)(methyl)amino)-2-methyl-4-oxobutan-2-yl)-3,5-dimethylphenyl) adipate (1)

4-(Dimethylamino)pyridine (DMAP, 0.9 mg, 7.8 µmol), EDC.HCl (4.4 mg, 23.3 µmol), $Et_3N$ (5.0 µL, 66.6 µmol) and sertraline hydrochoride (5.3 mg, 15.5 µmol) were added to a solution of acid XXXVI (7.0 mg, 7.8 µmol) in $CH_2Cl_2$ (0.5 mL) and the mixture stirred at rt for 16 hours. The reaction was diluted with $CH_2Cl_2$ (3 mL), silica gel was added and the mixture concentrated under reduced pressure. Purification by silica gel chromatography (10% to 20% ethyl acetate/hexanes) gave Compound 1 (5.6 mg, 61%) as a colourless solid.

$^1$H NMR (400 MHz, $CDCl_3$) δ 7.32 (d, J=8.3 Hz, 0.7H), 7.31 (d, J=8.3 Hz, 0.3H), 7.25-7.11 (m, 2H), 7.09-7.02 (m, 1.3H), 6.97-6.90 (m, 1H), 6.87-6.78 (m, 2.4H), 6.72 (dd, J=8.3, 2.0 Hz, 0.3H), 6.58 (d, J=1.5 Hz, 0.7H), 6.55 (d, J=1.5 Hz, 0.3H), 5.88 (dd, J=10.7, 6.3 Hz, 0.7H), 5.25 (m, 1H), 4.94 (dd, J=10.8, 5.7 Hz, 0.3H), 4.30 (dd, J=11.9, 4.4 Hz, 2H), 4.20-4.14 (m, 1H), 4.14 (dd, J=11.9, 4.4 Hz, 2H), 3.07 (d, J=15.4 Hz, 0.7H), 3.00 (d, J=4.9 Hz, 0.6H), 2.82 (d, J=15.4 Hz, 0.7H), 2.64 (s, 2.1H), 2.62-2.53 (m, 5.3H), 2.48 (t, J=7.1 Hz, 0.6H), 2.39 (t, J=7.1 Hz, 1.4H), 2.31 (t, J=7.6 Hz, 4.6H), 2.23 (s, 2.1H), 2.21 (s, 0.9H), 1.99-1.91 (m, 1H), 1.85-1.72 (m, 4H), 1.71-1.53 (m, 13H), 1.36-1.19 (m, 48H), 0.88 (t, J=6.9 Hz, 6H). Note: Fractional integrations reflect the presence of a 7:3 mixture of rotational isomers due to restricted rotation around the N-methylamide functionality.

Characterisation data for further exemplary trimethyl lock containing compounds of the formula (I) are provided below in Table 5.

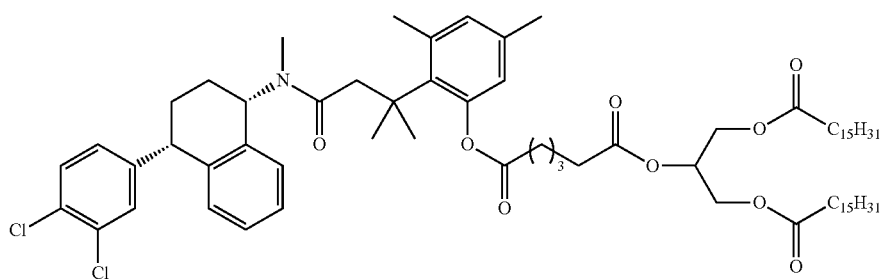

TABLE 5

¹H NMR data for representative compounds

| Compound No. | ¹H NMR (400 MHz, CDCl₃) |
|---|---|
| 5 | δ 8.74 (s, 1H), 7.79-7.73 (m, 2H), 7.43-7.36 (m, 3H), 7.17 (d, J = 8.0 Hz, 2H), 7.11 (d, J = 8.2 Hz, 2H), 6.74 (s, 1H), 6.66 (d, J = 1.4 Hz, 1H), 6.54 (d, J = 1.5 Hz, 1H), 5.26 (m, 1H), 4.30 (dd, J = 11.9, 4.4 Hz, 2H), 4.15 (dd, J = 11.9, 5.6 Hz, 2H), 2.62 (t, J = 7.6 Hz, 2H), 2.38 (s, 3H), 2.35-2.29 (m, 8H), 2.25 (s, 3H), 2.07 (s, 3H), 1.85-1.74 (m, 2H), 1.68-1.58 (m, 6H), 1.56 (s, 6H), 1.46-1.20 (m, 56H), 0.88 (t, J = 6.8 Hz, 6H). |
| 25 | δ 6.80 (d, J = 1.5 Hz, 1H), 6.55 (d, J = 1.4 Hz, 1H), 5.72 (s, 1H), 5.29 (m, 1H), 4.45 (m, 1H), 4.31 (ddd, J = 11.9, 4.2, 2.9 Hz, 2H), 4.15 (dd, J = 11.9, 5.9 Hz, 2H), 2.80 (qd, J = 14.5, 1.9 Hz, 2H), 2.66 (dd, J = 15.3, 5.4 Hz, 1H), 2.54 (s, 3H), 2.62-2.44 (m, 3H), 2.43-2.24 (m, 9H), 2.22 (s, 3H), 2.11-1.98 (m, 2H), 1.88 (m, 1H), 1.70 (dd, J = 13.8, 5.2 Hz, 1H), 1.66-1.47 (m, 8H), 1.42-1.20 (m, 51H), 1.17 (s, 3H), 1.13 (d, J = 6.3 Hz, 3H), 1.10-0.84 (m, 4H), 0.88 (t, J = 6.8 Hz, 6H), 0.65 (s, 3H). |
| 26 | δ 6.79 (d, J = 1.9 Hz, 1H), 6.54 (d, J = 1.8 Hz, 1H), 5.71 (s, 1H), 5.26 (m, 1H), 4.45 (dd, J = 9.1, 7.3 Hz, 1H), 4.29 (dd, J = 11.9, 4.4 Hz, 2H), 4.14 (dd, J = 11.9, 5.9 Hz, 2H), 2.80 (ABq, 2H), 2.54 (t, J = 7.5 Hz, 2H), 2.53 (s, 3H), 2.47-2.23 (m, 11H), 2.21 (s, 3H), 2.11-1.97 (m, 2H), 1.85-1.46 (m, 13H), 1.55 (s, 6H), 1.44-1.18 (m, 59H), 1.17 (s, 3H), 1.11-0.92 (m, 4H), 0.87 (t, J = 6.5 Hz, 6H), 0.65 (s, 3H). |
| 27 | δ 6.79 (d, J = 1.9 Hz, 1H), 6.55 (d, J = 1.7 Hz, 1H), 5.71 (s, 1H), 5.27 (m, 1H), 4.45 (dd, J = 9.1, 7.3 Hz, 1H), 4.29 (dd, J = 12.0, 4.0 Hz, 2H), 4.14 (dd, J = 11.9, 6.0 Hz, 2H), 2.80 (ABq, 2H), 2.54 (t, J = 7.5 Hz, 2H), 2.53 (s, 3H), 2.45-2.23 (m, 9H), 2.21 (s, 3H), 2.18-1.90 (m, 4H), 1.87-1.66 (m, 4H), 1.66-1.48 (m, 8H), 1.55 (s, 6H), 1.45-1.19 (m, 59H), 1.17 (s, 3H), 1.11-0.91 (m, 4H), 0.93 (d, J = 6.6 Hz, 3H), 0.87 (t, J = 6.8 Hz, 6H), 0.65 (s, 3H). |

Example 6. Methods for Preparing Compounds of the Formula (I) Wherein Y Represents an Unsubstituted or Short-Chain (n=2, 3) α- or β-Methyl Substituted Alkyl Group and L Represents X'C(O) where X' is O ai) 2-((4-Bromobutanoyl)oxy)propane-1,3-diyl dipalmitate (XXIII)

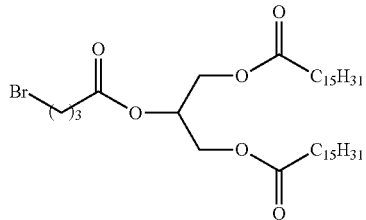

4-(Dimethylamino)pyridine (DMAP, 64.4 mg, 0.527 mmol) and N,N'-dicyclohexylcarbodiimide (DCC, 218 mg, 1.05 mmol) were added sequentially to a solution of 4-bromobutyric acid (XXII) (141 mg, 0.844 mmol) and III (300 mg, 0.527 mmol) in CH₂Cl₂ (12 mL) and the mixture stirred at rt for 19 hours. The resulting suspension was diluted with CH₂Cl₂ (15 mL), cooled to 0° C. and filtered through Celite, washing with further CH₂Cl₂ (20 mL). The organic phase was washed with 1 M HCl, water, sat. aq. NaHCO₃ and brine (30 mL each), dried (MgSO₄) and concentrated under reduced pressure to give the crude product. Silica gel chromatography (5% ethyl acetate/hexanes) gave bromotriglyceride XXIII (352 mg, 93%) as a colourless solid.

¹H NMR (400 MHz, CDCl₃) δ 5.27 (m, 1H), 4.32 (dd, J=12.0, 4.2 Hz, 2H), 4.14 (dd, J=12.0, 6.0 Hz, 2H), 3.46 (t, J=6.5 Hz, 2H), 2.53 (t, J=7.1 Hz, 2H), 2.32 (t, J=7.6 Hz, 4H), 2.20-2.15 (m, 2H), 1.65-1.58 (m, 4H), 1.36-1.21 (m, 48H), 0.88 (t, J=6.9 Hz, 3H).

In some cases where the ω-halocarboxylic acid XXII is not commercially available, synthesis can be achieved by accessing the corresponding lactones followed by ring-opening, as described below.

aj) Oxacyclohexadecan-2-one (XXXVIII)

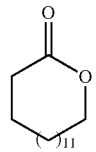

m-Chloroperoxybenzoic acid (m-CPBA, 70% pure, 687 mg, 2.79 mmol) was added to a solution of cyclopentadecanone (500 mg, 2.23 mmol) in CH₂Cl₂ (6 mL) at 0° C. and the reaction stirred at rt for four days and 22 hours. 1H NMR analysis of a reaction aliquot taken after three days indicated 74% consumption of ketone and at this point an extra portion of m-CPBA (150 mg) was added. After four days and 22 hours, the reaction was diluted with CH₂Cl₂ (20 mL), washed with sat. aq. NaHCO₃, (3×20 mL), water (20 mL) and brine (20 mL) and concentrated under reduced pressure to give the crude product. Silica gel chromatography (5% to 10% ethyl acetate/hexanes) gave lactone XXXVIII (463 mg, 86%) as a colourless oil.

¹H NMR (400 MHz, CDCl₃) δ 4.15-4.11 (m, 2H), 2.35-2.29 (m, 2H), 1.71-1.58 (m, 4H), 1.45-1.27 (m, 20H).

ak) 15-Iodopentadecanoic acid (XXII)

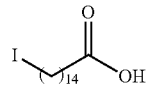

Chlorotrimethylsilane (TMSCl, 242 μL, 1.91 mmol) was added to a suspension of XXXVIII (153 mg, 0.636 mmol) and sodium iodide (286 mg, 1.91 mmol) in acetonitrile (1.5 mL) and the mixture heated at reflux for 21 hours. The reaction was cooled to rt, diluted with water (10 mL) and 10% aq. $Na_2S_2O_3$ (10 mL) and extracted with ethyl acetate (3×20 mL). The combined organic extracts were washed with brine (40 mL), dried ($MgSO_4$) and concentrated under reduced pressure to give the crude product. Silica gel chromatography (50% ethyl acetate/hexanes) gave iodoacid XXII (87.4 mg, 37%, 70% pure) as a yellow oil. It was observed that several impurity signals in the 1H NMR spectrum increased in intensity after chromatography, and it was suspected that one of the two minor components was the hydroxy acid formed by hydrolysis of the iodide functional group (δ 3.53 for hydroxy, δ 3.18 for iodo).

$^1$H NMR (400 MHz, $CDCl_3$) δ 3.18 (t, J=7.1 Hz, 2H), 2.34 (t, J=7.5 Hz, 2H), 1.86-1.78 (m, 2H), 1.68-1.57 (m, 2H), 1.42-1.22 (m, 20H).

al) 3-Methyltetrahydro-2H-pyran-2-one (XXXIX)

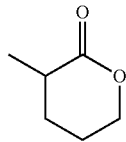

A solution of n-butyllithium (1.0 M in hexanes, 5.49 mL, 5.49 mmol) was added dropwise to diisopropylamine (910 μL, 6.49 mmol) in THF (4 mL) at 0° C. and the mixture stirred at 0° C. for 30 minutes to give a pale yellow solution of LDA, which was then cooled to −40° C. A cold (−40° C.) solution of 6-valerolactone (500 mg, 4.99 mmol) in THF (4 mL) was added dropwise via cannula and the resultant mixture stirred at −40° C. for 10 minutes before being cooled to −78° C. Iodomethane (466 μL, 7.49 mmol) was then added dropwise and the mixture slowly warmed to 0° C. over four hours. The reaction was quenched by the slow addition of acetic acid (320 μL), diluted with ethyl acetate (10 mL) and water (15 mL) and the aqueous phase extracted with ethyl acetate (3×15 mL). The combined organic extracts were washed with sat. aq. $NaHCO_3$ and brine (30 mL each), dried ($MgSO_4$) and concentrated under reduced pressure to give the crude product. Silica gel chromatography (15% to 17.5% ethyl acetate/hexanes with 1% $Et_3N$) gave α-methyl-δ-valerolactone XXXIX (144 mg, 25%) as a colourless oil.

$^1$H NMR (400 MHz, $CDCl_3$) δ 4.37-4.26 (m, 2H), 2.58 (ddt, J=11.1, 7.0, 7.0 Hz, 1H), 2.09 (tt, J=12.4, 6.2 Hz, 1H), 1.98-1.83 (m, 2H), 1.54 (ddt, J=13.4, 11.1, 7.4 Hz, 1H), 1.26 (d, J=6.9 Hz, 3H).

am) 4-Methyltetrahydro-2H-pyran-2-one (XL)

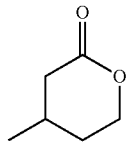

Methyllithium (1.0 M in $Et_2O$, 2.00 mL, 2.00 mmol) was added to a suspension of CuI (190 mg, 1.00 mmol) in $Et_2O$ (2 mL) at 0° C. and the pale yellow reaction mixture immediately cooled to −40° C. A solution of 5,6-dihydro-2H-pyran-2-one (43.1 μL, 0.50 mmol) in $Et_2O$ (2 mL) was added dropwise via cannula and the reaction stirred at −40° C. for 10 minutes, then at 0° C. for 10 minutes and at rt for 30 minutes. The resulting yellow suspension was transferred by syringe to a vigorously stirred mixture of sat. aq. $NH_4Cl$ (5 mL) and ethyl acetate (5 mL) at −40° C. and the quenched reaction allowed to slowly warm to rt over 30 minutes. The reaction was diluted with water (5 mL), extracted with ethyl acetate (3×15 mL) and the combined organic extracts washed with 1 M $Na_2S_2O_3$ and brine (30 mL each), dried ($MgSO_4$) and concentrated under reduced pressure to give crude β-methyl-δ-valerolactone XL (22.7 mg, 40%) as a yellow oil that was used without purification.

$^1$H NMR (400 MHz, $CDCl_3$) δ 4.42 (ddd, J=11.4, 4.9, 4.0 Hz, 1H), 4.27 (ddd, J=11.4, 10.6, 3.8 Hz, 1H), 2.68 (m, 1H), 2.17-2.06 (m, 2H), 1.92 (dqd, J=13.8, 3.9, 1.5 Hz, 1H), 1.52 (m, 1H), 1.

an) (E)-Allyl 6-(4-(allyloxy)-6-methoxy-7-methyl-3-oxo-1,3-dihydroisobenzofuran-5-yl)-4-methyl-hex-4-enoate (XLI)

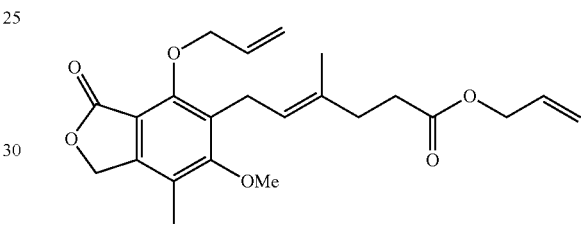

1,8-Diazabicyclo[5.4.0]undec-7-ene (DBU) (602 μL, 4.03 mmol) and allyl bromide (238 μL, 2.82 mmol) were added to a solution of mycophenolic acid (250 mg, 0.809 mmol) in DMF (15 mL) and the mixture stirred at rt for 18 hours. The reaction was diluted with ethyl acetate (20 mL) and water (20 mL) and the aqueous phase extracted with ethyl acetate (2×30 mL). The combined organic extracts were washed with water and brine (40 mL each), dried ($MgSO_4$) and concentrated under reduced pressure to give the crude product. Silica gel chromatography (30% ethyl acetate/hexanes) gave the allyl ester XLI (292 mg, 93%) as a colourless oil.

$^1$H NMR (400 MHz, $CDCl_3$) δ 6.09 (ddt, J=17.1, 10.4, 5.9 Hz, 1H), 5.86 (ddt, J=17.2, 10.4, 5.7 Hz, 1H), 5.37 (dq, J=17.2, 1.5 Hz, 1H), 5.30-5.15 (m, 4H), 5.13 (s, 2H), 4.78 (dt, J=5.9, 1.3 Hz, 2H), 4.52 (dt, J=5.7, 1.4 Hz, 2H), 3.76 (s, 3H), 3.41 (d, J=6.5 Hz, 2H), 2.44-2.39 (m, 2H), 2.35-2.27 (m, 2H), 2.17 (s, 3H), 1.79 (s, 3H).

ao) (E)-6-(4-(Allyloxy)-6-methoxy-7-methyl-3-oxo-1,3-dihydroisobenzofuran-5-yl)-4-methylhex-4-enoic acid (XLII)

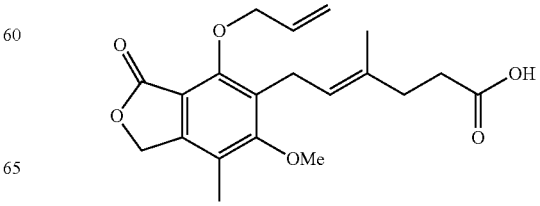

A mixture of ester XLI (44.0 mg, 0.110 mmol) in 2 M NaOH (330 μL, 0.660 mmol), water (1 mL) and MeOH (1.3 mL) was stirred at rt for 1.5 hours. The reaction was acidified to pH 1 with 1 M HCl, diluted with water (5 mL) and then extracted with ethyl acetate (3×15 mL). The combined organic extracts were washed with brine (30 mL), dried (MgSO$_4$) and concentrated under reduced pressure to give the crude product. Silica gel chromatography (40% to 60% ethyl acetate/hexanes) gave the acid XLII (32.7 mg, 83%) as a colourless oil.

$^1$H NMR (400 MHz, CDCl$_3$) δ 6.09 (m, 1H), 5.36 (ddd, J=17.2, 3.1, 1.5 Hz, 1H), 5.25-5.16 (m, 2H), 5.13 (s, 2H), 4.77 (dt, J=5.9, 1.3 Hz, 2H), 3.76 (s, 3H), 3.42 (d, J=6.7 Hz, 2H), 2.45-2.39 (m, 2H), 2.35-2.25 (m, 2H), 2.17 (s, 3H), 1.79 (s, 3H).

ap) E)-2-((4-((6-(4-(Allyloxy)-6-methoxy-7-methyl-3-oxo-1,3-dihydroisobenzofuran-5-yl)-4-methylhex-4-enoyl)oxy)butanoyl)oxy)propane-1,3-diyl dipalmitate (XLIII)

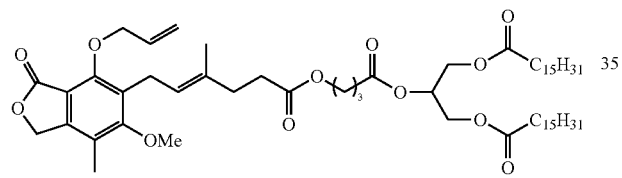

1,8-Diazabicyclo[5.4.0]undec-7-ene (DBU) (18.5 μL, 124 μmol) was added to a suspension of XLII (30.6 mg, 85.0 μmol) and bromide XXIII (55.5 mg, 77.3 μmol) in toluene (2 mL) and the mixture heated at reflux for 3.5 hours. The reaction was cooled to rt, acidified by the addition of 1 M HCl (3-4 drops) and diluted with water (10 mL). The aqueous phase was extracted with ethyl acetate (3×15 mL) and the combined organic extracts washed with water and brine (30 mL each), dried (MgSO$_4$) and concentrated under reduced pressure to give the crude product. Silica gel chromatography (15% to 20% ethyl acetate/hexanes) gave MPA triglyceride XLIII (56.2 mg, 73%) as a colourless oil.

$^1$H NMR (400 MHz, CDCl$_3$) δ 6.10 (ddt, J=17.2, 10.4, 5.9 Hz, 1H), 5.37 (dq, J=17.2, 1.5 Hz, 1H), 5.29-5.15 (m, 3H), 5.13 (s, 2H), 4.78 (dt, J=5.9, 1.3 Hz, 2H), 4.30 (dd, J=11.9, 4.4 Hz, 2H), 4.14 (dd, J=11.9, 5.8 Hz, 2H), 4.06 (t, J=6.4 Hz, 2H), 3.77 (s, 3H), 3.42 (d, J=6.8 Hz, 2H), 2.41-2.35 (m, 4H), 2.34-2.25 (m, 6H), 2.18 (s, 3H), 1.97-1.88 (m, 2H), 1.79 (s, 3H), 1.65-1.52 (m, 4H), 1.35-1.19 (m, 48H), 0.88 (t, J=6.9 Hz, 6H).

aq) (E)-2-((4-((6-(4-Hydroxy-6-methoxy-7-methyl-3-oxo-1,3-dihydroisobenzofuran-5-yl)-4-methylhex-4-enoyl)oxy)butanoyl)oxy)propane-1,3-diyl dipalmitate (30)

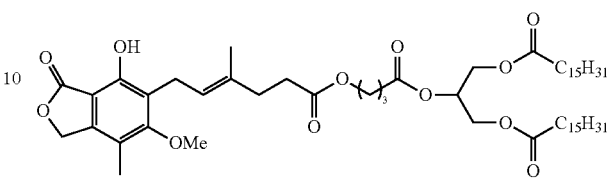

1,3-Dimethylbarbituric acid (12.4 mg, 79.2 μmol) and Pd(PPh$_3$)$_4$ (9.2 mg, 7.92 μmol) were added to allyl ether XLIII (39.5 mg, 39.6 μmol) in CH$_2$Cl$_2$ (3 mL) and the mixture stirred at 30° C. for two hours. The reaction mixture was directly applied to a short pad of silica gel, eluted with ethyl acetate (40 mL) and the filtrate concentrated under reduced pressure to give the crude product. Silica gel chromatography (15% to 20% ethyl acetate/hexanes) gave Compound 30 (36.2 mg, 96%) as a colourless solid.

$^1$H NMR (400 MHz, CDCl$_3$) δ 7.68 (s, 1H), 5.30-5.21 (m, 2H), 5.20 (s, 2H), 4.30 (dd, J=11.9, 4.4 Hz, 2H), 4.14 (dd, J=11.9, 5.8 Hz, 2H), 4.06 (t, J=6.4 Hz, 2H), 3.76 (s, 3H), 3.38 (d, J=7.0 Hz, 2H), 2.43-2.35 (m, 4H), 2.34-2.27 (m, 6H), 2.15 (s, 3H), 1.97-1.89 (m, 2H), 1.80 (s, 3H), 1.65-1.52 (m, 4H), 1.34-1.21 (m, 48H), 0.87 (t, J=6.9 Hz, 3H).

ar) 2-((5-((2-Acetoxybenzoyl)oxy)pentanoyl)oxy)propane-1,3-diyl dipalmitate (8)

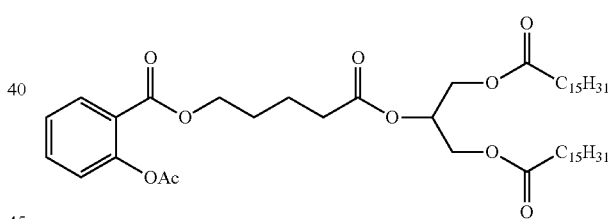

1,8-Diazabicyclo[5.4.0]undec-7-ene (DBU) (14.7 mL, 98.4 mmol) was added to a suspension of acetylsalicylic acid (aspirin, 14.8 mg, 81.9 mmol) and bromide XXIII (40.0 mg, 54.7 mmol) in toluene (2 mL) and the mixture heated at reflux for 3.5 hours. The reaction was cooled to rt, then diluted with ethyl acetate (5 mL) and water (15 mL). The aqueous layer was separated and acidified to pH 2 with 1 M HCl, and then extracted with ethyl acetate (3×20 mL). The combined organic extracts were washed with water and brine (40 mL each), dried (MgSO$_4$) and concentrated under reduced pressure to give the crude product. Silica gel chromatography (10% ethyl acetate/hexanes) gave Compound 8 (23.9 mg, 53%) as a colourless solid.

$^1$H NMR (400 MHz, CDCl$_3$) δ 8.01 (dd, J=7.9, 1.6 Hz, 1H), 7.56 (ddd, J=8.1, 7.5, 1.7 Hz, 1H), 7.31 (td, J=7.7, 1.2 Hz, 1H), 7.10 (dd, J=8.1, 1.0 Hz, 1H), 5.26 (m, 1H), 4.31 (dd, J=11.9, 4.3 Hz, 2H), 4.28 (t, J=6.9 Hz, 2H), 4.14 (dd, J=11.9, 5.9 Hz, 2H), 2.40 (t, J=6.9 Hz, 2H), 2.35 (s, 3H), 2.30 (t, J=7.6 Hz, 4H), 1.83-1.74 (m, 4H), 1.64-1.54 (m, 4H), 1.35-1.19 (m, 48H), 0.88 (t, J=6.9 Hz, 6H).

as) Synthesis of 2-((6-(((3R,5R)-7-(2-(4-Fluorophenyl)-5-isopropyl-3-phenyl-4-(phenylcarbamoyl)-1H-pyrrol-1-yl)-3,5-dihydroxyheptanoyl)oxy)hexanoyl)oxy)propane-1,3-diyl dipalmitate (9)

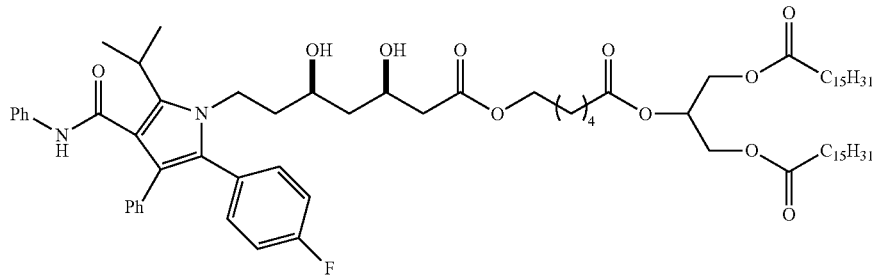

In the case of atorvastatin (ATV), the diol functionality needs to be masked as an acetonide (isopropylidene acetal) to prevent its interference in the subsequent reaction. Treatment of ATV acetonide XLIV with DBU and ω-bromo-TG XXIII in refluxing toluene as previously described gives the protected prodrug XLV. Unveiling of the diol under acidic conditions then provides Compound 9.

as(i) 2-((4R,6R)-6-(2-(2-(4-Fluorophenyl)-5-isopropyl-3-phenyl-4-(phenylcarbamoyl)-1H-pyrrol-1-yl)ethyl)-2,2-dimethyl-1,3-dioxan-4-yl)acetic acid (XLIV)

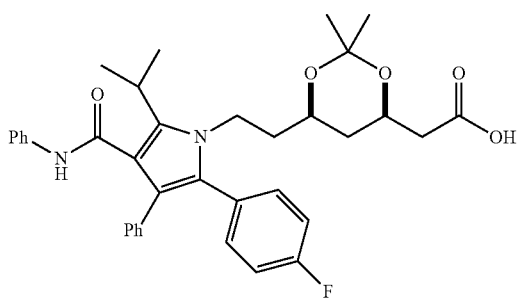 [SMILES: CC(C)c1c(C(=O)Nc2ccccc2)c(-c2ccccc2)c(-c2ccc(F)cc2)n1CC[C@@H]1C[C@H](CC(=O)O)OC(C)(C)O1]

p-Toluenesulfonic acid (p-TsOH, 10.1 mg, 0.053 mmol) was added to atorvastatin (160 mg, 0.265 mmol) in 2,2-dimethoxypropane (1.5 mL) and acetone (1.5 mL) and the mixture stirred at rt for 15 hours. The reaction was diluted with ethyl acetate (30 mL) and the organic phase washed with water (25 mL) and brine (2×25 mL), dried (MgSO$_4$) and concentrated under reduced pressure to give the crude product. Purification by silica gel chromatography (20% to 30% to 50% ethyl acetate/hexanes) gave the acetonide-acid XLIV (72.2 mg, 46%) as a colourless foam.

$^1$H NMR (400 MHz, CDCl$_3$) δ 7.22-7.13 (m, 9H), 7.07 (d, J=7.7 Hz, 2H), 7.03-6.97 (m, 3H), 6.86 (br s, 1H), 4.20 (m, 1H), 4.09 (m, 1H), 3.85 (m, 1H), 3.71 (m, 1H), 3.57 (m, 1H), 2.54 (dd, J=15.8, 6.8 Hz, 1H), 2.43 (dd, J=15.8, 5.6 Hz, 1H), 1.71-1.61 (m, 2H), 1.53 (d, J=7.1 Hz, 6H), 1.38 (s, 3H), 1.36 (m, 1H), 1.34 (s, 3H), 1.09 (m, 1H).

as(ii) 2-((6-(2-((4R,6R)-6-(2-(2-(4-Fluorophenyl)-5-isopropyl-3-phenyl-4-(phenylcarbam-oyl)-1H-pyrrol-1-yl)ethyl)-2,2-dimethyl-1,3-dioxan-4-yl)acetoxy)hexanoyl)oxy)-propane-1,3-diyl dipalmitate (XLV)

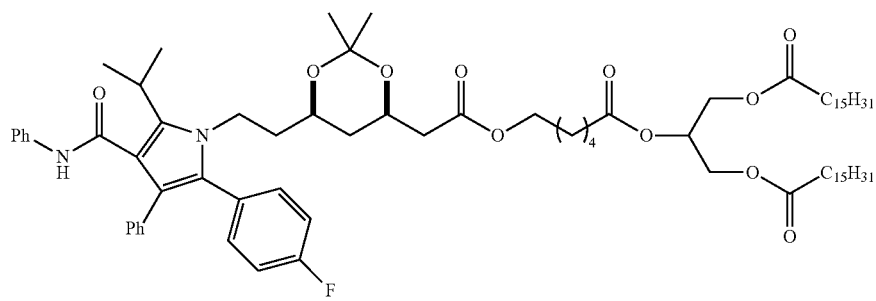

1,8-Diazabicyclo[5.4.0]undec-7-ene (DBU) (4.3 μL, 29.0 μmol) was added to a solution of the acetonide-acid XLIV (11.6 mg, 19.3 μmol) and ω-bromo-TG XXIII (12.0 mg, 16.1 μmol) in toluene (1.5 mL) and the mixture heated at reflux for 2.5 hours. The reaction was cooled to rt, diluted with ethyl acetate (30 mL) and the organic phase washed with water (25 mL), sat. aq. NaHCO$_3$ (25 mL) and brine (25 mL), dried (MgSO$_4$) and concentrated under reduced pressure to give the crude product. Silica gel chromatography (20% ethyl acetate/hexanes) gave the ATV-triglyceride XLV (13.0 mg, 64%) as a colourless oil.

$^1$H NMR (400 MHz, CDCl$_3$) δ 7.23-7.12 (m, 9H), 7.06 (d, J=7.8 Hz, 2H), 7.03-6.94 (m, 3H), 6.86 (br s, 1H), 5.25 (m, 1H), 4.30 (dd, J=11.9, 4.4 Hz, 2H), 4.19 (m, 1H), 4.14 (dd, J=11.9, 5.8 Hz, 2H), 4.07 (m, 1H), 4.07 (t, J=6.6 Hz, 2H), 3.82 (m, 1H), 3.70 (m, 1H), 3.57 (m, 1H), 2.48 (dd, J=15.7, 7.0 Hz, 1H), 2.36-2.27 (m, 7H), 1.70-1.58 (m, 10H), 1.53 (d, J=7.1 Hz, 6H), 1.36 (s, 3H), 1.29 (s, 3H), 1.44-1.20 (m, 51H), 1.05 (m, 1H), 0.88 (t, J=6.9 Hz, 6H).

as(iii) 2-((6-(((3R,5R)-7-(2-(4-Fluorophenyl)-5-isopropyl-3-phenyl-4-(phenylcarbamoyl)-1H-pyrrol-1-yl)-3,5-dihydroxyheptanoyl)oxy)hexanoyl)oxy)propane-1,3-diyl dipalmitate (9)

p-Toluenesulfonic acid (1.6 mg, 8.4 mmol) was added to a solution of the acetonide XLV (35.2 mg, 27.9 mmol) in CH$_2$Cl$_2$ (0.5 mL) and MeOH (1 mL) and the reaction stirred at rt for 5.5 hours. The reaction was diluted with CH$_2$Cl$_2$ (20 mL) and the organic phase washed with sat. aq. NaHCO$_3$ (15 mL) and brine (15 mL), dried (MgSO$_4$) and concentrated under reduced pressure to give the crude product. Purification by silica gel chromatography (20% to 35% ethyl acetate/hexanes) gave Compound 9 (14.6 mg, 43%) as a colourless oil.

$^1$H NMR (400 MHz, CDCl$_3$) δ 7.22-7.13 (m, 9H), 7.06 (d, J=7.6 Hz, 2H), 7.02-6.96 (m, 3H), 6.85 (br s, 1H), 5.25 (m, 1H), 4.30 (dd, J=11.9, 4.4 Hz, 2H), 4.16 (m, 1H), 4.14 (dd, J=11.9, 5.6 Hz, 2H), 4.10 (t, J=7.5 Hz, 2H), 4.10 (m, 1H), 3.94 (m, 1H), 3.74 (m, 1H), 3.58 (m, 1H), 2.40 (d, J=6.1 Hz, 2H), 2.33 (t, J=7.4 Hz, 2H), 2.31 (t, J=7.6 Hz, 4H), 1.73-1.51 (m, 10H), 1.54 (d, J=7.4 Hz, 6H), 1.50-1.34 (m, 3H), 1.33-1.20 (m, 49H), 0.88 (t, J=6.9 Hz, 1H).

Further exemplary compounds of the formula (I) wherein L represents X'C(O) are provided below in Table 6.

TABLE 6

$^1$H NMR data for representative compounds of formula (I)

| Compound No. | R$^5$ | R$^6$ | n | X' | $^1$H NMR (400 MHz, CDCl$_3$) |
|---|---|---|---|---|---|
| 31 | H | H | 2 | O | δ 7.68 (s, 1H), 5.28-5.21 (m, 2H), 5.19 (s, 2H), 4.30 (dd, J = 11.9, 4.4 Hz, 2H), 4.13 (dd, J = 11.9, 5.8 Hz, 2H), 4.02 (t, J = 6.0 Hz, 2H), 3.76 (s, 3H), 3.38 (d, J = 6.8 Hz, 2H), 2.44-2.25 (m, 10H), 2.14 (s, 3H), 1.79 (s, 3H), 1.73-1.53 (m, 8H), 1.35-1.18 (m, 48H), 0.87 (t, J = 6.8 Hz, 6H). |
| 32 | H | H | 3 | O | δ 7.68 (s, 1H), 5.29-5.21 (m, 2H), 5.20 (s, 2H), 4.29 (dd, J = 11.9, 4.4 Hz, 2H), 4.14 (dd, J = 11.9, 5.9 Hz, 2H), 4.01 (t, J = 6.7 Hz, 2H), 3.76 (s, 3H), 3.38 (d, J = 6.8 Hz, 2H), 2.42-2.27 (m, 10H), 2.15 (s, 3H), 1.80 (s, 3H), 1.68-1.56 (m, 10H), 1.33-1.19 (m, 48H), 0.88 (t, J = 6.9 Hz, 6H). |
| 33 | H | H | 5 | O | δ 7.67 (s, 1H), 5.29-5.21 (m, 2H), 5.20 (s, 2H), 4.29 (dd, J = 11.9, 4.4 Hz, 2H), 4.14 (dd, J = 11.9, 5.9 Hz, 2H), 4.00 (t, J = 6.7 Hz, 2H), 3.75 (s, 3H), 3.38 (d, J = 6.9 Hz, 2H), 2.42-2.35 (m, 2H), 2.34-2.26 (m, 8H), 2.14 (s, 3H), 1.79 (s, 3H), 1.66-1.54 (m, 8H), 1.35-1.19 (m, 54H), 0.87 (t, J = 6.8 Hz, 6H). |
| 34 | H | H | 12 | O | δ 7.67 (s, 1H), 5.29-5.21 (m, 2H), 5.19 (s, 2H), 4.29 (dd, J = 11.9, 4.3 Hz, 2H), 4.14 (dd, J = 11.9, 5.9 Hz, 3H), 4.00 (t, J = 6.8 Hz, 2H), 3.75 (s, 3H), 3.38 (d, J = 6.9 Hz, 2H), 2.42-2.34 (m, 2H), 2.34-2.26 (m, 8H), 2.14 (s, 3H), 1.79 (s, 3H), 1.64-1.53 (m, 8H), 1.35-1.21 (m, 68H), 0.87 (t, J = 6.9 Hz, 6H). |
| 35 | H | H | 18 | O | δ 7.67 (s, 1H), 5.30-5.21 (m, 2H), 5.19 (s, 2H), 4.29 (dd, J = 11.9, 4.3 Hz, 2H), 4.14 (dd, J = 11.9, 6.0 Hz, 2H), 4.00 (t, J = 6.8 Hz, 2H), 3.76 (s, 3H), 3.38 (d, J = 6.9 Hz, 2H), 2.43-2.35 (m, 2H), 2.34-2.27 (m, 8H), 2.14 (s, 3H), 1.80 (s, 3H), 1.67-1.52 (m, 8H), 1.38-1.18 (m, 80H), 0.87 (t, J = 6.8 Hz, 6H). |

TABLE 6-continued

¹H NMR data for representative compounds of formula (I)

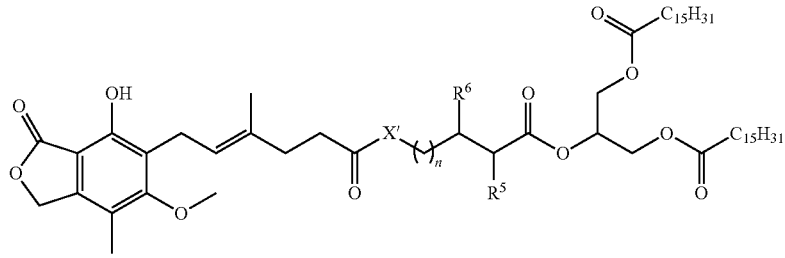

| Compound No. | R⁵ | R⁶ | n | X' | ¹H NMR (400 MHz, CDCl₃) |
|---|---|---|---|---|---|
| 36 | methyl | H | 2 | O | δ 7.68 (s, 1H), 5.29-5.21 (m, 2H), 5.19 (s, 2H), 4.29 (dd, J = 11.9, 4.3 Hz, 2H), 4.13 (dd, J = 11.9, 6.0 Hz, 2H), 4.04-3.97 (m, 2H), 3.76 (s, 3H), 3.38 (d, J = 6.8 Hz, 2H), 2.46 (m, 1H), 2.43-2.35 (m, 2H), 2.34-2.25 (m, 6H), 2.14 (s, 3H), 1.79 (s, 3H), 1.74-1.54 (m, 7H), 1.46 (m, 1H), 1.35-1.19 (m, 48H), 1.15 (d, J = 7.0 Hz, 3H), 0.87 (t, J = 6.9 Hz, 6H). |
| 37 | methyl | H | 3 | O | δ 7.67 (s, 1H), 5.28-5.20 (m, 2H), 5.19 (s, 2H), 4.29 (dd, J = 11.9, 4.3 Hz, 2H), 4.13 (dd, J = 11.9, 5.9 Hz, 2H), 4.00 (t, J = 6.7 Hz, 2H), 3.75 (s, 3H), 3.38 (d, J = 6.9 Hz, 2H), 2.44 (m, 1H), 2.40-2.35 (m, 2H), 2.33-2.25 (m, 6H), 2.14 (s, 3H), 1.79 (s, 3H), 1.72-1.54 (m, 8H), 1.47-1.19 (m, 50H), 1.14 (d, J = 7.0 Hz, 3H), 0.87 (t, J = 6.8 Hz, 6H). |
| 38 | H | methyl | 2 | O | δ 7.68 (s, 1H), 5.30-5.21 (m, 2H), 5.19 (s, 2H), 4.29 (dd, J = 11.9, 4.3 Hz, 2H), 4.13 (dd, J = 11.9, 5.8 Hz, 2H), 4.10-4.02 (m, 2H), 3.75 (s, 3H), 3.38 (d, J = 6.9 Hz, 2H), 2.41-2.35 (m, 2H), 2.33-2.26 (m, 7H), 2.17 (dd, J = 14.9, 8.1 Hz, 1H), 2.14 (s, 3H), 2.06 (m, 1H), 1.79 (s, 3H), 1.66 (m, 1H), 1.63-1.55 (m, 4H), 1.49 (m, 1H), 1.36-1.19 (m, 48H), 0.96 (d, J = 6.6 Hz, 3H), 0.87 (t, J = 6.9 Hz, 6H). |
| 39 | H | methyl | 12 | O | δ 7.68 (s, 1H), 5.32-5.22 (m, 2H), 5.20 (s, 2H), 4.29 (dd, J = 11.9, 4.3 Hz, 2H), 4.14 (dd, J = 11.8, 6.0 Hz, 2H), 4.00 (t, J = 6.8 Hz, 2H), 3.76 (s, 3H), 3.38 (d, J = 7.0 Hz, 2H), 2.42-2.26 (m, 9H), 2.15 (s, 3H), 2.11 (dd, J = 14.7, 8.3 Hz, 1H), 1.93 (m, 1H), 1.80 (s, 3H), 1.65-1.56 (m, 6H), 1.35-1.15 (m, 68H), 0.93 (d, J = 6.6 Hz, 3H), 0.88 (t, J = 6.9 Hz, 6H). |
| 40 | H | H | 2 | S | δ 7.68 (s, 1H), 5.28-5.21 (m, 2H), 5.20 (s, 2H), 4.29 (dd, J = 11.9, 4.3 Hz, 2H), 4.13 (dd, J = 11.9, 5.9 Hz, 2H), 3.76 (s, J = 1.9 Hz, 3H), 3.38 (d, J = 7.0 Hz, 2H), 2.83 (t, J = 7.1 Hz, 2H), 2.65-2.57 (m, 2H), 2.37-2.25 (m, 8H), 2.14 (s, 3H), 1.79 (s, 3H), 1.72-1.54 (m, 8H), 1.35-1.23 (m, 48H), 0.87 (t, J = 6.9 Hz, 6H). |

Example 7. Methods for Preparing Compounds of the Formula (I) Wherein Z Represents C(O)R³ and R³ Represents a p-Hydroxybenzyl Carbonyl (PHB) Self-Immolative Group and L Represents X' where X' is O, S or NR⁴

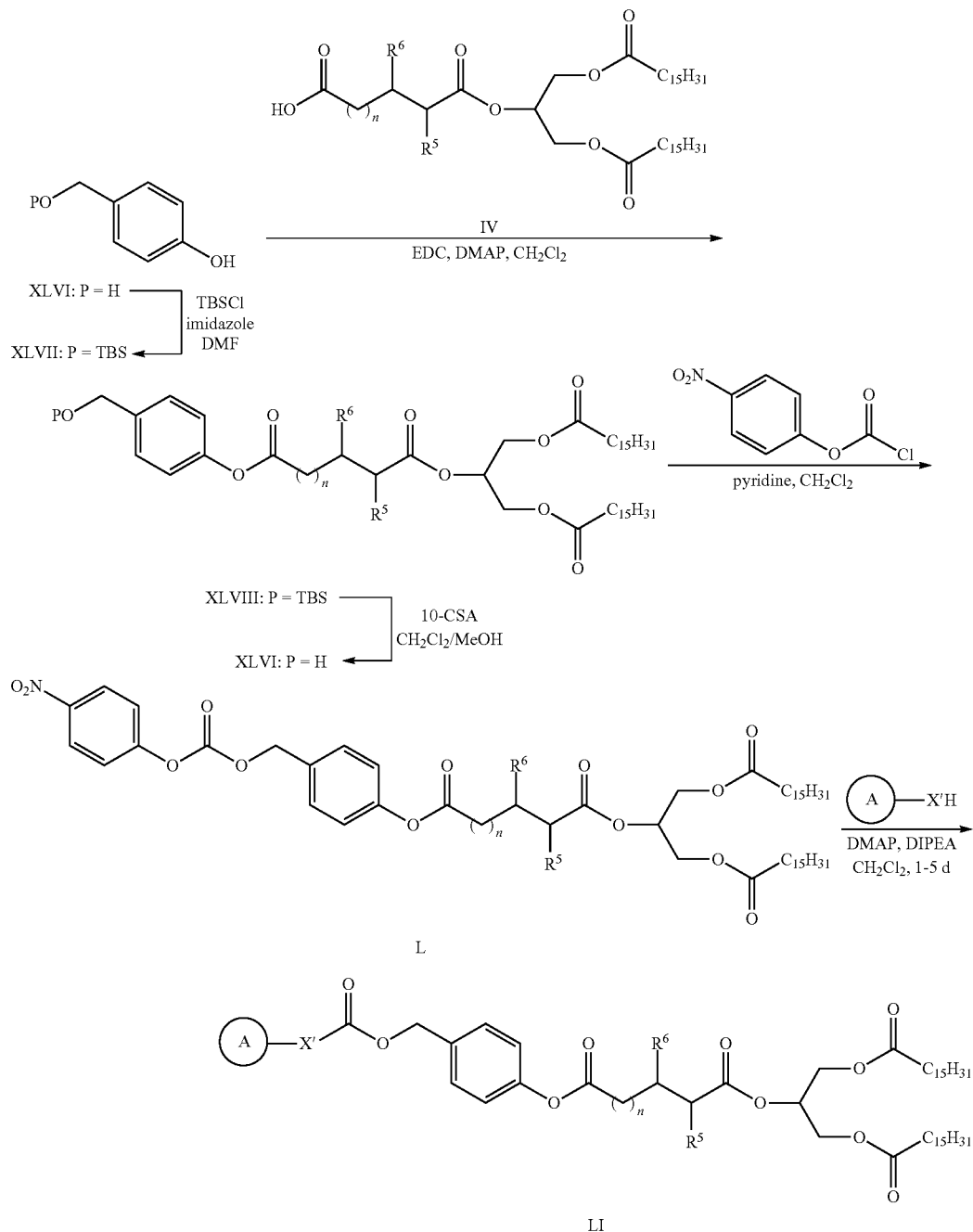

Scheme 8. Synthesis of compounds with a p-hydroxybenzyl carbonyl self-immolative linker For the synthesis of prodrugs containing a p-hydroxybenzyl (PHB) carbonyl self-immolative group, the primary hydroxyl group of p-hydroxybenzyl alcohol (XLVI) is first protected as a silyl ether and the free phenolic hydroxyl group coupled with acid-TG IV to give PHB triglyceride XLVIII. After removal of the silicon protecting group, primary alcohol XLIX can be activated by treatment with p-nitrophenyl (PNP) chloroformate to give PNP carbonate L. Displacement of the PNP group is then achieved by reaction with a pharmaceutical agent (AX'H) under basic conditions to give the desired PHB prodrug LI.

at) 4-(((tert-Butyldimethylsilyl)oxy)methyl)phenol (XLVII)

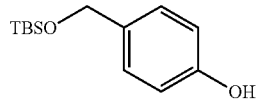 [SMILES: CC(C)(C)[Si](C)(C)OCc1ccc(O)cc1]

Imidazole (85.1 mg, 1.25 mmol) and tert-butyl(chloro)dimethylsilane (TBSCl, 90.4 mg, 0.600 mmol) were added to a solution of 4-hydroxybenzyl alcohol (XLVI) (62.1 mg, 0.500 mmol) in DMF (4 mL) and the mixture stirred at rt for 45 minutes. The reaction was diluted with ethyl acetate (30 mL) and the organic phase washed with water (30 mL), sat. aq. NaHCO$_3$ (30 mL) and brine (30 mL), dried (MgSO$_4$) and concentrated under reduced pressure to give TBS ether XLVII (119 mg, quant.) as a colourless oil that was used without purification.

$^1$H NMR (400 MHz, CDCl$_3$) δ 7.21-7.15 (m, 2H), 6.83-6.78 (m, 2H), 4.66 (s, 2H), 0.93 (s, 9H), 0.08 (s, 6H).

au) 1-(1,3-Bis(palmitoyloxy)propan-2-yl) 10-(4-(((tert-butyldimethylsilyl)oxy)methyl)-phenyl) decanedioate (XLVIII)

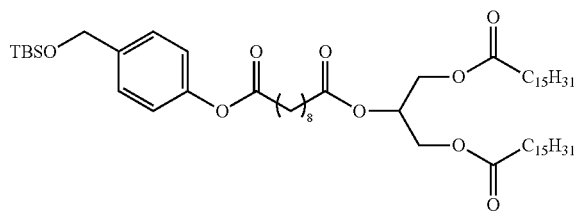

4-(Dimethylamino)pyridine (DMAP, 11.8 mg, 0.0966 mmol) and EDC.HCl (46.3 mg, 0.241 mmol) were added to a solution of acid-TG IV (80.0 mg, 0.106 mmol) and phenol XLVII (23.0 mg, 0.0966 mmol) in CH$_2$Cl$_2$ (2.5 mL) and the mixture stirred at rt for 18 hours. The reaction was diluted with CH$_2$Cl$_2$ (10 mL), silica gel was added and the mixture concentrated under reduced pressure. Purification by silica gel chromatography (5% to 7.5% to 10% ethyl acetate/hexanes) gave PHB triglyceride XLVIII (60.7 mg, 65% over two steps) as a colourless oil.

$^1$H NMR (400 MHz, CDCl$_3$) δ 7.35-7.28 (m, 2H), 7.05-6.99 (m, 2H), 5.26 (m, 1H), 4.72 (s, 2H), 4.29 (dd, J=11.9, 4.3 Hz, 2H), 4.14 (dd, J=11.9, 5.9 Hz, 2H), 2.53 (t, J=7.5 Hz, 2H), 2.32 (t, J=7.5 Hz, 2H), 2.30 (t, J=7.5 Hz, 4H), 1.78-1.70 (m, 2H), 1.67-1.55 (m, 6H), 1.43-1.20 (m, 56H), 0.93 (s, 9H), 0.87 (t, J=6.8 Hz, 6H), 0.09 (s, 6H).

av) 1-(1,3-Bis(palmitoyloxy)propan-2-yl) 10-(4-(hydroxymethyl)phenyl) decanedioate (XLIX)

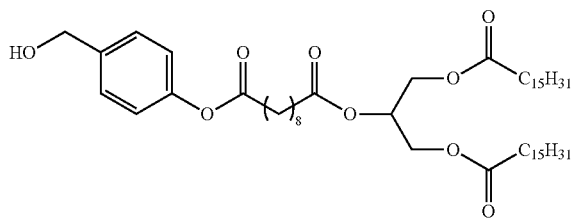

10-Camphorsulfonic acid (2.1 mg, 8.91 µmol) was added to TBS ether XLVIII (57.8 mg, 59.4 µmol) in CH$_2$Cl$_2$ (0.8 mL) and MeOH (0.8 mL) and the mixture stirred at rt for two hours. The reaction was diluted with CH$_2$Cl$_2$ (20 mL) and the organic phase washed with sat. aq. NaHCO$_3$ and brine (20 mL each), dried (MgSO$_4$) and concentrated under reduced pressure to give the crude product. Purification by silica gel chromatography (25% to 35% ethyl acetate/hexanes) gave alcohol XLIX (46.9 mg, 92%) as a colourless solid.

$^1$H NMR (400 MHz, CDCl$_3$) δ 7.41-7.32 (m, 2H), 7.10-7.01 (m, 2H), 5.25 (m, 1H), 4.67 (s, 2H), 4.28 (dd, J=11.9, 4.3 Hz, 2H), 4.14 (dd, J=11.9, 5.9 Hz, 2H), 2.54 (t, J=7.5 Hz, 2H), 2.31 (t, J=7.5 Hz, 2H), 2.30 (t, J=7.5 Hz, 4H), 1.89 (br s, 1H), 1.78-1.70 (m, 2H), 1.65-1.55 (m, 6H), 1.46-1.20 (m, 56H), 0.87 (t, J=6.9 Hz, 6H).

aw) 1-(1,3-Bis(palmitoyloxy)propan-2-yl) 10-(4-((((4-nitrophenoxy)carbonyl)oxy)meth-yl)phen-yl) decanedioate (L)

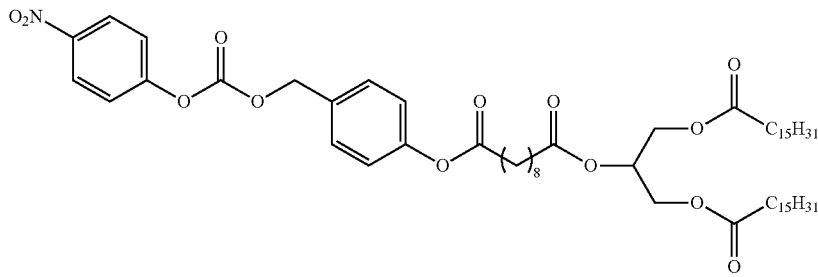

4-Nitrophenyl chloroformate (13.9 mg, 69.1 µmol) and pyridine (7.8 µL, 96.0 µL) were added to alcohol XLIX (33.0 mg, 38.4 µmol) in $CH_2Cl_2$ (2 mL) at 0° C. and the mixture stirred at 0° C. for 20 minutes and then at rt for 2.5 hours. The reaction was diluted with $CH_2Cl_2$ (20 mL) and the organic phase washed with sat. aq. $NaHCO_3$ and brine (20 mL each), dried ($MgSO_4$) and concentrated under reduced pressure to give the crude product. Purification by silica gel chromatography (10% to 20% ethyl acetate/hexanes) gave PNP carbonate L (38.7 mg, 98%) as a colourless solid.

$^1$H NMR (400 MHz, $CDCl_3$) δ 8.30-8.23 (m, 2H), 7.49-7.43 (m, 2H), 7.41-7.35 (m, 2H), 7.15-7.09 (m, 2H), 5.28 (s, 2H), 5.26 (m, 1H), 4.30 (dd, J=11.9, 4.3 Hz, 2H), 4.15 (dd, J=11.9, 5.9 Hz, 2H), 2.56 (t, J=7.5 Hz, 2H), 2.32 (t, J=7.5 Hz, 2H), 2.31 (t, J=7.5 Hz, 4H), 1.79-1.71 (m, 2H), 1.66-1.55 (m, 6H), 1.45-1.20 (m, 56H), 0.87 (t, J=6.9 Hz, 6H).

ax) 1-(1,3-Bis(palmitoyloxy)propan-2-yl) 10-(4-((((((8R,9S,10R,13S,14S,17S)-10,13-di-methyl-3-oxo-2,3,6,7,8,9,10,11,12,13,14,15,16,17-tetradeca-hydro-1H-cyclopenta[a]-phenanthren-17-yl)oxy)carbonyl)oxy)methyl)phenyl) decanedioate (28)

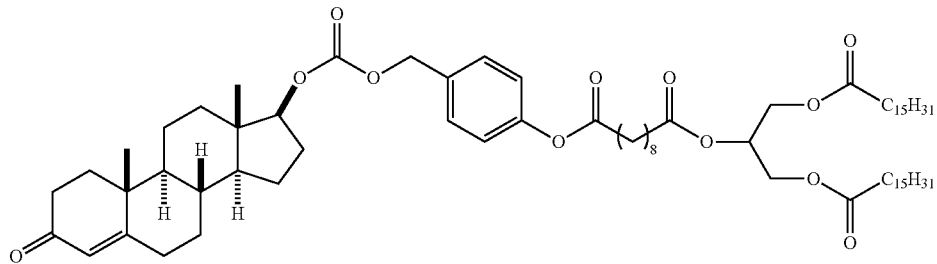

28

4-(Dimethylamino)pyridine (DMAP, 6.2 mg, 50.8 µmol) and DIPEA (0.16 M in $CH_2Cl_2$, 80.0 µL, 12.7 µmol) were added to a solution of testosterone (11.7 mg, 40.6 µmol) and PNP carbonate L (26.0 mg, 25.4 µmol) in $CH_2Cl_2$ (0.8 mL) and the mixture stirred at rt for four days and 20 hours. The reaction was diluted with $CH_2Cl_2$ (20 mL), washed with sat. aq. $NaHCO_3$ and brine (2×15 mL each), dried ($MgSO_4$) and concentrated under reduced pressure to give the crude product. Purification by silica gel chromatography (10% to 20% ethyl acetate/hexanes) gave Compound 28 (9.8 mg, 33%) as a colourless solid.

$^1$H NMR (400 MHz, $CDCl_3$) δ 7.43-7.38 (m, 2H), 7.10-7.05 (m, 2H), 5.73 (s, 1H), 5.26 (m, 1H), 5.12 (s, 2H), 4.52 (dd, J=8.9, 7.8 Hz, 1H), 4.29 (dd, J=11.9, 4.3 Hz, 2H), 4.14 (dd, J=11.9, 5.9 Hz, 2H), 2.54 (t, J=7.5 Hz, 2H), 2.47-2.17 (m, 11H), 2.02 (m, 1H), 1.89-1.81 (m, 2H), 1.78-1.54 (m, 12H), 1.47-1.19 (m, 59H), 1.18 (s, 3H), 1.10-0.93 (m, 4H), 0.87 (t, J=6.8 Hz, 6H), 0.85 (s, 3H).

ay) 1-(1,3-Bis(palmitoyloxy)propan-2-yl) 10-(4-(((((1S,4S)-4-(3,4-dichlorophenyl)-1,2,3,4-tetrahy-dronaphthalen-1-yl)(methyl)carbamoyl)oxy)methyl)phenyl) decanedioate (6)

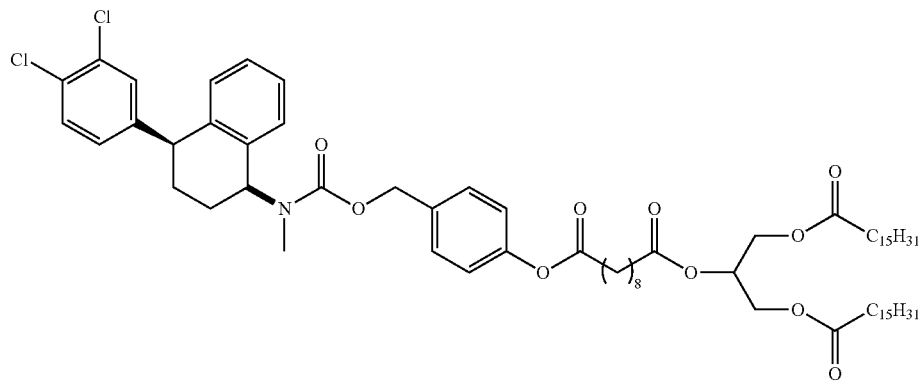

4-(Dimethylamino)pyridine (DMAP, 6.3 mg, 51.2 µmol) and DIPEA (0.59 M in CH₂Cl₂, 10.0 µL, 5.9 µmol) were added to a solution of sertraline hydrochloride (10.0 mg, 29.3 mol) and PNP carbonate L (15.0 mg, 14.6 µmol) in CH₂Cl₂ (0.6 mL) and the mixture stirred at rt for 18 hours. The reaction was diluted with CH₂Cl₂ (25 mL), washed with sat. aq. NaHCO₃ (3×20 mL) and brine (20 mL), dried (MgSO₄) and concentrated under reduced pressure to give the crude product. Purification by silica gel chromatography (3% to 6% ethyl acetate/toluene) gave Compound 6 (11.3 mg, 65%) as a colourless solid.

¹H NMR (400 MHz, CDCl₃) δ 7.46-7.28 (m, 3.5H), 7.25-7.16 (m, 2.5H), 7.12-7.02 (m, 3H), 6.95 (d, J=7.2 Hz, 1H), 6.81 (m, 1H), 5.51 (m, 0.6H), 5.36 (m, 0.4H), 5.27 (m, 1H), 5.20 (s, 2H), 4.29 (dd, J=11.9, 4.3 Hz, 2H), 4.19 (m, 1H), 4.15 (dd, J=11.9, 5.6 Hz, 2H), 4.15 (dd, J=11.6, 5.6 Hz, 1H), 2.73 (s, 1.2H), 2.69 (s, 1.8H), 2.59-2.52 (m, 2H), 2.36-2.24 (m, 7H), 2.00 (m, 1H), 1.83-1.69 (m, 4H), 1.66-1.55 (m, 6H), 1.45-1.19 (m, 56H), 0.88 (t, J=6.9 Hz, 6H). Note: Fractional integrations reflect the presence of a ~3:2 mixture of rotational isomers due to restricted rotation around the N-methylcarbamate functionality.

Example 8. Methods for Preparing Compounds of the Formula (I) Wherein Z Represents C(O)R³ and R³ Represents a Flipped-Ester Self-Immolative Group and L Represents X' where X' is O, S or N(R⁴)

az) (8R,9S,10R,13S,14S,17S)-10,13-Dimethyl-3-oxo-2,3,6,7,8,9,10,11,12,13,14,15,16,17-tetradecahydro-1H-cyclopenta[a]phenanthren-17-yl 4-bromobutanoate (LII)

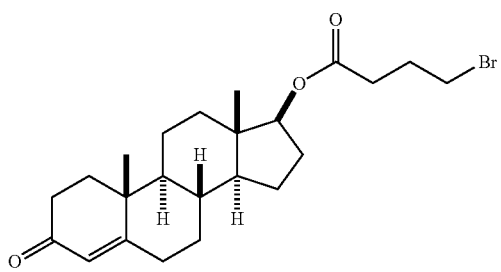

4-(Dimethylamino)pyridine (DMAP, 15.5 mg, 0.130 mmol) and DCC (43.8 mg, 0.210 mmol) were added to a solution of testosterone (29.9 mg, 0.100 mmol) and 4-bromobutyric acid (XXII) (21.0 mg, 0.130 mmol) in CH₂Cl₂ (3 mL) and the mixture stirred at rt for 24 hours. Another 0.6 eq. of acid, 1 eq. of DCC, 0.6 eq. of DMAP were added and the mixture was stirred at rt for a further two days. The reaction was diluted with CH₂Cl₂ (10 mL), silica gel was added and the mixture concentrated under reduced pressure.

Scheme 9: Synthesis of compounds with a flipped-ester self-immolative (FSI) linker

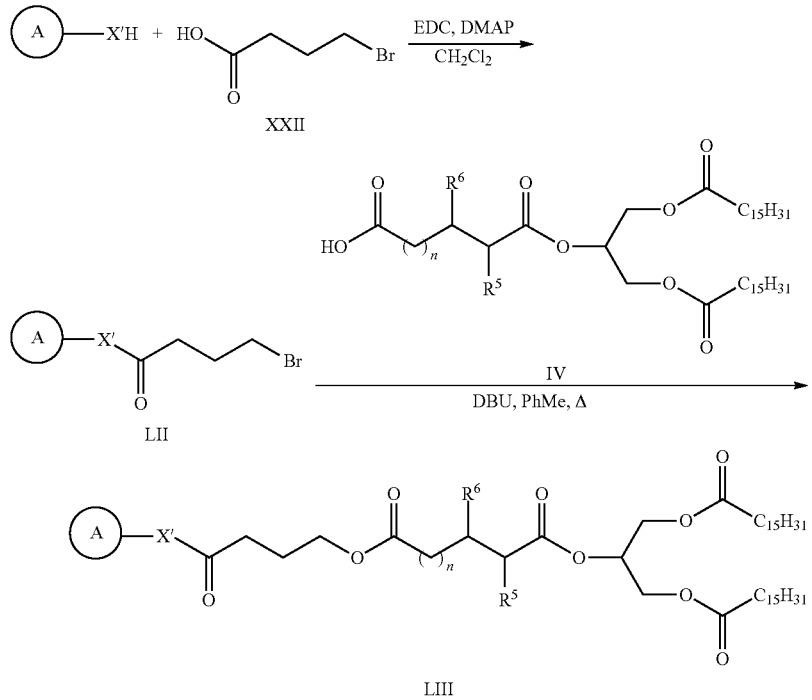

The flipped-ester self-immolative (FSI) group has been designed to liberate the free pharmaceutical agent by a cyclisation mechanism. FSI prodrugs can be synthesised by coupling of a pharmaceutical agent (A-X'H) with 4-bromobutyric acid (XXII) to give bromide LII. Displacement of bromide LII using the carboxylate derived from acid-TG IV generates the desired ester bond in target FSI prodrug LIII.

Purification by silica gel chromatography (25% ethyl acetate/hexanes) gave bromide LII (26.7 mg, 59%) as a colourless solid.

¹H NMR (400 MHz, CDCl₃) δ 5.73 (s, 1H), 4.62 (dd, J=9.1, 7.9 Hz, 1H), 3.47 (t, J=6.5 Hz, 2H), 2.50 (td, J=7.1, 1.0 Hz, 2H), 2.47-2.23 (m, 4H), 2.22-2.13 (m, 3H), 2.06-1.99 (m, 1H), 1.85 (m, 1H), 1.78 (m, 1H), 1.74-1.63 (m, 2H), 1.61-1.53 (m, 2H), 1.52-1.32 (m, 3H), 1.23-1.15 (m, 1H), 1.19 (s, 3H) 1.11-0.91 (m, 3H), 0.83 (s, 3H).

ba) 1-(1,3-Bis(palmitoyloxy)propan-2-yl) 5-(4-(((8R,9S,10R,13S,14S,17S)-10,13-dimeth-yl-3-oxo-2,3,6,7,8,9,10,11,12,13,14,15,16,17-tetradecahydro-1H-cyclopenta[a]phen-anthren-17-yl)oxy)-4-oxobutyl) 3-methylpentanedioate (29)

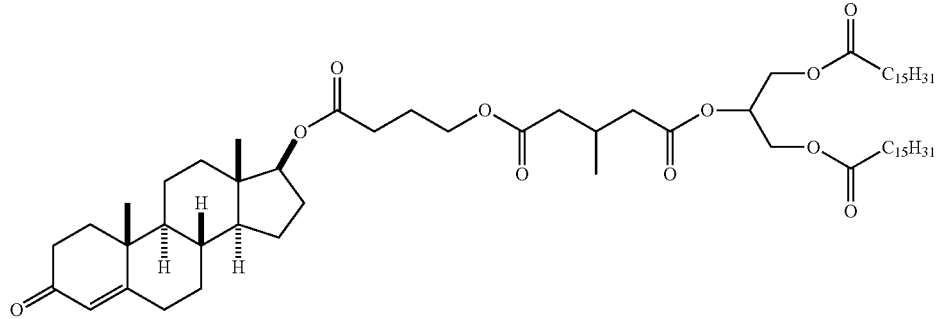

1,8-Diazabicyclo[5.4.0]undec-7-ene (DBU) (19 µL, 125.7 µmol) was added to a suspension of acid-TG IV (43.8 mg, 62.9 µmol), bromide LII (27.5 mg, 62.9 µmol) and tetra-butylammonium iodide (TBAI, 11.6 mg, 31.4 µmol) in toluene (3 mL) and the mixture heated at reflux for 6 hours. The reaction was cooled to rt, then diluted with ethyl acetate (10 mL) and water (10 mL) and the aqueous layer extracted with ethyl acetate (3×10 mL). The combined organic extracts were washed with water (20 mL) and brine (20 mL), dried (MgSO$_4$) and concentrated under reduced pressure to give the crude product. Silica gel chromatography (15% to 35% ethyl acetate/hexane) gave Compound 29 (18.6 mg, 28%) as a colourless solid.

$^1$H NMR (400 MHz, CDCl$_3$) δ 5.72 (s, 1H), 5.26 (m, 1H), 4.61 (dd, J=9.1, 7.9 Hz, 1H), 4.29 (ddd, J=11.9, 4.3, 1.6 Hz, 2H), 4.12 (m, 4H), 2.50-2.12 (m, 16H), 2.03-1.92 (m, 3H), 1.84 (m, 1H), 1.77 (m, 1H), 1.74-1.54 (m, 8H), 1.53-1.32 (m, 2H), 1.31-1.21 (m, 49H), 1.18 (s, 3H), 1.16 (m, 1H), 1.10-1.01 (m, 2H), 1.02 (d, J=6.5 Hz, 3H), 0.95 (m, 1H), 0.87 (t, J=6.9 Hz, 6H), 0.83 (s, 3H).

Example 8. Lymphatic Transport Studies in Rats

To confirm that the prodrugs described in the current invention were able to promote transport into the lymph, studies were conducted in rats where the mesenteric lymph duct was cannulated to allow continual collection of mesenteric lymph. Lipid formulations containing the compound of interest were then administered to the animals, the lymph collected and drug concentrations in the lymph subsequently quantified.

Lipid-based formulations of the compounds of the invention or control compounds were prepared as previously described (Trevaskis, N. L. et al., Pharmaceutical Research, 2005, 22(11), 1863-1870). Briefly, approximately 2 mg of the compound (1 mg in the case of Compound 35 and Compound 1), 40 mg oleic acid and 25 mg Tween 80 were mixed in a glass vial until equilibrated (gentle heat (below 50° C.) may be applied for a short period). An aqueous phase consisting of 5.6 mL (phosphate buffered saline (PBS, pH 7.4) was subsequently added to the lipid phase (in the case of control compounds including mycophenolic acid, metoprolol tartrate, atorvastatin calcium, aspirin, and sertraline hydrochloride, each compound was dissolved in PBS instead of the lipid phase for the preparation of control compound containing formulations) and the formulation emulsified by ultrasonication with a ultrasonic processor equipped with a 3.2-mm microprobe tip running at an amplitude of 240 µm and a frequency of 20 kHz for 2 min at room temperature. Compound concentrations in all formulations were verified using HPLC-MS.

Male Sprague-Dawley (SD) rats were selected for the lymphatic transport studies where the pharmaceutical agent was mycophenolic acid (MPA), metoprolol (MET), atorvastatin (ATV), sertraline (SER) or celecoxib (CEL). Female SD rats were selected for studies where testosterone was the pharmaceutical agent. This was to eliminate the potential for the relatively high and variable levels of endogenous testosterone in male rats interfering with the quantification of exogenously dosed testosterone. Rats (240-320 g) were maintained on a standard diet and fasted overnight with free access to water prior to experiments. Anaesthetised rats were placed on a heated pad at 37° C. and cannulas were inserted into the duodenum (for formulation administration and rehydration), mesenteric lymph duct (for lymph collection) and carotid artery (for blood collection) as previously described (Edwards et al. Advanced Drug Delivery Reviews 2001, 50(1), 45-60). Post-surgery, rats were re-hydrated for 0.5 h via intraduodenal infusion of normal saline at 2.8 mL/h. The lipid formulations were infused into the duodenum at 2.8 mL/h for 2 h, after which the infusion was changed to 2.8 mL/h normal saline for the remainder of the experiment. Lymph was continuously collected for 6 to 8 h into pre-weighed Eppendorf tubes containing 10 µL of 1,000 IU/mL heparin. The collection tubes were changed hourly and lymph flow was measured gravimetrically. Aliquots of hourly lymph samples were stored at −80° C. prior to assay.

Drug concentration in lymph is expressed as total drug and includes free drug and drug associated with different glycerides. This is assayed by hydrolysis of lymph (to liberate drug from any re-esterified glycerides) prior to assessment of free drug.

Transport of MPA, TST, MET, ATV, SER or CEL derivatives into lymph during each hourly collection period was calculated from the product of the volume of lymph collected and the measured concentrations in lymph. FIG. 1 illustrates the cumulative lymphatic transport of total testosterone related derivatives (% of administered dose) versus time in anaesthetised mesenteric lymph duct cannulated female SD rats following intraduodenal infusion of formulations from 0 to 2 h. Each Formulation contained 2 mg of the exemplified compound or the control, testosterone undecanoate (TU), dispersed in 40 mg oleic acid, 25 mg Tween 80 and 5.6 ml PBS. Data are presented as mean±SEM for TU (n=4), the compound previously described by Scriba et al in which testosterone is coupled to the triglyceride unit via succinic acid (Compound 41, n=4) and Compound 11 (n=3), and n=1 for Compound 10 and Compound 14. The embedded figure shows the terminal data points (cumulative % dose transported in lymph over 8 h) in the form of a bar graph. As is evident from FIG. 1 and Table 7, each of the exemplified compounds greatly enhanced the delivery of testosterone to the intestinal lymphatics by around 7-9 fold compared to the control TU.

TABLE 7

Lymphatic transport of total compound (% of administered dose) following intraduodenal infusion to anaesthetised, mesenteric lymph-duct cannulated rats (data are presented as mean ± SEM when n ≥ 3).

| Compound | Transport of total TST derivatives in lymph (% of dose) | Fold increase (compared with control group dosed with TU) |
|---|---|---|
| TU (n = 2) | 1.9 ± 0.3 | 1.0 |
| 41 (n = 4) | 13.4 ± 1.7 | 7.2 |
| 10 (n = 1) | 14.5 | 7.7 |
| 11 (n = 3) | 17.0 ± 1.6 | 9.0 |
| 14 (n = 1) | 14.4 | 7.7 |

Figure 2:
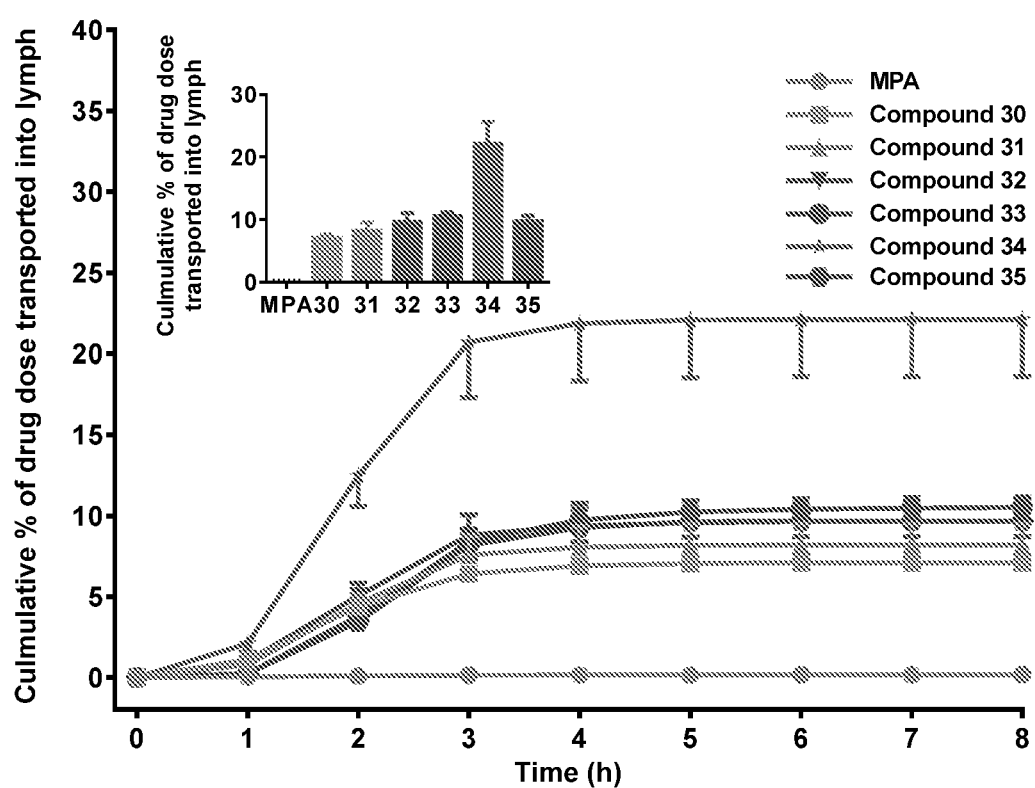
FIG. 2: Graphical representation of the cumulative lymphatic transport of total mycophenolic acid (MPA)-containing compounds (% of administered dose) versus time in anaesthetised, mesenteric lymph duct cannulated male SD rats following intraduodenal infusion of MPA and Compounds 30 to 35.

FIG. 2 illustrates the cumulative lymphatic transport of total MPA-containing compounds (% of administered dose) versus time in anaesthetised, mesenteric lymph duct cannulated male SD rats following intraduodenal infusion of formulations from 0 to 2 h. Formulations contained 2 mg of the exemplified compound or MPA alone dispersed in 40 mg oleic acid, 25 mg Tween 80 and 5.6 ml PBS. Data are presented as mean±SEM. Data obtained from animals with n=5 for MPA, n=3 for Compound 30 and Compound 34, n=6 for Compound 31, and n=4 for Compound 32, Compound 33 and Compound 35. The embedded figure shows the terminal data points (cumulative % dose transport in lymph over 8 h) in the form of a bar graph.

Figure 3:
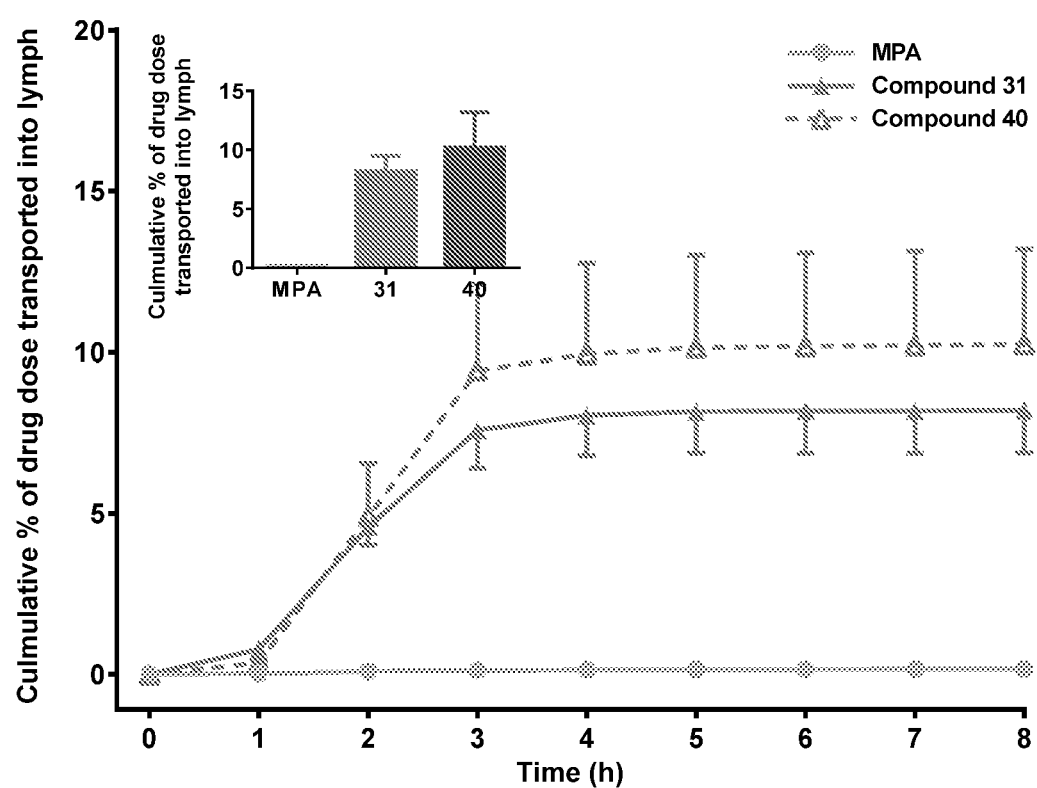
FIG. 3: Graphical representation of the cumulative lymphatic transport of total mycophenolic acid (MPA)-containing compounds (% of administered dose) versus time in anaesthetised, mesenteric lymph duct cannulated male SD rats following intraduodenal infusion of MPA and Compounds 31 and 40.

FIG. 2 and Table 8 illustrate that the compounds of the invention significantly increase lymphatic transport of MPA from 43-132 fold compared to MPA alone. Extending the linker length enhances transport of MPA, with Compound 30 improving the lymphatic transport of MPA to 7.1% of the administered dose and compound 34 enhancing transport to 22.1%. The correlation between linker length and increase in transportation is likely due to the ease of re-esterification of the monoglyceride intermediates, as the longer alkyl chains more closely mimic monoglyceride that results from digestion of natural triglyceride. Interestingly, increasing the linker length further was seen to be not as efficient and the administration of compound 35, where —Y— is a $C_{20}$ alkyl group, resulted in lower lymphatic transport than that attainable with Compound 34 where —Y— is a $C_{14}$ alkyl group. As can be seen from FIG. 3 and Table 8, replacing the ester bond between the pharmaceutical agent and the linker with a thioester does not alter lymphatic transport of the resultant compound (see, for example, Compound 31 and Compound 40).

TABLE 8

Lymphatic transport of total compound (% of administered dose) following intraduodenal infusion to anaesthetised, mesenteric lymph-duct cannulated rats (data are presented as mean ± SEM).

| Compound | Transport of total MPA derivatives in lymph (% of dose) | Fold increase (compared with MPA dosed group) |
|---|---|---|
| MPA (control, n = 5) | 0.17 ± 0.05 | 1.0 |
| 30 (n = 3) | 7.1 ± 0.5 | 42.5 |
| 31 (n = 6) | 8.2 ± 1.3 | 48.9 |
| 32 (n = 4) | 9.6 ± 1.4 | 57.5 |
| 33 (n = 4) | 10.5 ± 0.7 | 62.8 |
| 34 (n = 3) | 22.1 ± 3.5 | 132.0 |
| 35 (n = 4) | 9.7 ± 1.0 | 58.1 |
| 40 (n = 3) | 10.2 ± 3.0 | 61.1 |

Figure 4:
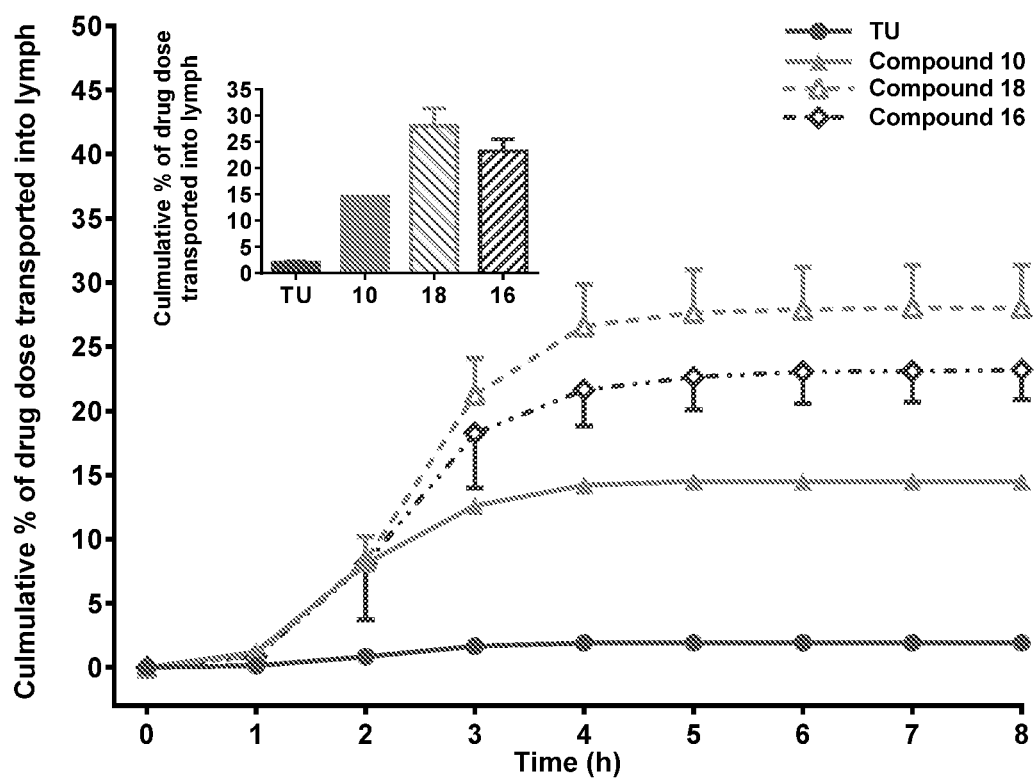
FIG. 4: Graphical representation of the cumulative lymphatic transport of total testosterone related derivatives (% of administered dose) versus time in anaesthetised, mesenteric lymph duct cannulated female SD rats following intraduodenal infusion of testosterone undecanoate (TU) and Compounds 10, 16 and 18.
Figure 19:
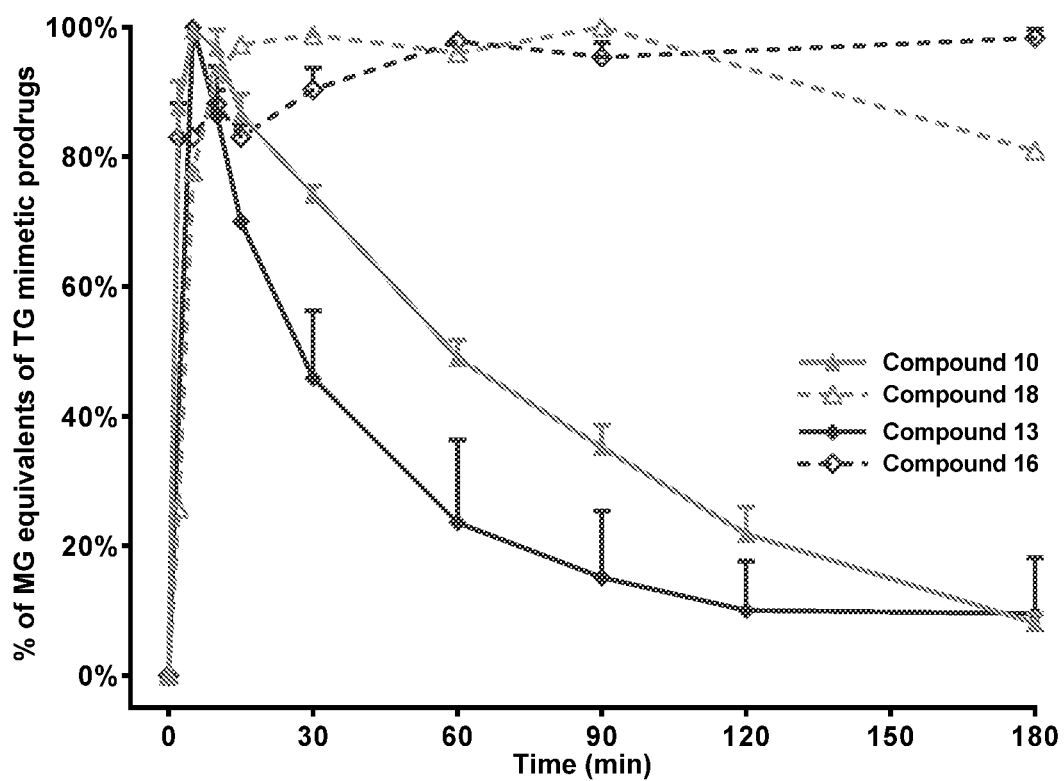
FIG. 19: Graphical representation of the stability profiles of the monoglyceride forms of Compounds 10, 13, 16 and Compound 18 during in vitro incubation with freshly collected rat bile and pancreatic fluid (for Compounds 10 and 18) or porcine pancreatic lipase (for Compounds 13 and 16).

As is evident from FIG. 4, FIG. 19 and Table 9, protecting the ester link to the glyceride subunit by either an alpha or a beta methyl group can increase the luminal stability of the compound and promote lymphatic transport. The beta methyl branch in Compound 18 or the alpha methyl branch in Compound 16 significantly stabilised the monoglyceride intermediates in gastrointestinal fluid when compared to their straight chain counterpart Compound 10 or Compound 13 (see FIG. 19). This allows for more of the monoglyceride-mimetic intermediate to be absorbed and re-esterified in the enterocytes and thus, a marked increase in lymphatic drug transport.

TABLE 9

Lymphatic transport of total compound (% of administered dose) following intraduodenal infusion to anaesthetised, mesenteric lymph-duct cannulated rats (data are presented as mean ± SEM when n ≥ 3 or mean ± range when n = 2).

| Compound | Transport of total TST derivatives in lymph (% of dose) | Fold increase (compared with TU dosed group) |
|---|---|---|
| TU (n = 2) | 1.9 ± 0.3 | 1.0 |
| 10 (n = 1) | 14.5 | 7.7 |
| 16 (n = 2) | 23.2 ± 2.3 | 12.3 |
| 18 (n = 4) | 28.0 ± 3.4 | 14.9 |

Figure 5:
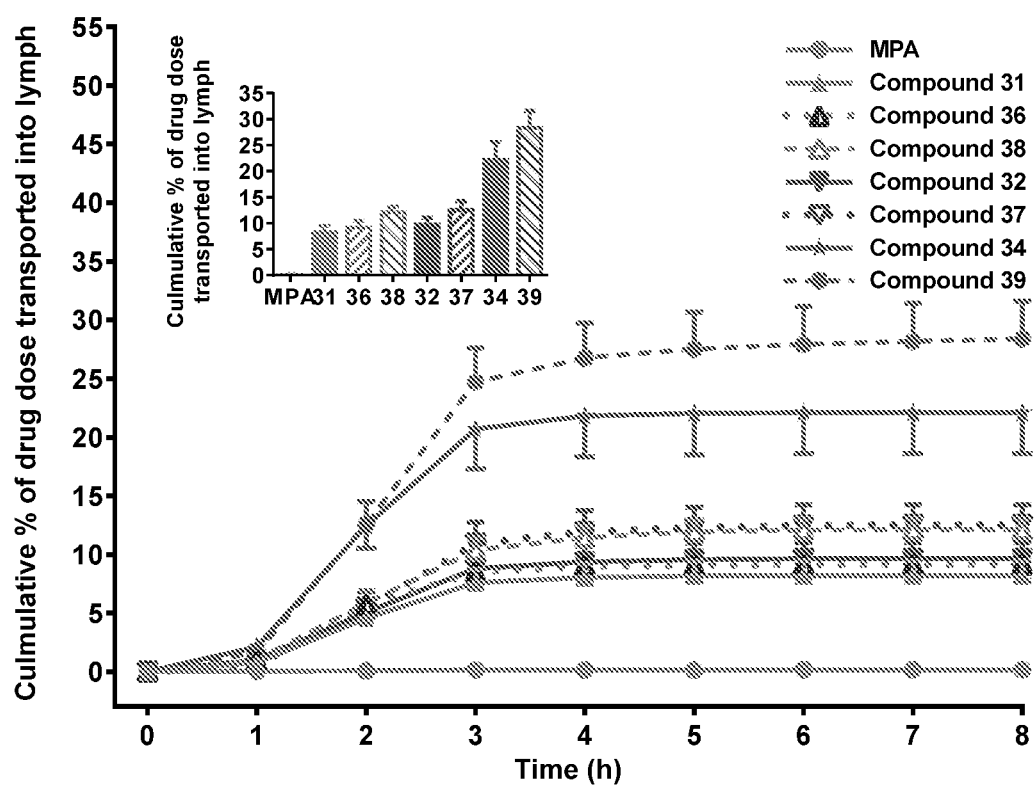
FIG. 5: Graphical representation of the cumulative lymphatic transport of total mycophenolic acid (MPA)-containing compounds (% of administered dose) versus time in anaesthetised, mesenteric lymph duct cannulated male SD rats following intraduodenal infusion of MPA and Compounds 31, 32, 34, 36, 37, 38 and 39.

Similarly, TG mimetic prodrugs with methyl substitution in the spacer (either α- or β- to the ester bond linking the alkyl spacer to the glyceride backbone) improved stability of MPA in the GI lumen (FIG. 23) and resulted in a trend towards better in vivo lymphatic transport of MPA (FIG. 5 and Table 10). FIG. 5 and Table 10 illustrates that lymphatic transport has improved for Compound 36 (9.1%) and Compound 38 (12.1%) compared to Compound 31 (8.2%), and that Compound 37 (12.6%) and Compound 39 (28.4%) lead to higher lymphatic transport than Compound 32 (9.6%) and Compound 34 (22.1%), respectively.

TABLE 10

Lymphatic transport of total MPA related derivatives (% of administered dose) following intraduodenal infusion to anaesthetised, mesenteric lymph-duct cannulated rats (data are presented as mean ± SEM).

| Compound | Transport of total MPA derivatives in lymph (% of dose) | Increase fold (compared with MPA dosed group) |
|---|---|---|
| MPA (n = 5) | 0.17 ± 0.05 | 1.0 |
| 31 (n = 6) | 8.2 ± 1.3 | 48.9 |

TABLE 10-continued

Lymphatic transport of total MPA related derivatives
(% of administered dose) following intraduodenal infusion
to anaesthetised, mesenteric lymph-duct cannulated
rats (data are presented as mean ± SEM).

| Compound | Transport of total MPA derivatives in lymph (% of dose) | Increase fold (compared with MPA dosed group) |
| --- | --- | --- |
| 36 (n = 4) | 9.1 ± 1.4 | 54.6 |
| 38 (n = 4) | 12.1 ± 1.0 | 72.3 |
| 32 (n = 4) | 9.6 ± 1.4 | 57.5 |
| 37 (n = 4) | 12.6 ± 1.7 | 75.0 |
| 34 (n = 3) | 22.1 ± 3.5 | 132.0 |
| 39 (n = 4) | 28.4 ± 3.2 | 167.0 |

Compounds of the invention, conjugated at the 2' position of the triglyceride via an ester bond, are more effective in promoting lymphatic transport when compared to conjugation at the 1' (or 3') position, or linked via ether bonds.

Figure 6:
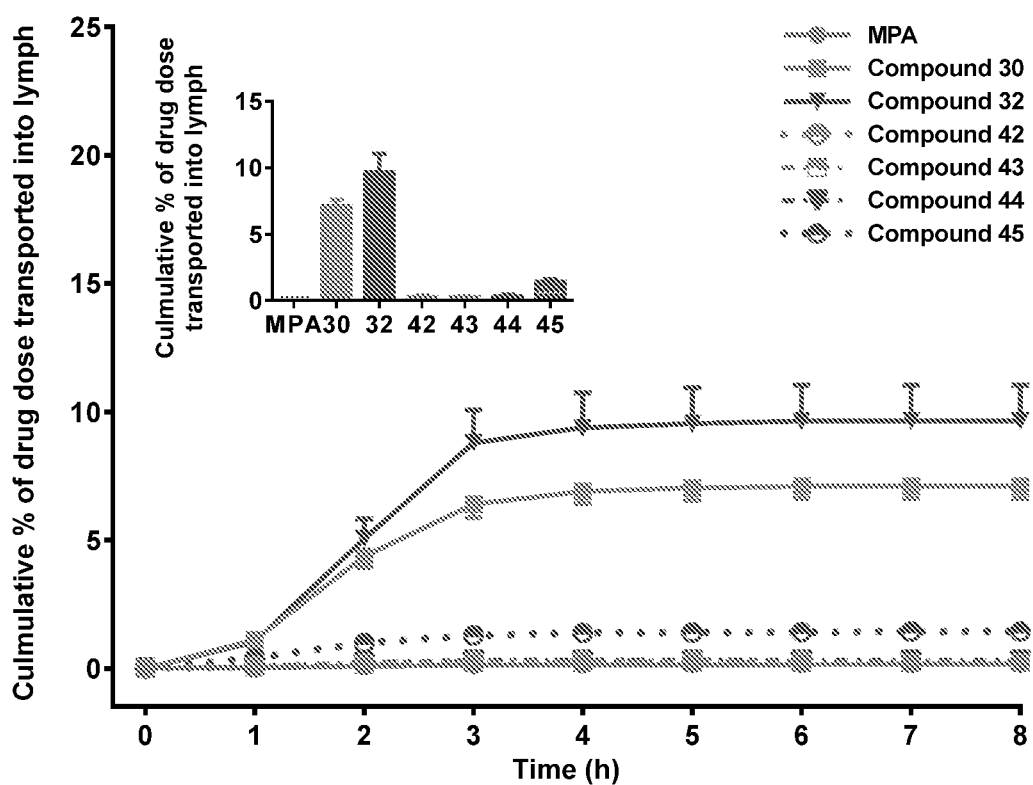
FIG. 6: Graphical representation of the cumulative lymphatic transport of total mycophenolic acid (MPA)-containing compounds (% of administered dose) versus time in anaesthetised, mesenteric lymph duct cannulated male SD rats following intraduodenal infusion of MPA and Compounds 30, 32, 42, 43, 44 and 45.
Figure 7:
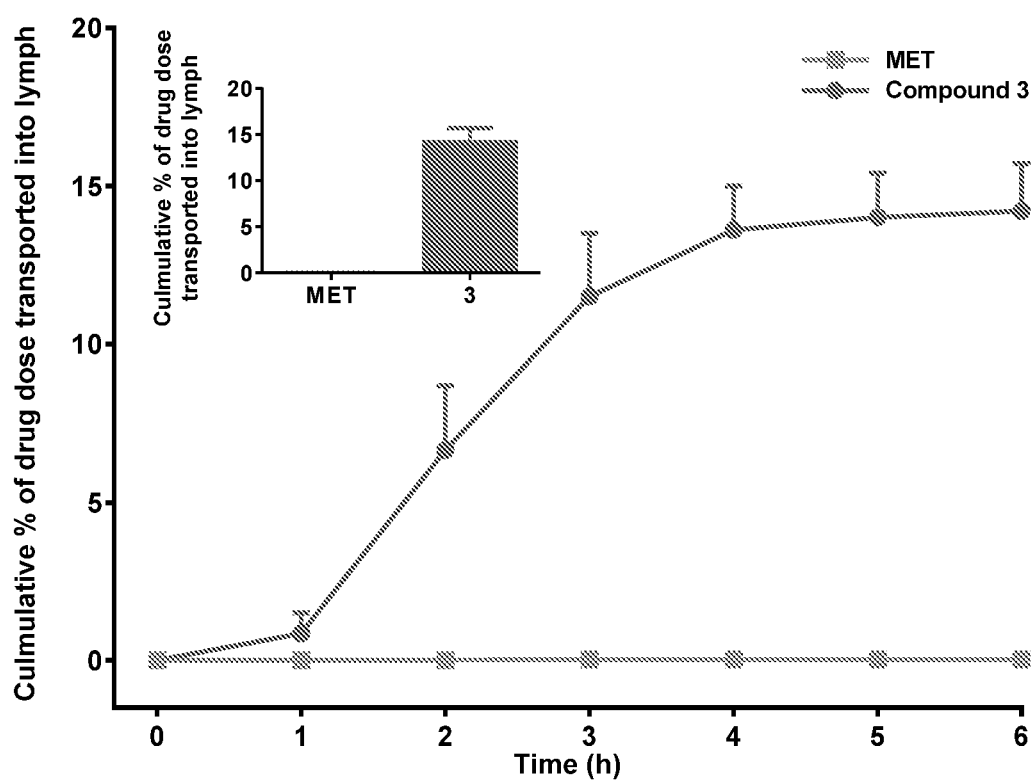
FIG. 7. Graphical representation of cumulative lymphatic transport of total metoprolol (MET) related derivatives (% of administered dose) versus time in anaesthetised, mesenteric lymph duct cannulated male SD rats following intraduodenal infusion of MET and Compound 3.
Figure 8:
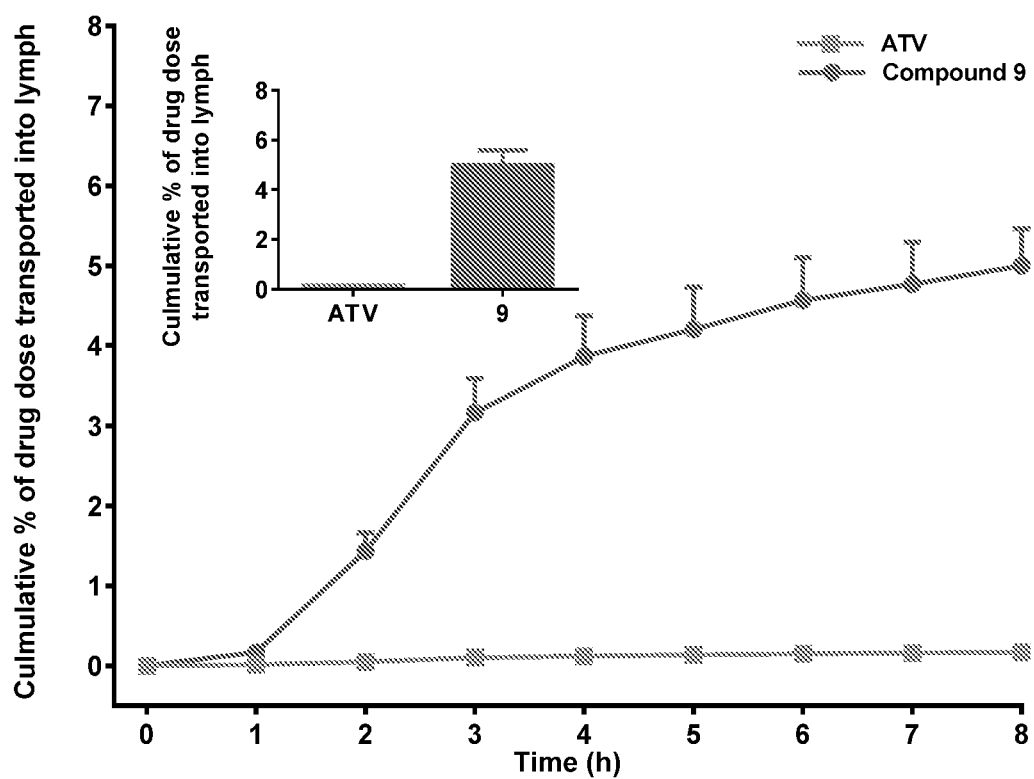
FIG. 8. Graphical representation of cumulative lymphatic transport of total atorvastatin (ATV) related derivatives (% of administered dose) versus time in anaesthetised, mesenteric lymph duct cannulated male SD rats following intraduodenal infusion of ATV and Compound 9.
Figure 9:
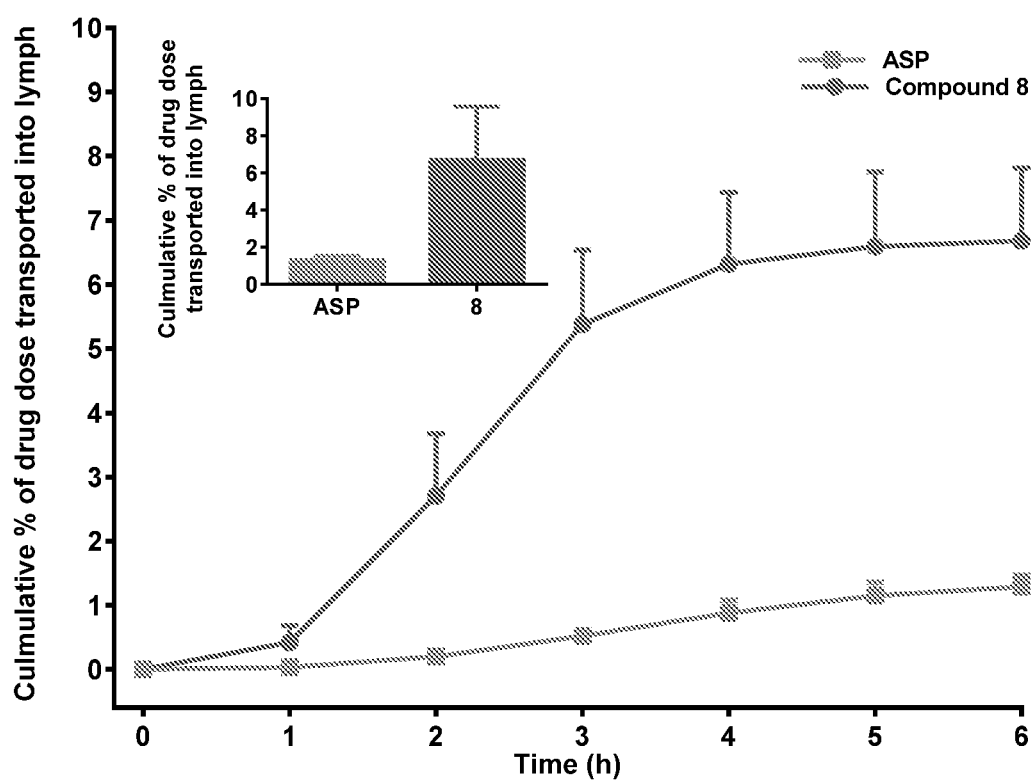
FIG. 9. Graphical representation of cumulative lymphatic transport of total aspirin (ASP) related derivatives (% of administered dose) versus time in anaesthetised, mesenteric lymph duct cannulated male SD rats following intraduodenal infusion of ASP and Compound 8.

The present inventor's data reveal that positional and function group specificity is important for efficient lymphatic targeting of MPA prodrugs. In FIG. 6 and Table 11, Compounds of the invention, such as Compound 30 and Compound 32, successfully promoted MPA lymphatic recovery by 43~60 fold. Conversely, compounds wherein MPA is directly conjugated at the 1' (or 3') position of the glycerol unit (Compound 42), compounds wherein the MPA-linker moiety is conjugated to the glycerol unit via an ether bond where the equivalent of —Y— is a $C_4$ alkyl group (Compound 43), or a $C_6$ alkyl group (Compound 44), or compounds wherein MPA is conjugated at the 1' position of the glycerol unit via an ether bond and the equivalent of —Y— is a $C_8$ alkyl group (Compound 45) were poor substrates for lymphatic transport, resulting in lymphatic transport that was similar to that of MPA alone.

TABLE 11

Lymphatic transport of total MPA related derivative
(% of administered dose) following intraduodenal infusion
to anaesthetised, mesenteric lymph-duct cannulated
rats (data are presented as mean ± SEM).

| Compound | Transport of total MPA derivatives in lymph (% of dose) | Increase fold (compared with MPA dosed group) |
| --- | --- | --- |
| MPA (n = 5) | 0.17 ± 0.05 | 1.0 |
| 30 (n = 3) | 7.1 ± 0.5 | 42.5 |
| 32 (n = 4) | 9.6 ± 1.4 | 57.5 |
| 42 (n = 4) | 0.28 ± 0.09 | 1.7 |
| 43 (n = 3) | 0.24 ± 0.04 | 1.5 |
| 44 (n = 4) | 0.31 ± 0.14 | 1.8 |
| 45 (n = 3) | 1.4 ± 0.2 | 8.4 |

FIGS. 7 to 11 and Table 12 provide additional evidence that the TG mimetic prodrug strategy can be extended to compounds beyond MPA and testosterone. The figures present the lymphatic transport of total compound (% of dose) following ID infusion to anaesthetised, mesenteric lymph-duct cannulated rats. The data show that the lymphatic transport of MET (FIG. 7), ATV (FIG. 8) and ASP (FIG. 9) is enhanced following administration of Compounds 3, 9 and 8, respectively.

Figure 10:
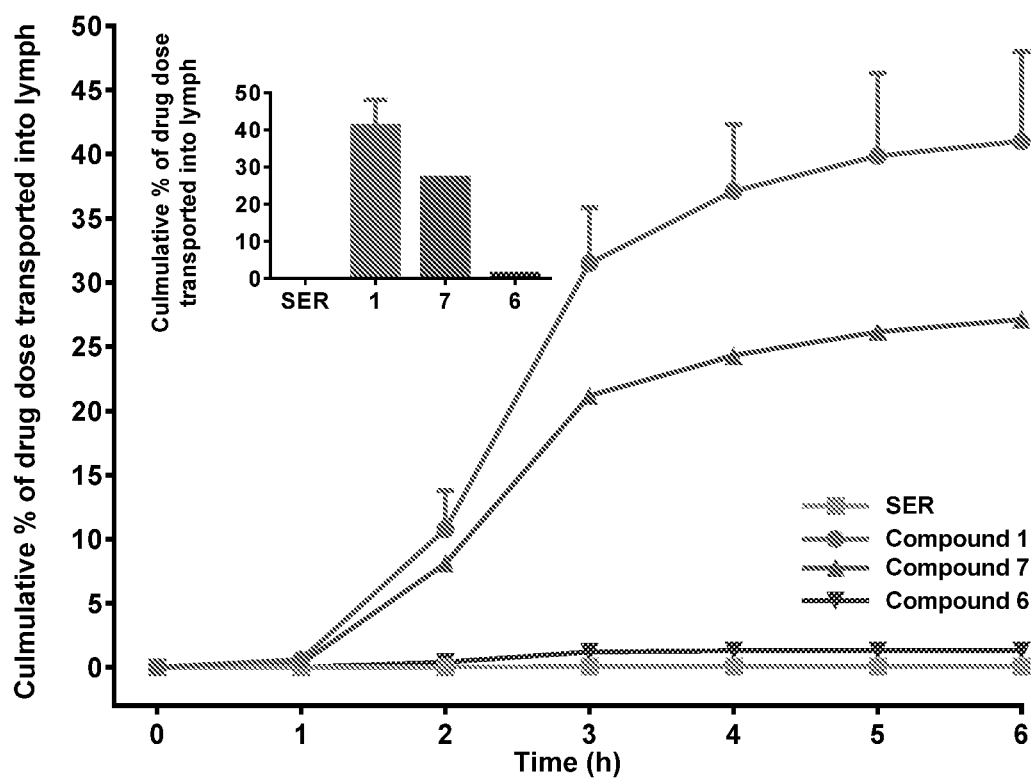
FIG. 10. Graphical representation of cumulative lymphatic transport of total sertraline (SER) related derivatives (% of administered dose) versus time in anaesthetised, mesenteric lymph duct cannulated male SD rats following intraduodenal infusion of SER and Compounds 1, 6 and 7.
Figure 11:
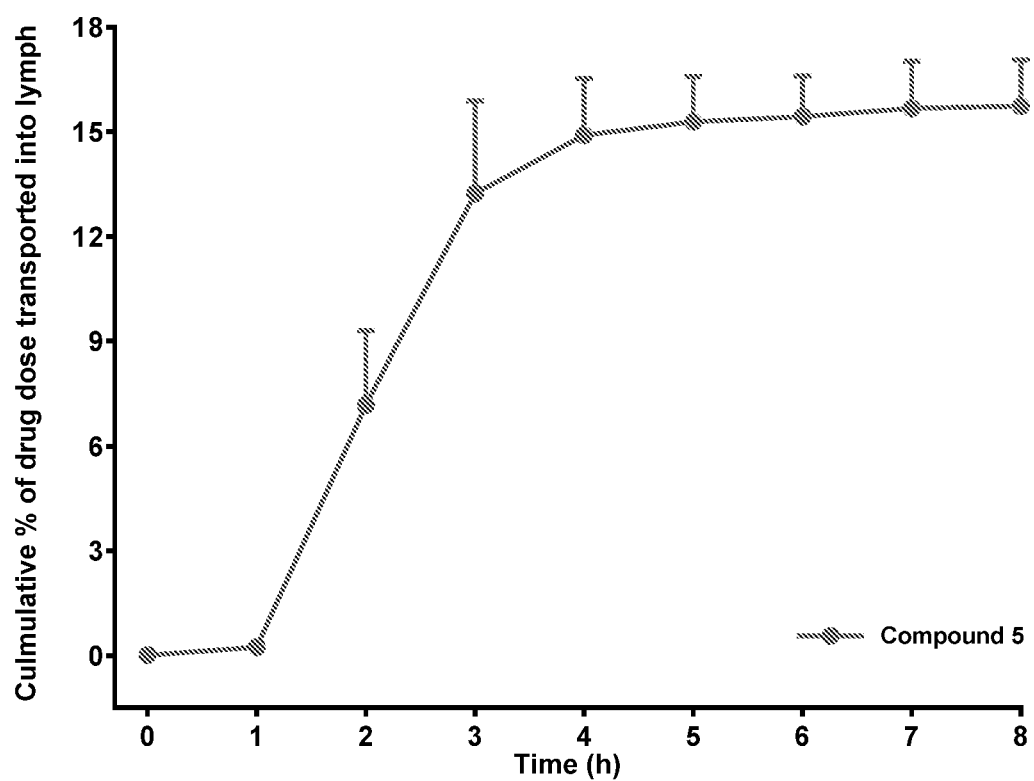
FIG. 11. Graphical representation of cumulative lymphatic transport of total celecoxib related derivatives (% of administered dose) versus time in anaesthetised, mesenteric lymph duct cannulated male SD rats following intraduodenal infusion of Compound 5.

FIG. 10 provides yet further evidence of the current invention and illustrates that in addition to examples of carboxylic acid terminated drugs such as MPA, and hydroxyl terminated drugs such as TST, that lymphatic drug transport of eg. amine terminated drugs such as sertraline (SER) can be enhanced by the formation of glyceride mimetic prodrugs that incorporate a self-immolative linker between the drug and the glyceride. FIG. 10 present the lymphatic transport of total compound (% of dose) following ID infusion to anaesthetised, mesenteric lymph-duct cannulated rats (data are presented as mean±range (n=2) of Compound 1, incorporating a trimethyl lock self-immolative group and the pharmaceutical agent sertraline, resulting in the transport of 41.0±7.0% of the total sertraline derivatives in lymph. Similarly, modification to include a para hydroxyl benzoate self immolative (Compound 6), or the combination of an acetal self immolative group and methyl protection of the ester link to the glyceride (Compound 7) provides for enhancement in lymphatic drug transport when compared to the drug alone. As a further example a trimethyl lock self-immolative prodrug of an amine containing drug, the lymphatic transport of a prodrug of the non steroidal anti-inflammatory drug celecoxib (CEL, Compound 5) is shown in FIG. 11.

TABLE 12

Lymphatic transport of total drug (% of administered dose)
following intraduodenal infusion to anaesthetised, mesenteric
lymph-duct cannulated rats (data are presented as mean ±
SEM when n ≥ 3 or mean ± range when n = 2).

| Compound | Transport of total drug derivatives in lymph (% of dose) | Increase fold (compared with parent drug group) |
| --- | --- | --- |
| MET (n = 2) | 0.02 ± 0.01 | 1.0 |
| 3 (n = 2) | 14.2 ± 1.5 | 591.7 |
| ATV (n = 1) | 0.17 | 1.0 |
| 9 (n = 3) | 5.0 ± 0.5 | 29.9 |
| ASP (n = 3) | 1.3 ± 0.2 | 1.0 |
| 8 (n = 4) | 6.7 ± 1.1 | 5.2 |
| SER (n = 1) | 0.05 | 1.0 |
| 1 (n = 2) | 41.0 ± 7.0 | 803.9 |
| 7 (n = 1) | 27.1 | 531.4 |
| 6 (n = 1) | 1.3 | 25.5 |
| 5 (n = 2) | 15.7 ± 1.3 | |

Example 9. Pharmacokinetic (PK) Studies in Rats and Dogs

In order to assess the oral bioavailability of the compounds of the invention, pharmacokinetic studies were conducted in rats and dogs. In rat studies, female (for testosterone related studies) or male (for alphaxolone related studies) Sprague-Dawley rats (240-320 g) was anaesthetised and the carotid artery was cannulated the day before drug administration. The rats were then allowed to regain consciousness and fasted overnight prior to the commencement of experiments with free access to water. The next morning, compounds (except for alphaxolone (ALP) and Compound 2) were administered via oral gavage in lipid formulations containing 1 to 2 mg of the compound, 40 mg oleic acid and 25 mg Tween 80 dispersed in 2 mL PBS (as described above for lymphatic transport studies in rats, the only difference being a smaller volume of PBS for the conscious studies here). The oral formulation of ALP contained 7.5 mg of ALP suspended in 1 mL of 0.5% (w/v) carboxymethyl cellulose and 0.4% (v/v) Tween 80 in saline). The oral formulation of Compound 2 contained 3 mg of the compound, 20 mg oleic acid and 12.5 mg Tween 80 dispersed in 1 mL PBS. Blood samples were collected from the carotid artery cannula from 5 min prior to administration up to 24 h post-dosing and centrifuged at 5000 rpm for 5 min to separate plasma.

During the blood sample collection period the rats had free access to water at all times but remained fasted for a further 8 hours following drug administration. Plasma samples were stored at −80° C. prior to assay by HPLC-MS-MS. In this case samples were assayed for free drug (i.e. non-glyceride associated drug) and were not hydrolysed prior to assay (as was the case with the lymph samples). This data therefore reflects drug that is transported into the lymph and then liberated from the re-esterified drug-glyceride complex in the systemic circulation.

For the dog studies, female greyhound dogs were held in a large animal research facility for at least 5 days prior to the commencement of studies. The dogs were allowed to acclimatise for at least 4 days prior to commencing the study. The dogs were fasted for 12 h up to 30 min prior to drug administration. For the fed state studies (n=4 for TU or Compound 13), dogs received 680 g of standard commercial dog food containing 5% fat min prior to drug administration. In the fasted study (n=1 for Compound 13), the dog remained fasted until after 4 h post-dose. Water was available ad libitum throughout the study for all dogs. On the study day, a 20 gauge intravenous catheter was inserted into a cephalic vein to allow blood sampling. The dogs were free to move around (not restrained) after cannulation. For the fed state studies, Andriol Testocaps (the commercial TU product) or Compound 13 was given to the dogs. Andriol Testocaps were supplied by Merck Sharp & Dohme (Australia) Pty Limited and were formulated as soft gelatin capsule containing a 12.0% (w/w) solution of TU in lauroglycol FCC/castor oil [40:60% (w/w)] with the individual capsule composition being 40 mg of TU, lauroglycol FCC, castor oil, gelatin, glycerol, and sunset yellow (E110). Compound 13 was prepared in a long-chain lipid based self-emulsifying drug delivery system (SEDDS) that consisted of 30.5% w/w soybean oil, 30.5% w/w Maisine 35-1, 31.6% w/w Cremophor EL and 7.4% w/w ethanol. Formulations were filled into hard gelatin capsules. Two capsules of Andriol Testocaps containing 80 mg TU or two capsules of Compound 13 containing a total dose of 90 mg Compound 13 dissolved in 2 g of the SEDDS formulation were administrated to the fed greyhound dog by placing the capsules as far posterior to the pharynx as possible, closing the mouth and rubbing the throat to stimulate swallowing. Subsequently 50 mL of water was administered orally via a syringe. Two capsules of Compound 13 formulation were also administrated to the fasted dogs for fasted state studies. After oral administration, blood samples (approx. 3 mL each) were taken via the cephalic vein cannula from 5 min prior to administration up to 10 hours post-dosing. The patency of the catheters was maintained by flushing with a small volume of heparinised saline (1-2 IU/mL) after each blood sample was withdrawn. Blood samples at 24 h were taken by venepuncture. Plasma was separated by centrifugation and aliquots of each plasma sample were transferred into eppendorf tubes and store at −80° C. prior to analysis by LC-MS-MS.

Figure 12:
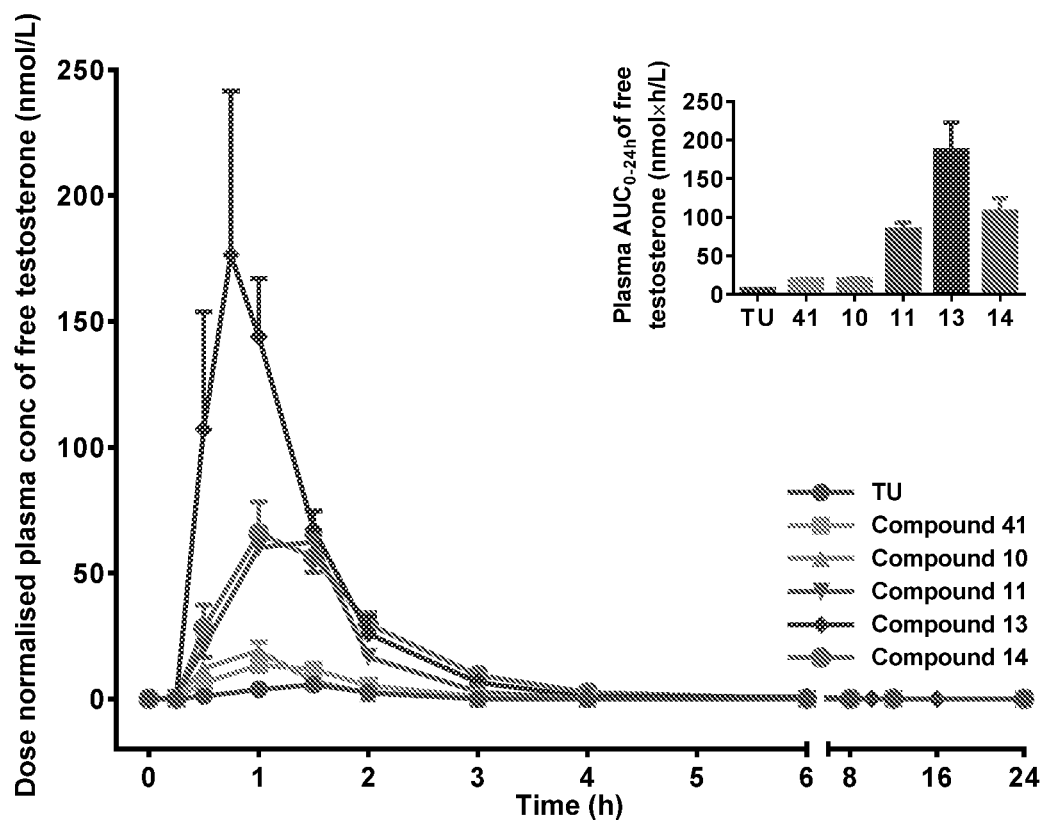
FIG. 12: Graphical representation of the dose-normalized testosterone plasma concentrations following oral gavage of testosterone undecanoate (TU) and Compounds 10, 11, 13, 14 and 40 to conscious, carotid artery cannulated female SD rats.

FIG. 12 illustrates dose-normalized testosterone plasma concentrations following oral gavage of formulations to conscious, carotid artery cannulated female SD rats. Formulations contained 1 mg of TU, or 2 mg of compounds of the invention containing testosterone dispersed in 40 mg oleic acid, 25 mg Tween 80 and 2 ml PBS. Doses are normalized to a 2 mg/kg equivalent dose of testosterone. Data are shown as mean±SEM for all groups (n=4 or 3 for each group). The embedded figure is the plot of the dose-normalized plasma $AUC_{0-24h}$ (nmol×h/L) of testosterone in the form of a bar graph.

Compounds of the invention with linker lengths greater than $C_5$ result in a significant increase in systemic exposure (oral bioavailability) of testosterone after administration. This is demonstrated by FIG. 12 and Table 13 where the systemic exposure of parent testosterone following oral administration of Compound 11, Compound 13 or Compound 14 was 10-fold (dose-normalised testosterone plasma $AUC_{0-24h}$) greater than that obtained after Compound 41 or Compound 10 administration (and ~12-27 fold higher than that achieved TU), in spite of the fact that lymphatic transport of all four compounds was similar (see FIG. 1 and Table 7). In this case the longer linker appears to be critical for enhanced drug release.

TABLE 13

Pharmacokinetic parameters after oral administration of the compound to conscious carotid artery cannulated SD female rats (doses are normalized to a 2 mg/kg equivalent testosterone dose and data are presented as mean ± SEM).

| Compound | Cmax (nmol/L) | Tmax (h) | $AUC_{0-24\,h}$ (nmol × h/L) | $AUC_{0-24\,h}$ fold increase compared with TU group |
|---|---|---|---|---|
| TU (n = 4) | 5.6 ± 0.5 | 1.5 ± 0.0 | 6.8 ± 0.4 | 1.0 |
| 41 (n = 4) | 13.7 ± 0.7 | 1.1 ± 0.1 | 19.6 ± 0.8 | 2.9 |
| 10 (n = 4) | 19.0 ± 3.6 | 1.0 ± 0.0 | 19.1 ± 2.4 | 2.8 |
| 11 (n = 4) | 69.9 ± 8.2 | 1.3 ± 0.1 | 84.2 ± 9.3 | 12.4 |
| 13 (n = 4) | 197.3 ± 53.4 | 0.9 ± 0.1 | 187.1 ± 35.8 | 27.4 |
| 14 (n = 4) | 68.2 ± 12.7 | 1.1 ± 0.1 | 107.0 ± 18.0 | 15.7 |

Figure 13:
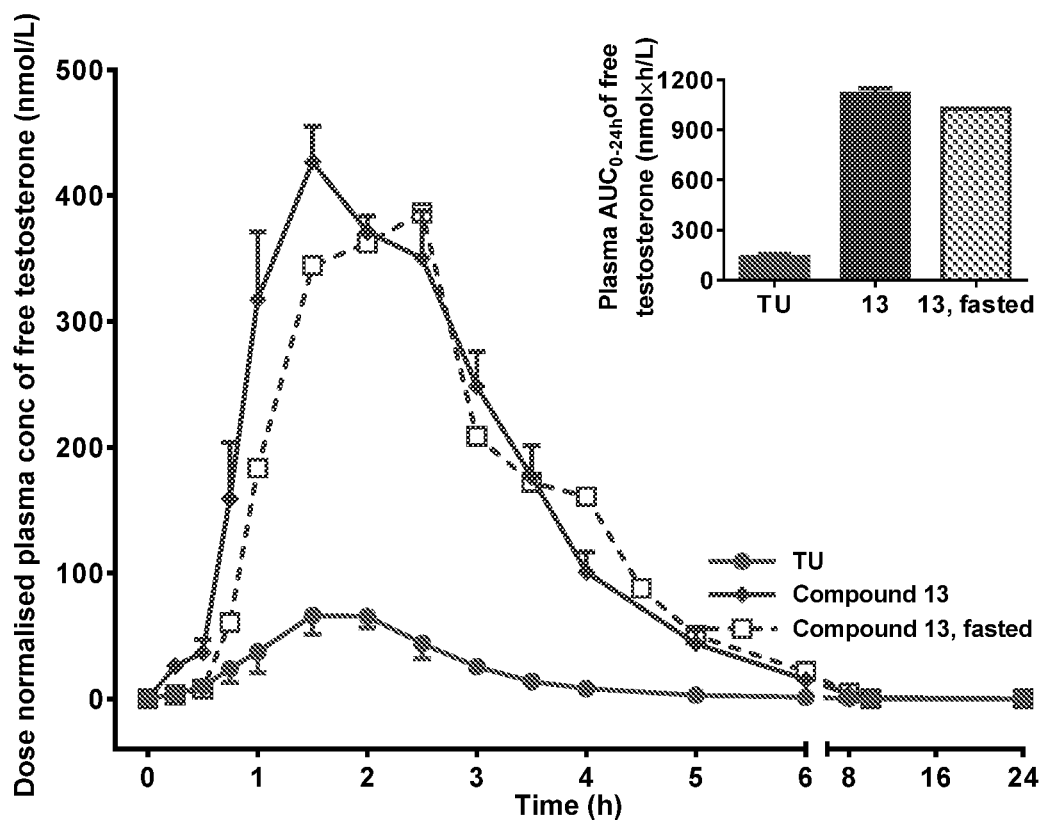
FIG. 13: Graphical representation of the dose-normalized testosterone plasma concentrations following oral administration of testosterone undecanoate (TU) (as the commercial product Testocaps) and Compound 13 to female greyhound dogs in the fed state or Compound 13 in the fasted state.

The utility of compounds of the invention to promote systemic exposure of testosterone was also shown in a different animal, in dogs. This is demonstrated by FIG. 13 and Table 14. Consistent with the rat data the systemic exposure of parent testosterone following oral administration of Compound 13 was significantly higher (approximately 8 fold, dose-normalised testosterone plasma AUC0-24 h) than that obtained after administration of TU. Notably, the increase in exposure for Compound 13 did not appear to be affected by co-administration with food.

TABLE 14

Pharmacokinetic parameters after oral administration of testosterone prodrugs to conscious greyhound dogs (doses are normalized to a 2 mg/kg equivalent testosterone dose) either in fed state or fasted state. Data are presented as mean ± SEM for TU (n = 4) and Compound 13 (n = 4) in fed state and n = 1 for Compound 13 in fasted state.

| Compound | Cmax (nmol/L) | Tmax (h) | $AUC_{0-24\,h}$ (nmol × h/L) | $AUC_{0-24\,h}$ fold increase compared with TU group |
|---|---|---|---|---|
| TU (n = 4) | 75.4 ± 12.8 | 1.8 ± 0.1 | 141.1 ± 22.1 | 1 |
| 13 (n = 4) | 455.3 ± 9.4 | 1.8 ± 0.3 | 1116.6 ± 32.4 | 7.9 |
| 13 (n = 1), fasted | 386.0 | 2.5 | 1026.8 | 7.3 |

Compounds with an ester link to the glyceride protected by either an alpha or a beta methyl group increase the oral bioavailability of testosterone for longer chain analogues.

As is evident from FIG. 4 and Table 9, methyl branched TG mimetic prodrugs facilitate the lymphatic transport of testosterone by stabilising MG intermediates. However, methyl group modification may also reduce the systemic release of parent testosterone from the prodrug molecules.

Figure 14:
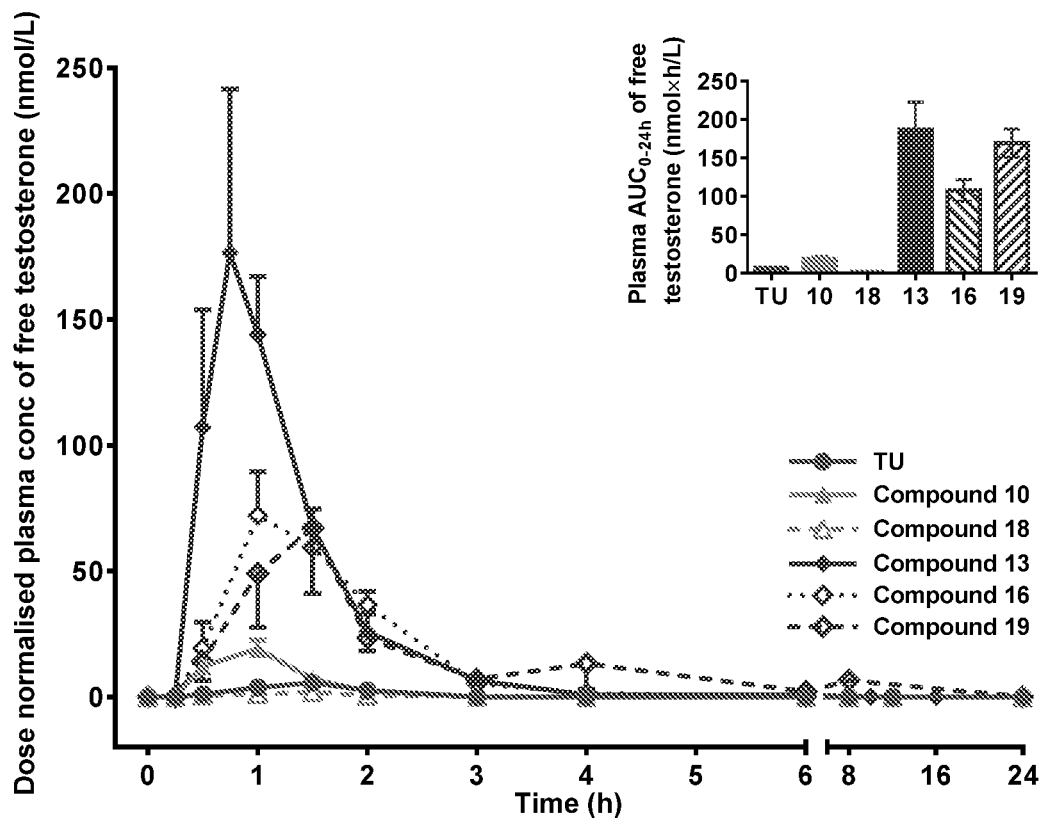
FIG. 14: Graphical representation of the dose-normalized testosterone plasma concentrations following oral gavage of testosterone undecanoate (TU) and Compounds 10, 13, 16, 18 and 19 to conscious, carotid artery cannulated female SD rats.

As shown in FIG. 14 and Table 15, for example, after administration of Compound 18, the systemic exposure of testosterone in plasma was lower than its straight chain counterpart, Compound 10, even though the lymphatic transport of Compound 18 was approximately 2 fold higher (see Table 9).

To improve lymphatic transport and also allow systemic testosterone release, the inventors have found that the combination of the methyl group substitution and a longer alkyl chain length attenuates the reduction in exposure observed for compounds with an alpha or beta methyl group. It can be seen from FIG. 14 and Table 15 that, when —Y— is increased to a $C_8$ alkyl group that after methyl group modification, the release of free testosterone in plasma was similar for the beta methylated analogue when compared to the straight chain (Compound 13) and release appeared to be somewhat delayed, providing for potentially extended release.

TABLE 15

Pharmacokinetic parameters after oral administration of compound to conscious carotid artery cannulated SD female rats (doses are normalized to a 2 mg/kg equivalent testosterone dose and data are presented as mean ± SEM).

| Compound | Cmax (nmol/L) | Tmax (h) | $AUC_{0-24\,h}$ (nmol × h/L) | $AUC_{0-24\,h}$ fold increase compared with TU group |
|---|---|---|---|---|
| TU (n = 4) | 5.6 ± 0.5 | 1.5 ± 0.0 | 6.8 ± 0.4 | 1.0 |
| 10 (n = 4) | 13.7 ± 0.7 | 1.1 ± 0.1 | 19.6 ± 0.8 | 2.9 |
| 18 (n = 3) | 1.8 ± 0.3 | 1.3 ± 0.2 | 2.0 ± 0.1 | 0.3 |
| 13 (n = 4) | 197.3 ± 53.4 | 0.9 ± 0.1 | 187.1 ± 35.8 | 27.4 |
| 16 (n = 4) | 77.0 ± 14.2 | 1.3 ± 0.1 | 107.6 ± 14.0 | 15.8 |
| 19 (n = 4) | 67.0 ± 25.8 | 1.5 ± 0.0 | 169.2 ± 8.1 | 24.9 |

Compounds that incorporate a self-immolative group between the pharmaceutical agent and the linker facilitate parent drug release in the systemic system to achieve higher oral bioavailability than the ester-linked compounds.

Figure 15:
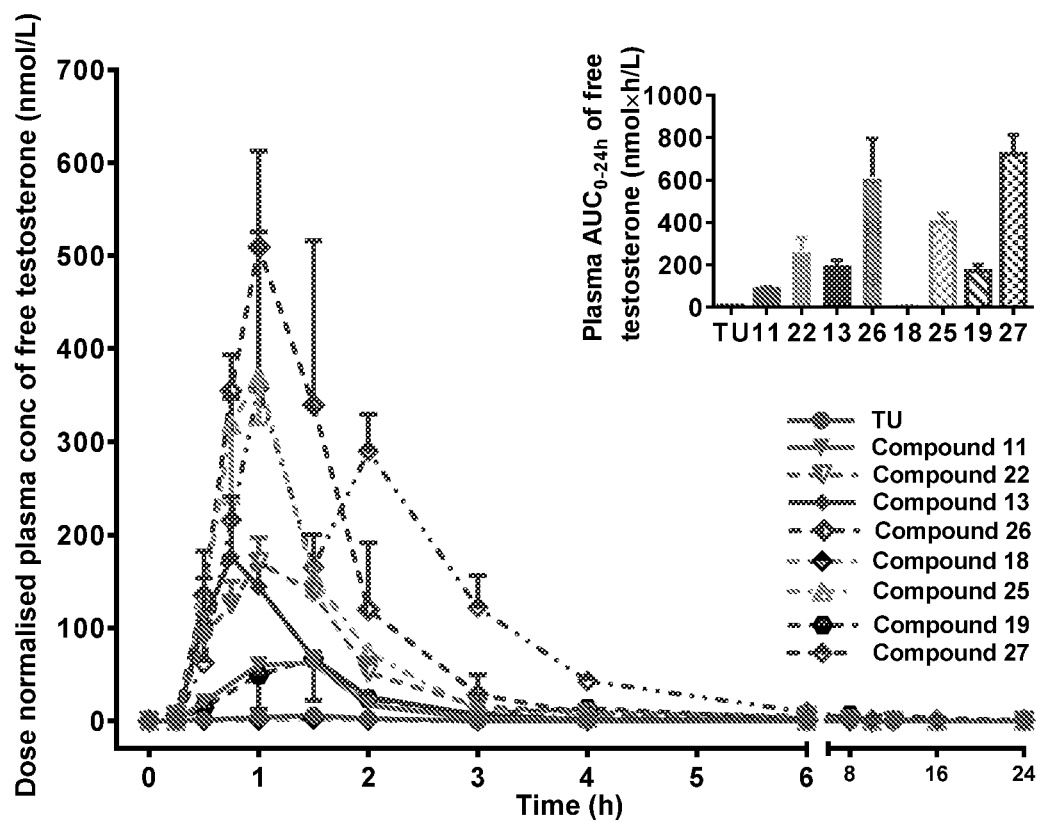
FIG. 15: Graphical representation of the dose-normalized testosterone plasma concentrations following oral gavage of testosterone undecanoate (TU) and Compounds 11, 13, 18, 19, 22, 25, 26 and 27 to conscious, carotid artery cannulated female SD rats.

As seen in FIG. 15 and Table 16, after oral administration of Compound 22 and Compound 26 (having a tri methyl lock self-immolative group), the systemic exposure of testosterone in plasma was higher than that achieved after administration of Compound 11 and Compound 13 (the equivalent compounds without the self immolative linker, and realising that Compound 13 was one of the previously best performing prodrugs), respectively. When compared with TU, the plasma AUC of testosterone was approximately 40 fold higher after administration of Compound 22 and approximately 90 fold higher after administration of Compound 26. Similarly, addition of the tri methyl lock self-immolative group to the beta-methyl protected testosterone prodrugs (where lymphatic transport was high (FIG. 4), but systemic release was incomplete (FIG. 15)) resulted in marked increases in systemic exposure for Compounds 25 and 27 (approximately 60-100 fold higher than TU).

TABLE 16

Pharmacokinetic parameters after oral administration to conscious carotid artery cannulated SD female rats (doses are normalized to a 2 mg/kg equivalent testosterone dose and data are presented as mean ± SEM when n ≥ 3 or mean ± Range when n = 2).

| Compound | Cmax (nmol/L) | Tmax (h) | $AUC_{0-24\,h}$ (nmol × h/L) | $AUC_{0-24\,h}$ fold increase compared with TU group |
|---|---|---|---|---|
| TU (n = 4) | 5.6 ± 0.5 | 1.5 ± 0.0 | 6.8 ± 0.4 | 1.0 |
| 11 (n = 4) | 69.9 ± 8.2 | 1.3 ± 0.1 | 84.2 ± 9.3 | 12.4 |
| 22 (n = 3) | 170.6 ± 27.0 | 1.0 ± 0.0 | 269.1 ± 58.8 | 39.4 |
| 13 (n = 4) | 197.3 ± 53.4 | 0.9 ± 0.1 | 187.1 ± 35.8 | 27.4 |
| 26 (n = 4) | 486.7 ± 133.9 | 1.1 ± 0.1 | 617.3 ± 177.8 | 90.5 |
| 18 (n = 3) | 1.8 ± 0.3 | 1.3 ± 0.2 | 2.0 ± 0.1 | 0.3 |
| 25 (n = 4) | 419.1 ± 63.3 | 0.9 ± 0.1 | 399.2 ± 43.2 | 58.5 |
| 19 (n = 3) | 67.0 ± 25.8 | 1.5 ± 0.0 | 169.2 ± 18.1 | 24.9 |
| 27 (n = 2) | 427.7 ± 97.8 | 1.5 ± 0.5 | 723.8 ± 90.5 | 106.4 |

It is also apparent that the trimethly lock self immolative group is not the only effective self immolative and other examples are similarly effective. For example, in FIG. 16 and Table 17, Compound 21 (having an acetal self-immolative group) resulted in higher systemic testosterone levels than Compound 11. This effect was even more marked when adding the acetal self immolative to the beta methyl protected C5 prodrug (Compound 23 vs Compound 18) where the self immolative analogue results in increases in systemic exposure of testosterone of 90 fold when compared to TU.

TABLE 17

Pharmacokinetic parameters after oral administration to conscious carotid artery cannulated SD female rats (doses are normalized to a 2 mg/kg equivalent testosterone dose and data are presented as mean ± SEM).

| Compound | Cmax (nmol/L) | Tmax (h) | $AUC_{0-24\,h}$ (nmol × h/L) | $AUC_{0-24\,h}$ fold increase compared with TU group |
|---|---|---|---|---|
| TU (n = 4) | 5.6 ± 0.5 | 1.5 ± 0.0 | 6.8 ± 0.4 | 1.0 |
| 11 (n = 4) | 69.9 ± 8.2 | 1.3 ± 0.1 | 84.2 ± 9.3 | 12.4 |
| 21 (n = 3) | 231.9 ± 63.2 | 0.7 ± 0.2 | 299.4 ± 100.1 | 44.0 |
| 18 (n = 3) | 1.8 ± 0.3 | 1.3 ± 0.2 | 2.0 ± 0.1 | 0.3 |
| 23 (n = 4) | 532.5 ± 168.5 | 1.1 ± 0.2 | 619.6 ± 266.3 | 90.8 |

Figure 17:
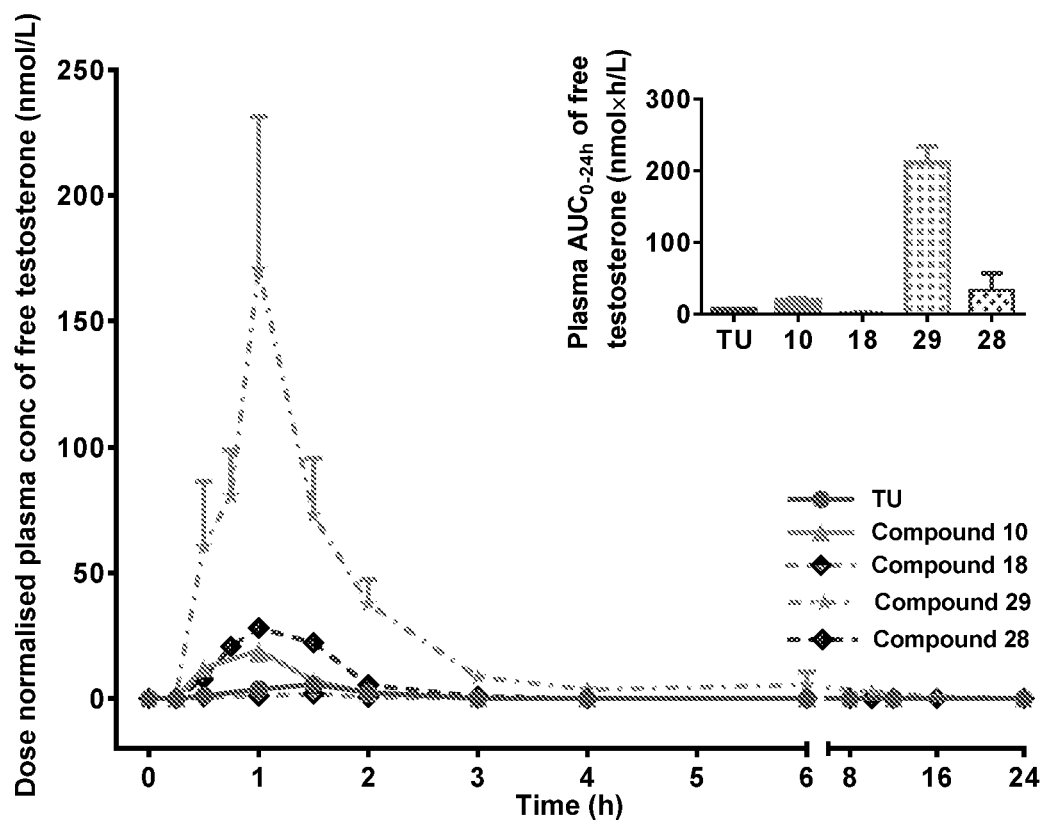
FIG. 17: Graphical representation of the dose-normalized testosterone plasma concentrations following oral gavage of testosterone undecanoate (TU) and Compounds 10, 18, 28 and 29 to conscious, carotid artery cannulated female SD rats.

In a further exemplification of the potential benefit of the self immolative groups, the data in FIG. 17 and Table 18 provide evidence of the utility of a flipped-ester self-immolative (FSI). The data for Compound 29 show that insertion of the flipped ester group to the C5 beta methyl testosterone prodrug results in a significant increase in systemic testosterone levels after oral administration when comparted to both the straight chain prodrug (Compound 10) and the beta methyl protected compound (Compound 18). The addition of a parahydroxybenzyl carbonyl (PHB) self-immolative (Compound 28) also resulted in increases in testosterone exposure when compared to TU, but was less effective than the other self-immolatives.

TABLE 18

Pharmacokinetic parameters after oral administration
to conscious carotid artery cannulated SD female rats
(doses are normalized to a 2 mg/kg equivalent testosterone
dose and data are presented as mean ± SEM).

| Compound | Cmax (nmol/L) | Tmax (h) | $AUC_{0-24\,h}$ (nmol × h/L) | $AUC_{0-24\,h}$ fold increase compared with TU group |
|---|---|---|---|---|
| TU (n = 4) | 5.6 ± 0.5 | 1.5 ± 0.0 | 6.8 ± 0.4 | 1.0 |
| 10 (n = 4) | 19.0 ± 3.6 | 1.0 ± 0.0 | 19.1 ± 2.4 | 2.8 |
| 18 (n = 3) | 1.8 ± 0.3 | 1.3 ± 0.2 | 2.0 ± 0.1 | 0.3 |
| 29 (n = 3) | 185.6 ± 45.8 | 0.9 ± 0.1 | 211.0 ± 13.0 | 30.9 |
| 28 (n = 4) | 30.8 ± 7.7 | 1.0 ± 0.2 | 33.3 ± 11.5 | 4.9 |

Figure 18:
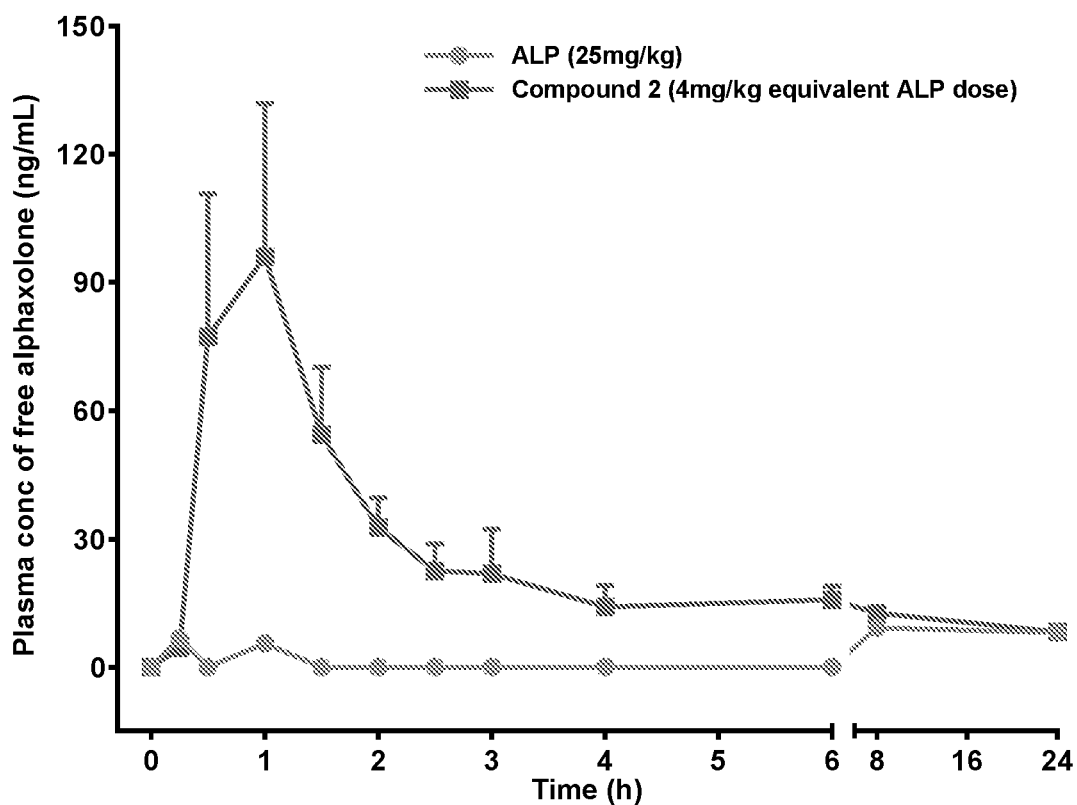
FIG. 18: Graphical representation of the alphaxolone (ALP) plasma concentrations following oral gavage of alphaxolone or Compound 2 to conscious, carotid artery cannulated male SD rats.

It is further apparent that compounds of the invention are able to promote systemic exposure of drugs other than testosterone, such as alphaxolone (ALP), another drug with high first-pass effect (FIG. 18 and Table 19). FIG. 18 illustrates ALP plasma concentrations following oral gavage of formulations to conscious, carotid artery cannulated male SD rats. Formulations contained 7.5 mg of ALP suspended in 1 mL 0.5% (w/v) carboxymethyl cellulose and 0.4% (v/v) Tween 80 in saline, or 3 mg of Compound 2 dispersed in 20 mg oleic acid, 12.5 mg Tween 80 and 1 ml PBS. Data are shown as mean±SEM for the Compound 2 group (n=4) and n=1 for the control compound ALP group). Following oral administration of ALP in a suspension formulation, the plasma concentrations were extremely low (below the limit of quantification (LOD, 10 ng/mL)), most likely due to extensive first-pass metabolism of ALP. Data are shown in FIG. 18 as a qualitative indication realising that they were below the limit of quantification of the assay In contrast, Compound 2 resulted in an obviously marked increase in systemic exposure (oral bioavailability) of ALP when compared to the control compound ALP, although a quantitative comparison of the relative bioavailability was not possible due to the very low exposure of ALP following ALP administration.

TABLE 19

Pharmacokinetic parameters of ALP after oral administration
to conscious carotid artery cannulated SD male rats (doses are
normalised to 25 mg/kg for ALP group, and to 4 mg/kg equivalent
ALP for Compound 2 group). Data are shown as mean ± SEM
for the Compound 2 group (n = 4) and n = 1 for the ALP group

| Compound | Cmax (ng/mL) | Tmax (h) | $AUC_{0-24\,h}$ (ng × h/mL) |
|---|---|---|---|
| ALP (n = 1) | Not available, as plasma drug concentrations were below LOQ (10 ng/mL) | | |
| 2 (n = 4) | 107.6 ± 27.0 | 1.3 ± 0.1 | 225.3 ± 58.5 |

Example 10. In Vitro Hydrolysis of Compounds by Rat Digestive Fluid or Porcine Pancreatic Lipase In vitro hydrolysis of MPA related compounds was performed via incubation with rat digestive fluid. Rat digestive fluid was collected from anesthetized rats via cannulation of the common bile-pancreatic duct immediately prior to the entry of the duct into the duodenum (i.e. below the point of entry of pancreatic secretions). This allowed simultaneous collection of bile and pancreatic fluid. The digestive fluid was collected continuously for 2 h, during which time a blank lipid formulation (prepared as described in the rat lymphatic transport studies but without the addition of drug) was infused into the duodenum at a rate of 2.8 ml/h to mimic conditions following drug administration. Bile and pancreatic fluid was maintained at 37° C. and used within 0.5 h of collection for in vitro prodrug hydrolysis experiments. The hydrolysis experiments were conducted via incubation (at 37° C.) of 0.375 mL of rat digestive fluid with 0.625 ml of the drug-loaded lipid formulations (as described in the rat lymphatic transport studies). The volume ratio of digestive fluid to formulation mimicked the flow rate of bile and pancreatic fluid (~1.5 mL/h) and the infusion rate of the intraduodenal formulations (2.8 mL/h) during the in vivo lymphatic transport studies. Aliquots of 10 μL (samples taken at 0, 2, 5, 10, 15, 30, 60, 90, 120, 180 min) were added to 990 μL of acetonitrile:water (4:1, v/v) to stop lipolysis, vortexed for 1 min and centrifuged at 4500 g for 5 min to precipitate proteins prior to analysis. The supernatant was analysed by HPLC-MS for residual compound concentrations, and the potential products of compound hydrolysis were analysed.

To provide for higher throughput of experiments, unless otherwise stated, in vitro hydrolysis of TST related compounds was performed via incubation with porcine pancreatic lipase. This provides a more reproducible source of pancreatic enzymes, facilitates enhanced experimental throughput and is also a greater challenge than collected rat enzymes (since enzyme activity in rat intestinal fluid is low). Briefly, pancreatic lipase solution was prepared prior to the hydrolysis experiment by dispersion of 1 g porcine pancreatin in 5 ml of lipolysis buffer and 16.9 μl of 5M NaOH. The suspension was mixed well and centrifuged at 3500 rpm for 15 minutes at 5° C. to provide a supernatant. An amount of 1000 ml of lipolysis buffer was prepared with 0.474 g of tris-maleate (2 mM), 0.206 g of $CaCl_2.H_2O$ (1.4 mM) and 8.775 g of NaCl (150 mM) adjusted with NaOH to pH 6.5. To assess the potential for prodrug hydrolysis in the intestine, 20 μl of prodrug solution (1 mg/ml dissolved in acetonitrile), 900 μl of simulated intestinal micellar solution [prepared with 0.783 g of NaTDC (3 mM) and 0.291 g of phosphatidyl choline (0.75 mM) in 500 ml lipolysis buffer] and 100 μl of enzyme solution were incubated at 37° C. 20 μl samples of the incubation solution were taken at 0, 5, 10, 15, 30, 60, 90, 120 and 180 minutes post incubation and added to 180 μl of ACN to stop lipolysis. The mixture was vortexed and centrifuged at 5000 rpm for 5 minutes to precipitate proteins prior to analysis. The supernatant was analysed by HPLC-MS for residual compound concentrations, and the potential products of compound hydrolysis were analysed.

On incubation with digestive enzymes the monoglycerides forms of the prodrugs are formed very rapidly. The stability in simulated intestinal conditions is therefore better assessed by the stability of the monoglycerides form that is generated by the initial digestion process. The monoglycerides form must remain intact to be absorbed and re-esterified in the enterocyte prior to entry into the lymphatics. A comparison of the stability profiles of the monoglyceride forms of Compound 10 (n=3) with Compound 18 (n=1) and Compound 13 (n=3) with Compound 16 (n=3) during in vitro incubation with freshly collected rat bile and pancreatic fluid (BPF) (Compounds 10 and 18) or porcine pancreatic lipase (Compounds 13 and 16) shows that the inclusion of a methyl group on the alpha or beta carbon significantly increases the stability of the monglyceride intermediates (FIG. 19). This is consistent with the increase in lymphatic transport of Compound 18 when compared to Compound 10, and the high extent of lymphatic transport of Compound 16 in FIG. 4.

Figure 20:
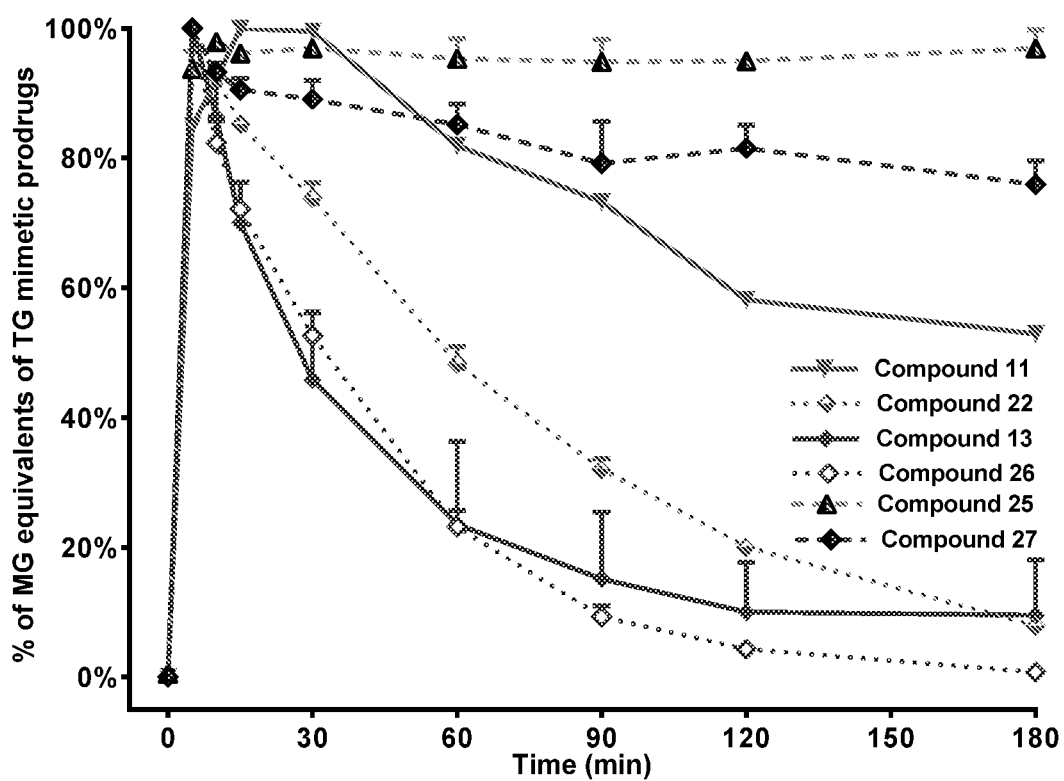
FIG. 20: Graphical representation of the stability profiles of the monoglyceride forms of Compounds 11, 13, 22, 25, 26 and 27 during in vitro incubation with porcine pancreatic lipase.
Figure 21:
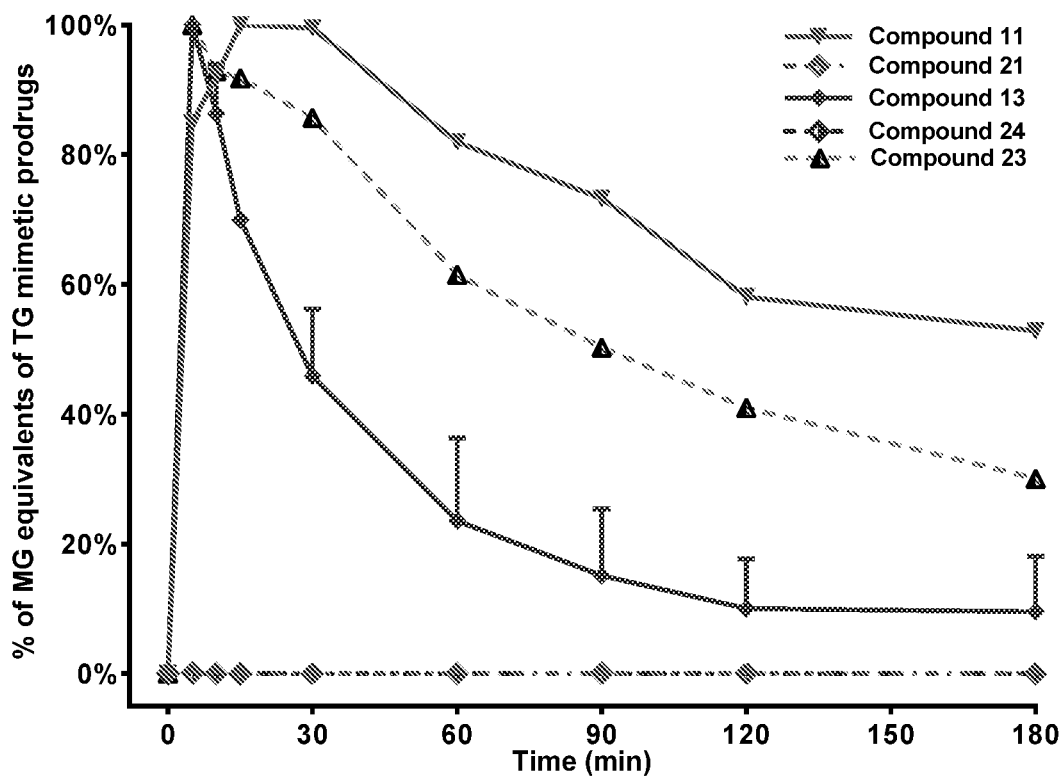
FIG. 21: Graphical representation of the stability profiles of the monoglyceride forms of Compound 11, 13, 21, 23 and 24 during in vitro incubation with porcine pancreatic lipase.
Figure 22:
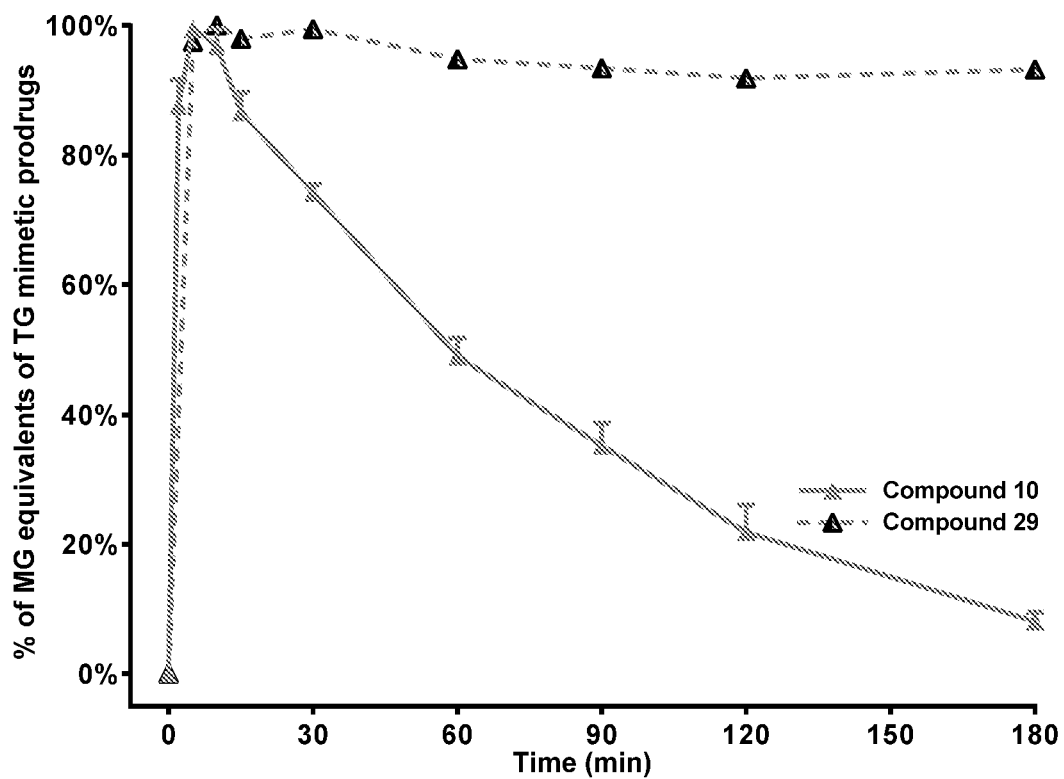
FIG. 22: Graphical representation of the stability profiles of the monoglyceride forms of Compounds 10 and 29 during in vitro incubation with porcine pancreatic lipase.

FIGS. 20 to 22 provide further evidence of the ability of methyl substitution to improve the luminal stability of testosterone prodrugs including prodrugs containing self immolative linkers, where the self immolative groups might be expected to reduce luminal stability. For example, in FIG. 20 the monoglycerides forms of compound 11 or compound 13 were not highly stable in the in vitro lipolysis assay and this was similar or worse for the tri-methyl lock self immolative analogues (Compound 22 and Compound 26). In contrast the methyl substituted monoglycerides (Compound 25 and Compound 27) were remarkably stable under in vitro hydrolysis challenge and resulted in increased testosterone exposure (FIG. 15).

Figure 16:
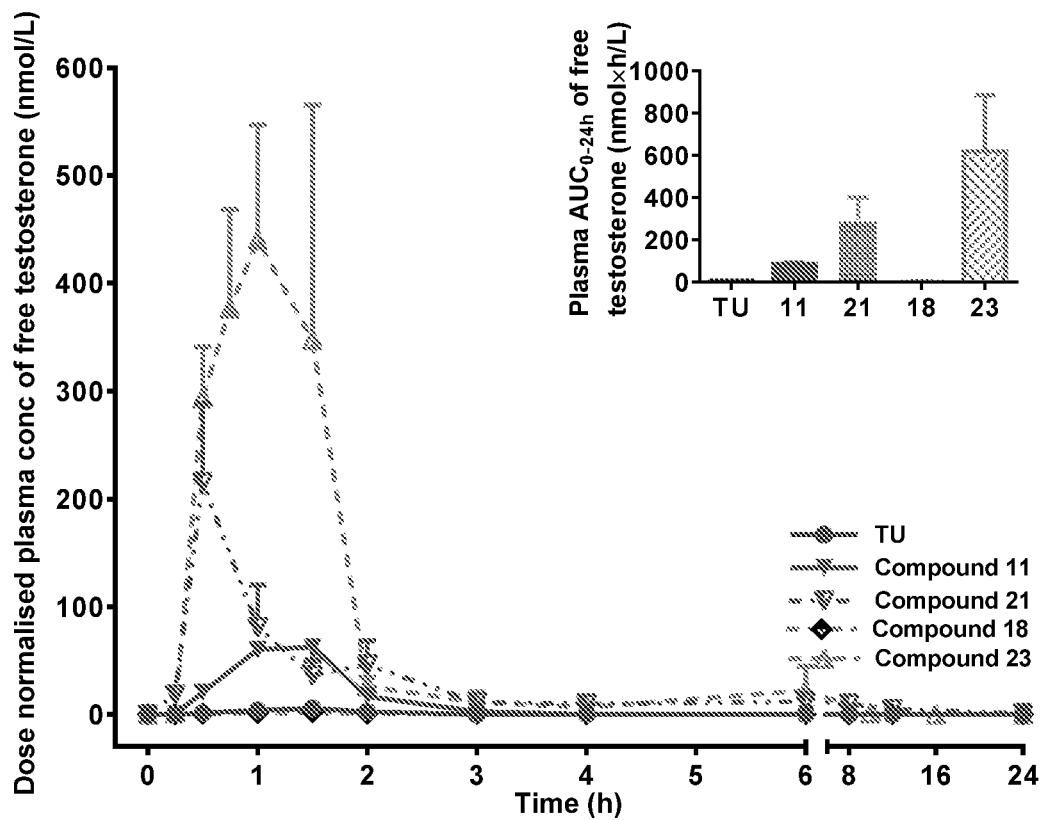
FIG. 16: Graphical representation of the dose-normalized testosterone plasma concentrations following oral gavage of testosterone undecanoate (TU) and Compounds 11, 18, 21 and 23 to conscious, carotid artery cannulated female SD rats.

In FIG. 21 a similar comparison is evident for the acetal self immolative prodrugs, where the luminal stability of Compound 21 (with the self immolative linker) was lower than that of Compound 11 and Compound 24 had a poorer stability than Compound 13. The combination of the acetal self immolative plus beta methyl protection in Compound 23 resulted in significantly enhanced luminal stability (FIG. 21) and in vivo exposure (FIG. 16).

For the flipped ester self immolative, a combination of insertion of the self immolative plus β methyl substitution (Compound 29), resulted in an increase in luminal stability relative to the non-self immolative straight chain counterpart (Compound 10) (FIG. 22), and significant increase in in vivo testosterone exposure (FIG. 17).

Figure 23:
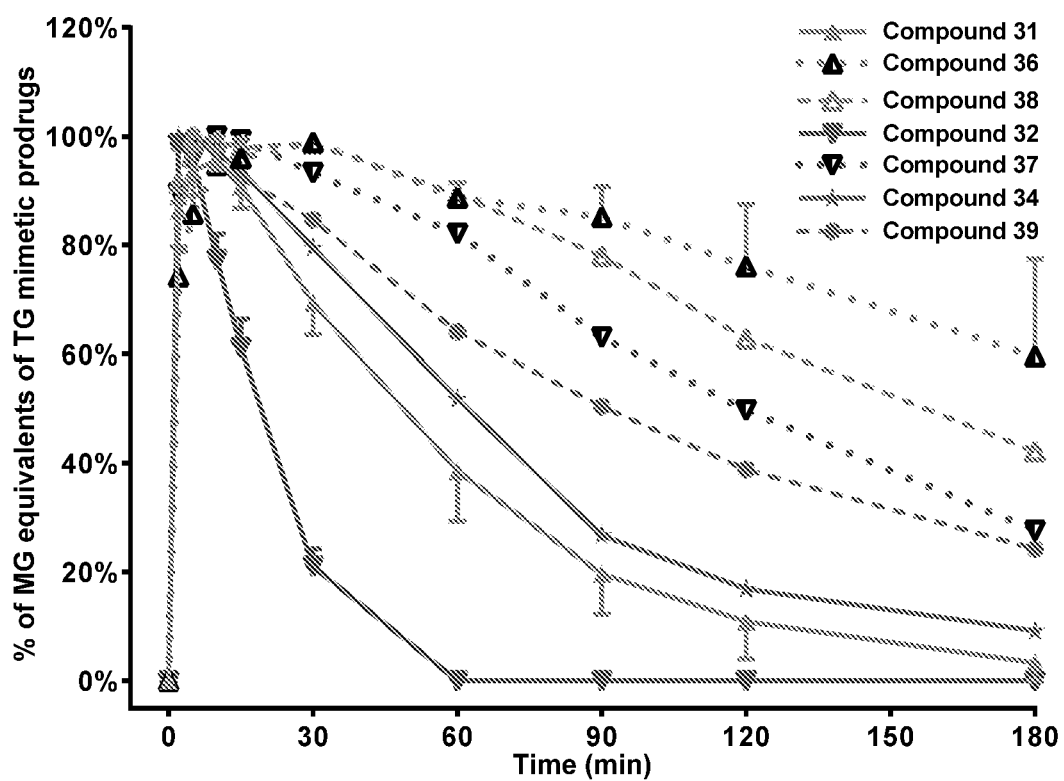
FIG. 23: Graphical representation of the stability profiles of the monoglyceride forms of Compounds 31, 32, 34, 36, 37, 38 and 39 during in vitro incubation with freshly collected rat bile and pancreatic fluid.

Similarly, a comparison of the stability profiles of the monoglyceride forms of Compound 31 (n=5), Compound 32 (n=4), Compound 34 (n=1), Compound 36 (n=2), Compound 37 (n=1), Compound 38 (n=1) and Compound 39 (n=1), during in vitro incubation with freshly collected rat bile and pancreatic fluid (BPF) is illustrated in FIG. 23 for MPA derivatives. Data are presented as mean±SEM when n≥3 or mean±Range when n=2.

Compounds with a methyl substitution in the linker (either α- or β- to the ester bond linking the alkyl group to the glyceride backbone) effectively reduce the degradation of monoglyceride intermediates in the gastrointestinal (GI) lumen, resulting in enhanced in vivo lymphatic transport when compared to their straight chain counterparts.

Comparison of degradation profiles of the monoglyceride digestion products of Compound 36, and Compound 38 with that from Compound 31, Compound 37 with that of Compound 32 and Compound 39 with that of Compound 34, reveal significant differences in stability. Optimisation of the stability of prodrugs in the GI lumen also resulted in a trend towards better in vivo lymphatic transport. FIG. 5 and Table 10 shows that lymphatic transport of Compound 36 (9.1%) or Compound 38 (12.1%) was slightly better than Compound 31 (8.2%), that Compound 37 (12.6%) resulted in higher transport than Compound 32 (9.6%) and that Compound 39 (28.4%) was higher than that of Compound 34 (22.1%)

Figure 24:
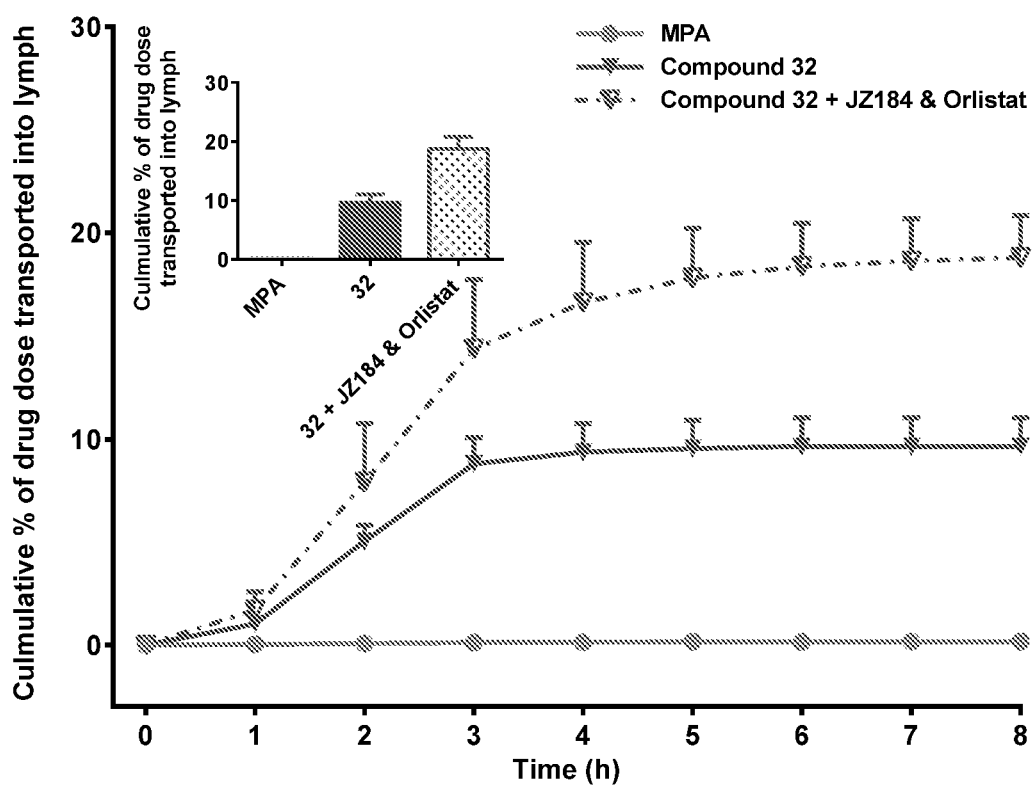
FIG. 24: Graphical representation of the cumulative lymphatic transport of total mycophenolic acid (MPA)-containing compounds (% of administered dose) versus time in anaesthetised, mesenteric lymph duct cannulated male SD rats following intraduodenal infusion of MPA and Compound 32 in the absence or presence of 0.6 mg of JZL184 and 9 µg of orlistat.

The data also demonstrate that the monoglyceride (MG) intermediates of prodrugs containing a straight chain linker (e.g. Compound 31 and Compound 32) are relatively rapidly degraded in BPF. It is likely that the instability of these MG intermediates results from breakdown via hydrolytic enzymes such as monoacylglycerol lipase and pancreatic lipase. This in turn reduces the availability of the drug conjugated MG-like intermediates to be absorbed and to be available for re-esterification. Ultimately this reduces lymphatic transport of drug. Protection of MG intermediates from degradation therefore may enhance lymphatic drug transport. This can be achieved structurally (such as the incorporation of alpha or beta methyl substitutions) or by co-administration of enzyme inhibitors, for example, the data in FIG. 24 and Table 20 shows that the lymphatic transport of Compound 32 was increased from 9.6 to 18.8% of the dose (p<0.05) by co-administration with a monoacylglycerol lipase inhibitor (JZL184) and a pancreatic lipase inhibitor (Orlistat).

TABLE 20

Lymphatic transport of total compound (% of administered dose) following intraduodenal infusion to anaesthetised, mesenteric lymph-duct cannulated rats (data are presented as mean ± SEM).

| Compound | Transport of total MPA derivatives in lymph (% of dose) | Increase fold (compared with MPA dosed group) |
|---|---|---|
| MPA (n = 5) | 0.17 ± 0.05 | 1.0 |
| 32 (n = 4) | 9.6 ± 1.4 | 57.5 |
| 32 + JZL184 & Orlistat (n = 3) | 18.8 ± 2.0 | 112.4 |

Throughout this specification and claims which follow, unless the context requires otherwise, the word "comprise", and variations such as "comprises" or "comprising", will be understood to imply the inclusion of a stated integer or group of integers or steps but not the exclusion of any other integer or group of integers.

The reference in this specification to any prior publication (or information derived from it), or to any matter which is known, is not, and should not be taken as an acknowledgment or admission or any form of suggestion that prior publication (or information derived from it) or known matter forms part of the common general knowledge in the field of endeavour to which this specification relates.

We claim:
1. A compound of the formula (I):

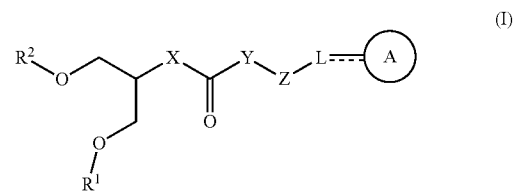

wherein
R$^1$ and R$^2$ independently represent H or a C$_2$-C$_{28}$ fatty acid;
—X— is selected from —O—, —NH—, and —S—;
—Y— represents a substituted —C$_3$-C$_{20}$alkyl-, —C$_3$-C$_{20}$alkenyl-, or —C$_3$-C$_{20}$alkynyl- group, wherein one or more of the carbon atoms in the alkyl, alkenyl, or alkynyl group may be replaced with NH, S, O, a C$_5$-C$_8$ aromatic or aliphatic cyclic group, or a C$_5$-C$_8$ aromatic or aliphatic heterocyclic group, provided that the alkyl, alkenyl, or alkynyl group does not exceed a length equivalent to a linear C$_{20}$alkyl group;

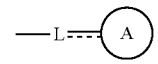

represents a pharmaceutical agent;
—L— is —X'— or —X' C(O)—;
X' is O, S, N, N(R$^4$), or S(O)$_2$NH;

═══ represents a single bond when X' is O, S, N(R⁴), or S(O)₂NH; or
═══ represents two separate bonds when X' is N;
—Z— is —C(O)— or —C(O)R³— when —L— is —X'—; or
—Z— is absent when —L— is —X'C(O)—;
R³ is a self-immolative group; and
R⁴ is H or C₁-C₄alkyl; or
a pharmaceutically acceptable salt thereof.

2. The compound according to claim 1, wherein R³ is selected from:

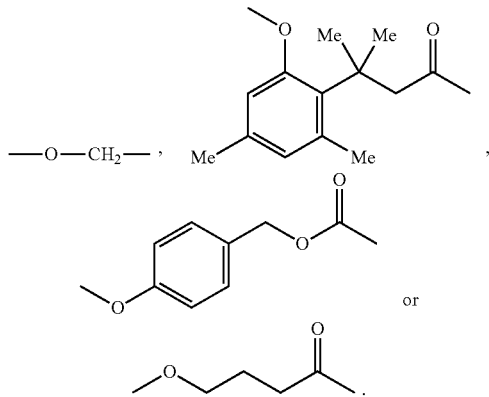

3. The compound of the formula (I) according to claim 1, represented by the formula (II):

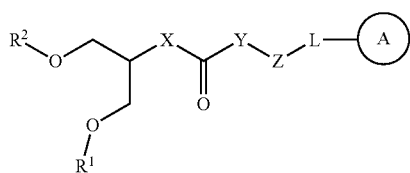

wherein
R¹ and R² independently represent H or a C₂-C₂₈ fatty acid;
—X— is selected from —O—, —NH—, and —S—;
—Y— represents a substituted —C₃-C₂₀alkyl-, —C₃-C₂₀alkenyl-, or —C₃-C₂₀alkynyl- group, wherein one or more of the carbon atoms in the alkyl, alkenyl, or alkynyl group may be replaced with NH, S, O, a C₅-C₈ aromatic or aliphatic cyclic group, or a C₅-C₈ aromatic or aliphatic heterocyclic group, provided that the alkyl, alkenyl, or alkynyl group does not exceed a length equivalent to a linear C₂₀alkyl group;

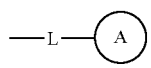

represents a pharmaceutical agent;
—L— is —X'— or —X' C(O)—;
X' is O, S, or N(R⁴);
R⁴ is H or C₁-C₄alkyl; and
—Z— is —C(O)— when —L— is —X'—; or
—Z— is absent when —L— is —X'C(O)—; or
a pharmaceutically acceptable salt thereof.

4. The compound according to claim 1, represented by the formula (III):

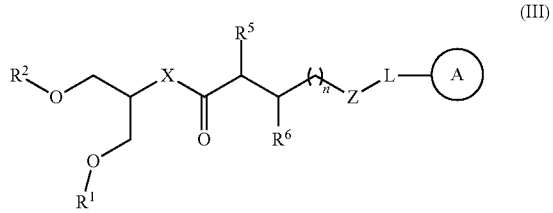

wherein
R¹, R², —X—,

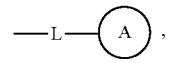

and —Z— are as defined in claim 1;
R⁵ and R⁶ are individually selected from hydrogen and C₁-C₄alkyl, provided that one or both of R⁵ and R⁶ are not hydrogen; and
n is from 1 to 18; or
a pharmaceutically acceptable salt thereof.

5. The compound according to claim 4, wherein the pharmaceutical agent is selected from testosterone, mycophenolic acid, oestrogens (estrogen), morphine, metoprolol, raloxifene, alphaxolone, a statin, buprenorphine, pentazocine, propranolol, L-DOPA, midazolam, lidocaine, chlorpromazine, amitriptyline, nortriptyline, isosorbidedinitrate, oxprenolol, labetalol, verapamil, salbutamol, epitiostanol, or melphalan.

6. The compound according to claim 5, wherein the pharmaceutical agent is testosterone and the compound is represented by the formula (IV):

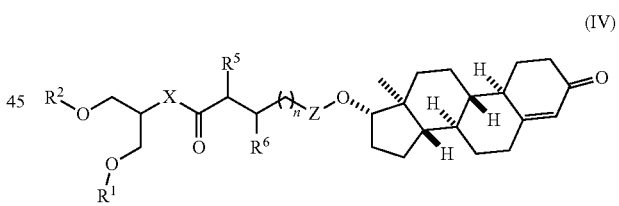

wherein R¹, R², and X are as defined in claim 1;
R⁵ and R⁶ are individually selected from hydrogen and C₁-C₄alkyl, provided that one or both of R⁵ and R⁶ are not hydrogen;
—Z— is —C(O)— or —C(O)R³—;
R³ is a self-immolative group; and
n is from 1 to 18; or
a pharmaceutically acceptable salt thereof.

7. The compound according to claim 4, wherein R⁵ is methyl and R⁶ is hydrogen.

8. The compound according to claim 4, wherein R⁵ is hydrogen and R⁶ is methyl.

9. The compound according to claim 1, wherein —X— and —X'— are oxygen.

10. The compound according to claim 1, wherein —X— is —O— and R¹ and R² are independently selected from a C₂-C₂₈ fatty acid.

11. The compound according to claim 1, wherein the pharmaceutical agent is selected from non-steroidal anti-inflammatory medications (NSAIDS), COX-2 inhibitors, corticosteroid anti-inflammatory medications, anti-malarial medications, nitrosoureas, platinum, anthracyclines, drugs acting on immunophilins, opioids, immunosuppressants, and pharmaceutically active peptides.

12. A pharmaceutical composition comprising a therapeutically effective amount of a compound according to claim 1, or a pharmaceutically acceptable salt thereof, together with at least one pharmaceutically acceptable carrier or diluent.

13. The compound of claim 1, wherein —X— is —O—.

14. The compound of claim 13, wherein —Z— is —C(O)— or —Z— is absent.

15. The compound of claim 13, wherein —Z— is —C(O)R³—.

16. The compound of claim 13, wherein —Z— is —C(O)— or —Z— is absent; R¹ and R² are independently selected from a $C_2$-$C_{28}$ fatty acid; and —Y— represents a substituted —$C_8$-$C_{20}$alkyl-, —$C_8$-$C_{20}$alkenyl-, or —$C_8$-$C_{20}$alkynyl- group, wherein one or more of the carbon atoms in the —$C_8$-$C_{20}$alkyl-, —$C_8$-$C_{20}$alkenyl-, or —$C_8$-$C_{20}$alkynyl- group of —Y— may be replaced with NH, S, or O.

17. The compound of claim 13, wherein —Y— represents a —$C_3$-$C_{20}$alkyl-, —$C_3$-$C_{20}$alkenyl-, or —$C_3$-$C_{20}$alkynyl- group substituted with one or more groups selected from hydroxyl, alkyl, alkoxy, alkoxycarbonyl, alkenyl, alkenyloxy, alkynyl, alkynyloxy, amino, aminoacyl, thio, arylalkyl, arylalkoxy, aryl, aryloxy, acylamino, carboxy, cyano, halogen, nitro, sulfo, phosphono, phosphorylamino, phosphinyl, heteroaryl, heteroaryloxy, heterocyclyl, heterocycloxy, trihalomethyl, pentafluoroethyl, trifluoromethoxy, difluoromethoxy, trifluoromethanethio, trifluoroethenyl, mono- and di-alkylamino, mono- and di-(substituted alkyl)amino, mono- and di-arylamino, mono- and di-heteroarylamino, mono- and di-heterocyclyl, amino, and unsymmetric di-substituted amines having different substituents selected from alkyl, aryl, heteroaryl, and heterocyclyl, wherein one or more of the carbon atoms in the —$C_3$-$C_{20}$alkyl-, —$C_3$-$C_{20}$alkenyl-, or —$C_3$-$C_{20}$alkynyl- group of —Y— may be replaced with NH, S, or O.

18. The compound of claim 13, wherein —Y— represents a —$C_3$-$C_{20}$alkyl-, —$C_3$-$C_{20}$alkenyl-, or —$C_3$-$C_{20}$alkynyl- group substituted with one or more $C_1$-$C_{20}$ alkyl groups, wherein one or more of the carbon atoms in the —$C_3$-$C_{20}$alkyl-, —$C_3$-$C_{20}$alkenyl-, or —$C_3$-$C_{20}$alkynyl- group of —Y— may be replaced with NH, S, or O.

19. The compound of claim 13, wherein —Y— represents a —$C_3$-$C_{20}$alkyl- group substituted with one or more $C_1$-$C_{20}$ alkyl groups, wherein one or more of the carbon atoms in the —$C_3$-$C_{20}$alkyl- group of —Y— may be replaced with O.

20. The compound of claim 13, wherein —Y— represents a —$C_3$-$C_{20}$alkyl- group substituted with one or more groups selected from methyl, ethyl, n-propyl, isopropyl, n-butyl, sec-butyl, t-butyl, n-pentyl, or hexyl.

21. The compound of claim 13, wherein —Z— is —C(O)— or —Z— is absent; R¹ and R² are independently selected from a $C_2$-$C_{28}$ fatty acid; and —Y— represents a —$C_3$-$C_{20}$alkyl- group substituted with one or more groups selected from methyl, ethyl, n-propyl, isopropyl, n-butyl, sec-butyl, t-butyl, n-pentyl, or hexyl, wherein one or more of the carbon atoms in the —$C_3$-$C_{20}$alkyl- group of —Y— may be replaced with S or O.

22. The compound of claim 13, wherein R¹ and R² are independently selected from a $C_2$-$C_{28}$ fatty acid; and —Y— represents a —$C_3$-$C_{20}$alkyl- group substituted with one or two groups selected from methyl, ethyl, or isopropyl, wherein one or more of the carbon atoms in the —$C_3$-$C_{20}$alkyl- group of —Y— may be replaced with O.

23. The compound of claim 13, wherein —Y— represents a substituted —$C_8$-$C_{20}$alkyl-, wherein one or more of the carbon atoms in the —$C_8$-$C_{20}$alkyl- group may be replaced with NH, S, or 0.

24. The compound of claim 23, wherein —Y— is substituted with one or more $C_1$-$C_{20}$ alkyl groups, wherein one or more of the carbon atoms in the —$C_8$-$C_{20}$alkyl- group of —Y— may be replaced with NH, S, or 0.

25. The compound of claim 23, wherein —Z— is —C(O)— or —Z— is absent; R¹ and R² are independently selected from a $C_2$-$C_{28}$ fatty acid; and —Y— is substituted with one or two methyl groups and one carbon atom in the —$C_8$-$C_{20}$alkyl- group of —Y— may be replaced with O.

26. The compound of claim 1, wherein the pharmaceutical agent is selected from aspirin, ibuprofen, naproxen, celecoxib, rofecoxib, prednisolone, hydroxychloroquine, cyclophosphamide, methotrexate, azathioprine, mercaptopurine, fluorouracil, dactinomycin, mitomycin C, bleomycin, mithramycin, sulfasalazine, leflunomide, mycophenolate, fingolimod, myriocin, chlorambucil, doxorubicin, nelarabine, cortisone, dexamethasone, prednisone, pralatrexate, vinblastine, bortezomib, thiotepa, nelarabine, daunorubicin hydrochloride, clofarabine, cytarabine, dasatinib, imatinib mesylate, ponatinib hydrochloride, vincristine sulfate, bendamustine hydrochloride, fludarabine phosphate, bosutinib, nilotinib, omacetaxine mepesuccinate, anastrozole, capecitabine, letrozole, paclitaxel, gemcitabine, fulvestrant, tamoxifen, lapatinib, toremifene, ixabepilone, eribulin, albendazole, ivermectin, diethylcarbamazine, albendazole, doxycycline, closantel, maraviroc, enfuvirtide, deoxythymidine, zidovudine, stavudine, didanosine, zalcitabine, abacavir, lamivudine, emtricitabine, tenofovir, nevirapine, delavirdine, efavirenz, rilpivirine, raltegravir, elvitegravir, lopinavir, indinavir, nelfinavir, amprenavir, ritonavir, acyclovir, daunarubicin, ciclosporin, tacrolimus, sirolimus, mycophenolic acid, or cyclosporine.

27. A compound of formula (I):

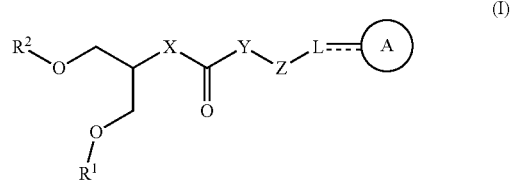

wherein
R¹ and R² independently represent a $C_2$-$C_{28}$ fatty acid;
—X— is —O—;
—Y— represents an unsubstituted, straight-chain —$C_7$-$C_{20}$alkyl-, —$C_7$-$C_{20}$alkenyl-, or —$C_7$-$C_{20}$alkynyl- group, wherein one or more of the carbon atoms in the alkyl, alkenyl, or alkynyl group may be replaced with NH, S, or O, provided that the alkyl, alkenyl, or alkynyl group does not exceed a length equivalent to a linear $C_{20}$alkyl group;

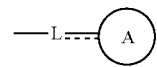

represents a pharmaceutical agent;
—L— is —X'— or —X'C(O)—;
X' is O, S, N, N(R⁴), or S(O)₂NH;

═══ represents a single bond when X' is O, S, N(R⁴), or S(O)₂NH; or
═══ represents two separate bonds when X' is N;
—Z— is —C(O)— or —C(O)R³— when —L— is —X'—; or
—Z— is absent when —L— is —X'C(O)—;
R³ is a self-immolative group; and
R⁴ is H or $C_1$-$C_4$alkyl;
or a pharmaceutically acceptable salt thereof.

28. The compound of claim 27, wherein R³ is selected from:

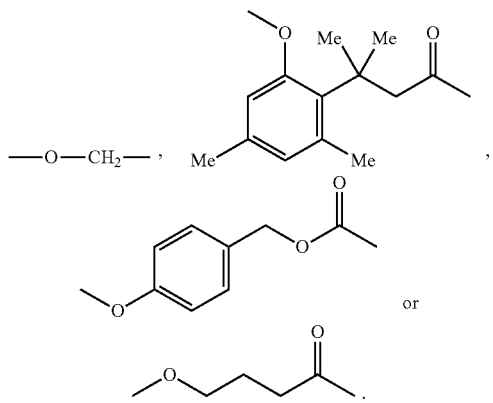

29. The compound of claim 27, wherein —Z— is —C(O)R³—.

30. The compound of claim 27, wherein —Z— is —C(O)— or is absent.

31. The compound of claim 27, wherein —Y— represents an unsubstituted, straight-chain —$C_8$-$C_{20}$alkyl-, wherein one or more of the carbon atoms in the alkyl group may be replaced with NH, S, or O.

32. The compound of claim 27, wherein the pharmaceutical agent is selected from non-steroidal anti-inflammatory medications, COX-2 inhibitors, corticosteroid anti-inflammatory medications, anti-malarial medications, nitrosoureas, platinum, anthracyclines, drugs acting on immunophilins, opioids, immunosuppressants, or pharmaceutically active peptides.

33. The compound of claim 27, wherein the pharmaceutical agent is selected from aspirin, ibuprofen, naproxen, celecoxib, rofecoxib, prednisolone, dexamethasone, hydroxychloroquine, cyclophosphamide, methotrexate, azathioprine, mercaptopurine, fluorouracil, dactinomycin, mitomycin C, bleomycin, mithramycin, sulfasalazine, leflunomide, mycophenolate, fingolimod, myriocin, chlorambucil, doxorubicin, nelarabine, cortisone, prednisone, pralatrexate, vinblastine, bortezomib, thiotepa, nelarabine, daunorubicin hydrochloride, clofarabine, cytarabine, dasatinib, imatinib mesylate, ponatinib hydrochloride, vincristine sulfate, bendamustine hydrochloride, fludarabine phosphate, bosutinib, nilotinib, omacetaxine mepesuccinate, anastrozole, capecitabine, letrozole, paclitaxel, gemcitabine, fulvestrant, tamoxifen, lapatinib, toremifene, ixabepilone, eribulin, albendazole, ivermectin, diethylcarbamazine, albendazole, doxycycline, closantel, maraviroc, enfuvirtide, deoxythymidine, zidovudine, stavudine, didanosine, zalcitabine, abacavir, lamivudine, emtricitabine, tenofovir, nevirapine, delavirdine, efavirenz, rilpivirine, raltegravir, elvitegravir, lopinavir, indinavir, nelfinavir, amprenavir, ritonavir, acyclovir, daunarubicin, ciclosporin, tacrolimus, sirolimus, mycophenolic acid, or cyclosporine.

34. A pharmaceutical composition comprising a compound of claim 27, or a pharmaceutically acceptable salt thereof, together with at least one pharmaceutically acceptable carrier or diluent.

35. A method of treating or preventing a disease or disorder in which increased testosterone levels are beneficial, comprising administering to a subject in need thereof a therapeutically effective amount of a compound of claim 27, or a pharmaceutically acceptable salt thereof.

36. The method according to claim 35, wherein the disease or disorder is hypogonadism, anemia due to bone marrow failure, anemia due to renal failure, chronic respiratory failure, chronic cardiac failure, a steroid-dependent autoimmune disorder, AIDS wasting, hereditary angioedema or urticaria, terminal breast cancer, or menopause.

37. The method according to claim 35, wherein the compound is administered orally with food to promote transport to the intestinal lymph, or is co-administered orally with a lipid based formulation to promote transport to the intestinal lymph.

38. The compound of claim 27, wherein —Y— represents an unsubstituted, straight-chain —$C_8$-$C_{20}$alkyl- and wherein one or more of the carbon atoms in the alkyl group may be replaced with O.

39. The compound of claim 30, wherein —Y— represents an unsubstituted, straight-chain —$C_8$-$C_{20}$alkyl- and wherein one or more of the carbon atoms in the alkyl group may be replaced with O.

40. The compound of claim 27, wherein —Y— represents an unsubstituted, straight-chain —$C_{10}$-$C_{20}$alkyl-, wherein one of the carbon atoms in the alkyl group may be replaced with O.

41. The compound of claim 30, wherein —Y— represents an unsubstituted, straight-chain —$C_{10}$-$C_{20}$alkyl- and wherein one or more of the carbon atoms in the alkyl group may be replaced with O.

42. The compound of claim 27, wherein R¹ and R² are each palmitic acid (—C(O)$C_{15}H_{31}$).

43. The compound of claim 27, wherein —L— is —X'C(O)—.

44. The compound of claim 43, wherein X' is O.

45. The compound of claim 27, wherein —Y— represents an unsubstituted, straight-chain —$C_8$alkyl-.

46. The compound of claim 27, wherein the pharmaceutical agent is selected from testosterone, mycophenolic acid, oestrogens (estrogen), morphine, metoprolol, raloxifene, alphaxolone, buprenorphine, pentazocine, propranolol, L-DOPA, midazolam, lidocaine, chlorpromazine, amitriptyline, nortriptyline, isosorbidedinitrate, oxprenolol, labetalol, verapamil, salbutamol, epitiostanol, melphalan, lovastatin, atorvastatin, dexamethasone, bortezomib, dasatinib, imatinib mesylate, ponatinib hydrochloride, bosutinib, nilotinib, ciclosporin, tacrolimus, or sirolimus.

47. The compound of claim 38, wherein the pharmaceutical agent is selected from aspirin, ibuprofen, naproxen, celecoxib, rofecoxib, prednisolone, dexamethasone, hydroxychloroquine, cyclophosphamide, methotrexate, azathioprine, mercaptopurine, fluorouracil, dactinomycin, mitomycin C, bleomycin, mithramycin, sulfasalazine, leflunomide, mycophenolate, fingolimod, myriocin, chlorambucil, doxorubicin, nelarabine, cortisone, prednisone, pralatrexate, vinblastine, bortezomib, thiotepa, nelarabine, daunorubicin hydrochloride, clofarabine, cytarabine, dasatinib, imatinib mesylate, ponatinib hydrochloride, vincristine sulfate, bendamustine hydrochloride, fludarabine phosphate, bosutinib, nilotinib, omacetaxine mepesuccinate, anastrozole, capecitabine, letrozole, paclitaxel, gemcitabine, fulvestrant, tamoxifen, lapatinib, toremifene, ixabepilone, eribulin, albendazole, ivermectin, diethylcarbamazine, albendazole, doxycycline, closantel, maraviroc, enfuvirtide, deoxythymidine, zidovudine, stavudine, didanosine, zalcitabine, abacavir, lamivudine, emtricitabine, tenofovir, nevirapine, delavirdine, efavirenz, rilpivirine, raltegravir, elvitegravir, lopinavir, indinavir, nelfinavir, amprenavir, ritonavir, acyclovir, daunarubicin, ciclosporin, tacrolimus, sirolimus, mycophenolic acid, or cyclosporine.

48. The compound of claim 38, wherein the pharmaceutical agent is selected from testosterone, mycophenolic acid, oestrogens (estrogen), morphine, metoprolol, raloxifene, alphaxolone, buprenorphine, pentazocine, propranolol, L-DOPA, midazolam, lidocaine, chlorpromazine, amitriptyline, nortriptyline, isosorbidedinitrate, oxprenolol, labetalol, verapamil, salbutamol, epitiostanol, melphalan, lovastatin, atorvastatin, dexamethasone, bortezomib, dasatinib, imatinib mesylate, ponatinib hydrochloride, bosutinib, nilotinib, ciclosporin, tacrolimus, or sirolimus.

49. The compound of claim 39, wherein the pharmaceutical agent is selected from aspirin, ibuprofen, naproxen, celecoxib, rofecoxib, prednisolone, dexamethasone, hydroxychloroquine, cyclophosphamide, methotrexate, azathioprine, mercaptopurine, fluorouracil, dactinomycin, mitomycin C, bleomycin, mithramycin, sulfasalazine, leflunomide, mycophenolate, fingolimod, myriocin, chlorambucil, doxorubicin, nelarabine, cortisone, prednisone, pralatrexate, vinblastine, bortezomib, thiotepa, nelarabine, daunorubicin hydrochloride, clofarabine, cytarabine, dasatinib, imatinib mesylate, ponatinib hydrochloride, vincristine sulfate, bendamustine hydrochloride, fludarabine phosphate, bosutinib, nilotinib, omacetaxine mepesuccinate, anastrozole, capecitabine, letrozole, paclitaxel, gemcitabine, fulvestrant, tamoxifen, lapatinib, toremifene, ixabepilone, eribulin, albendazole, ivermectin, diethylcarbamazine, albendazole, doxycycline, closantel, maraviroc, enfuvirtide, deoxythymidine, zidovudine, stavudine, didanosine, zalcitabine, abacavir, lamivudine, emtricitabine, tenofovir, nevirapine, delavirdine, efavirenz, rilpivirine, raltegravir, elvitegravir, lopinavir, indinavir, nelfinavir, amprenavir, ritonavir, acyclovir, daunarubicin, ciclosporin, tacrolimus, sirolimus, mycophenolic acid, or cyclosporine.

50. The compound of claim 39, wherein the pharmaceutical agent is selected from testosterone, mycophenolic acid, oestrogens (estrogen), morphine, metoprolol, raloxifene, alphaxolone, buprenorphine, pentazocine, propranolol, L-DOPA, midazolam, lidocaine, chlorpromazine, amitriptyline, nortriptyline, isosorbidedinitrate, oxprenolol, labetalol, verapamil, salbutamol, epitiostanol, melphalan, lovastatin, atorvastatin, dexamethasone, bortezomib, dasatinib, imatinib mesylate, ponatinib hydrochloride, bosutinib, nilotinib, ciclosporin, tacrolimus, or sirolimus.

\* \* \* \* \*

UNITED STATES PATENT AND TRADEMARK OFFICE
CERTIFICATE OF CORRECTION

| | | |
|---|---|---|
| PATENT NO. | : 11,311,512 B2 | Page 1 of 1 |
| APPLICATION NO. | : 15/502757 | |
| DATED | : April 26, 2022 | |
| INVENTOR(S) | : Porter et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 770 days.

Signed and Sealed this
Eighth Day of October, 2024

Katherine Kelly Vidal
*Director of the United States Patent and Trademark Office*